US008598159B2

(12) United States Patent
Kaplan et al.

(10) Patent No.: US 8,598,159 B2
(45) Date of Patent: Dec. 3, 2013

(54) THERAPEUTIC PYRAZOLOQUINOLINE DERIVATIVES

(75) Inventors: Alan P. Kaplan, San Diego, CA (US); Varsha Gupta, Encinitas, CA (US); Jan W. F. Wasley, Guilford, CT (US)

(73) Assignee: Dart Neuroscience (Cayman) Ltd., Grand Cayman (KY)

( * ) Notice: Subject to any disclaimer, the term of this patent is extended or adjusted under 35 U.S.C. 154(b) by 230 days.

(21) Appl. No.: 12/949,655

(22) Filed: Nov. 18, 2010

(65) Prior Publication Data

US 2011/0065693 A1    Mar. 17, 2011

Related U.S. Application Data

(62) Division of application No. 12/135,036, filed on Jun. 6, 2008, now Pat. No. 7,872,002.

(60) Provisional application No. 60/943,005, filed on Jun. 8, 2007.

(51) Int. Cl.
*A61K 31/55* (2006.01)
*A61K 31/535* (2006.01)
*A61K 31/445* (2006.01)
*C07D 243/08* (2006.01)
*C07D 413/04* (2006.01)
*C07D 401/04* (2006.01)

(52) U.S. Cl.
USPC ............... 514/217.04; 514/232.2; 514/232.8; 514/315; 540/575; 544/126; 544/361

(58) Field of Classification Search
USPC ............. 514/232.8, 315, 232.2, 217.04; 544/126, 361; 540/575
See application file for complete search history.

(56) References Cited

U.S. PATENT DOCUMENTS

| | | | |
|---|---|---|---|
| 4,552,874 A | 11/1985 | Mardin et al. | |
| 4,690,930 A | 9/1987 | Takada et al. | |
| 4,814,450 A | 3/1989 | Yokoyama | |
| 5,334,595 A | 8/1994 | Wentland | |
| 6,686,373 B2 | 2/2004 | Kawamura et al. | |
| 7,872,002 B2 * | 1/2011 | Kaplan et al. ............. | 514/217.04 |
| 2005/0004159 A1 | 1/2005 | Hibi et al. | |
| 2005/0245563 A1 | 11/2005 | Boyle et al. | |
| 2006/0035919 A1 | 2/2006 | Matthews et al. | |
| 2006/0100229 A1 | 5/2006 | Hays et al. | |
| 2007/0078083 A1 | 4/2007 | Barlow et al. | |

FOREIGN PATENT DOCUMENTS

| | | |
|---|---|---|
| EP | 0 214 092 | 8/1986 |
| WO | WO 99/06401 A1 | 2/1999 |

OTHER PUBLICATIONS

Allen et al., "Synthesis of novel 2-Phenyl-2*H*-pyrazolo[4,3-*c*]isoquinolin-3-ols: Topological Comparisons with Analogues of 2-Phenyl-2,5-dihydropyrazolo[4,3-*c*]quinolin-3(3*H*)-ones at benzodiazepine receptors," *J. Med. Chem.*, 1992, 35(2): 368-374.

Atack et al., "The proconvulsant effects of the $GABA_A$ $\alpha 5$ subtype-selective compound RY-080 may not be $\alpha 5$-mediated", European Journal of Pharmacology, 2006, 548:77-82.

Barnard et al., "International Union of Pharmacology. XV. Subtypes of $\gamma$-Aminobutyric Acid$_A$ Receptors: Classification on the Basis of Subunit Structure and Receptor Function" Pharmacol. Rev., 1998, 50(2):291-313.

Carotti et al., "High Affinity Central Benzodiazepine Receptor Ligands. Part 3: Insights Into the Pharmacophore and Pattern Recognition Study of Intrinsic Activities of Pyrazole[4,3-*c*]quinolin-3-ones," Bioorg. & Med. Chem., 2003, 11(23): 5259-5272.

Fryer et al., "Structure Activity Relationships of 2-Phenylpyrazolo[4,3-*c*]quinolin-3-ones and their N- and O-Methyl Analogs at Benzodiazepine Receptors," Med. Chem. Res., 1993, 3: 122-130.

Jacobsen et al., "Piperazine imidazo[1,5-*a*]quinoxaline Ureas as High-Affinity $GABA_A$ Ligands of Dual Functionality", *J. Med. Chem.*, 1999, 42(7): 1123-1144.

Lister et al., "A pharmacokinetic study of CGS-8216, a benzodiazepine receptor ligand, in the rat," *Psychopharmacology*, 1984, 84: 420-422.

Low et al., "Molecular and Neuronal Substrate for the Selective Attenuation of Anxiety", *Science*, 2000, 290:131-134.

McKernan et al., "Sedative but not anxiolytic properties of benzodiazepines are mediated by the $GABA_A$ receptor $\alpha_1$ subtype", *Nat. Neurosci.*, 2000, 3:587-592.

Muller, "New trends in benzodiazepine research", *Drugs of Today*, 1988, 24:649-663.

(Continued)

*Primary Examiner* — James O Wilson
*Assistant Examiner* — Ebenezer O Sackey
(74) *Attorney, Agent, or Firm* — Knobbe Martens Olson & Bear LLP

(57) ABSTRACT

The invention provides a novel chemical series of formula I, as well as methods of use thereof for binding to the benzodiazepine site of the $GABA_A$ receptor and modulating $GABA_A$, and use of the compound of formula I for the treatment of $GABA_A$ receptor associated disorders. The general structure of formula I is shown below and can exist in tautomeric forms:

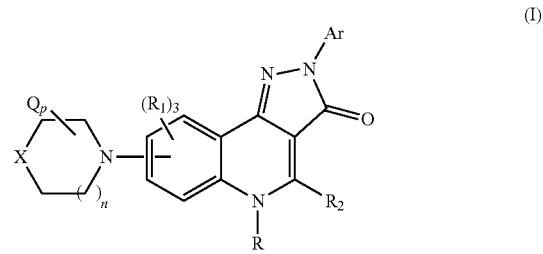

(I)

The invention further provides a method of modulation of one or more $GABA_A$ subtypes in an animal comprising administering to the animal an effective amount of a compound of formula (I).

7 Claims, No Drawings

(56) References Cited

OTHER PUBLICATIONS

Rudolph et al., "Benzodiazepine actions mediated by specific $\gamma$-aminobutyric acid$_A$ receptor subtypes", *Nature*, 1999, 401:796-800.

Takada et al., "Thienylpyrazoloquinolines: Potent Agonists and Inverse Agonists to Benzodiazepine Receptors", *J. Med. Chem.*, 1988, 31:1738-1745.

Yokoyama et al., "2-Arylpyrazolo[4,3-c]quinolin-3-ones: Novel agonist, Partial Agonist and Antagonist of Benzodiazepines" *J. Med. Chem.*, 1982, 25:337-339.

International Search Report for corresponding PCT Application No. PCT/US08/66201 mailed Oct. 7, 2008.

International Written Opinion for corresponding PCT Application No. PCT/US08/66201 mailed Oct. 7, 2008.

* cited by examiner

THERAPEUTIC PYRAZOLOQUINOLINE DERIVATIVES

RELATED APPLICATIONS

This application is a divisional of U.S. patent application Ser. No. 12/135,036, filed Jun. 6, 2008, which claims priority under 35 U.S.C. §119(e) to U.S. Provisional Application No. 60/943,005, filed Jun. 8, 2007; the disclosure of which are incorporated herein by reference in their entireties.

BACKGROUND OF THE INVENTION

1. Field of the Invention

The present invention is related to the use of novel derivatives of pyrazoloquinolines as modulators of $GABA_A$ $\alpha 5$ for the intended use of therapy for enhancing cognition.

2. Description of the Related Art

The inhibitory neurotransmitter γ-aminobutyric acid (GABA), serves as a ligand for two distinct classes of receptors, $GABA_A$ and $GABA_B$. The $GABA_A$ class is a ligand-gated ion channel while $GABA_B$ is a canonical seven transmembrane G-protein coupled receptor. The $GABA_A$ receptor is comprised of a number of subunits, including α, β, γ, and δ. Cloning of the individual subunits of the $GABA_A$ receptor has confirmed the existence, so far, of six α subunits, three β subunits, three γ subunits, and one δ subunit. The overall structure of the receptor is a pentamer with a minimum subunit requirement of at least one α subunit, one β subunit, and one γ subunit.

Due to afore mentioned diversity of subunits, there are more than 10,000 possible combinations of the subunits that comprise the $GABA_A$ receptor, though not all appear in nature. Specific combinations that have been identified to have biological relevance (and their relative abundance in rat brains, include α1β2γ2 (43%), α2β2/3γ2 (18%), α3βγ2/3 (17%), α2βγ1 (8%), α5β3γ2/3 (4%), α6βγ2 (2%), α6β3 (2%), and α4β3 (3%) (Barnard, E. A., et al. (1998) *Pharmacol. Rev.* 50: 291-313 incorporated herein in its entirety).

There are a number of distinct, small molecule binding sites on the $GABA_A$ receptor that modulate the activity of the receptor including sites for benzodiazepines, steroids, barbiturates, ethanol, and convulsants (e.g. picrotoxin). The GABA binding site is located at the α/β interface. A tremendous amount of pharmaceutical research has been invested in identifying compounds that bind to the benzodiazepine binding site (BZ-site), which is located at the α/γ interface. Binding of GABA is greatly modulated by binding of drugs to the BZ-site, which can cause a number of different pharmacological responses. Drugs such as diazepam and zolpidem, agonists of $GABA_A$ function, have shown historic success as anxiolytic agents (Muller, W. E. (1988) *Drugs of Today* 24: 649-663 incorporated herein in its entirety). More recent work has suggested that the sedative and hypnotic effects of these drugs are primarily due to interaction with the α1-containing receptors, therefore much effort has been focused on finding drugs that have preferential activity towards α2β2γ2 and α3βγ2 over α1βγ2 to maintain the anxiolytic activity but reduce the sedative side effects (Rudolph, U. F., et al. (1999) *Nature* 401: 796-800 incorporated herein in its entirety; Löw, K. F., et al. (2000) *Science* 290: 131-134 incorporated herein in its entirety; McKernan, R. M., et al. (2000) *Nat. Neurosci.* 3: 587-592 incorporated herein in its entirety).

The α5-subunit is predominantly found in the hippocampus, a part of brain that plays a part in memory and spatial navigation. As a result, much research has been focused on identifying links between α5-containing GABA receptor function and cognition. Results from a number of laboratories have indicated that selective inverse agonism of the α5β2/3 $GABA_A$ receptor can show marked improvement of memory function in a number of animal models. There have been a growing number of examples of inverse agonists in both the patent and scientific literature (Yokoyama, N., et al. (1982) *J. Med. Chem.* 25: 337-339 incorporated herein in its entirety; Takada, S., et al. (1988) *J. Med. Chem.* 31: 1738-1745 incorporated herein in its entirety; Atack, J. R., et al. (2006) *European Journal of Pharmacology* 548: 77-82 incorporated herein in its entirety). A preferable profile for a cognitive enhancer is one that shows negative modulation at α5, but with less modulation of α1, α2, or α3 to minimize side effects such as convulsion or sedation. As yet, no α5 selective $GABA_A$ negative modulator has been brought to market, and only a limited number have been investigated in human clinical trials.

SUMMARY OF THE INVENTION

The invention provides a novel chemical series of formula I, and methods of use thereof for binding to the benzodiazepine site of the $GABA_A$ receptor and negatively modulating the α5 subtype of $GABA_A$. The general structure of formula I is shown below:

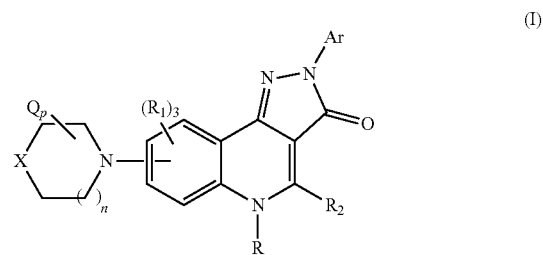

(I)

The compounds of Formula I encompass all possible tautomers of the chemical structures and mixtures thereof.
Embodiments, Aspects and Variations of the Invention It is recognized in the following structures, when a formula is depicted as a mixture of two tautomeric structures, that the definitions of "R" can be different in the structure on the left than in the structure on the right. For example, in a compound of formula (I), in the structure on the left the definition of "R" can be absent and in the structure on the right the definition of "R" can be hydrogen. Compounds represented by the tautomeric structures can exist in all possible tautomeric forms and mixtures thereof. Additionally, compounds need not exist in both drawn tautomeric forms. A compound that can be represented by either drawn structure, whether in equilibrium or not in equilibrium, falls within the present disclosure.

It is recognized, that two tautomeric forms are drawn for some formulas. For simplicity, in some places (including the claims), only the tautomeric form on the right is drawn for an indicated formula, this is not to exclude the other tautomeric form. In places where only one tautomeric form is drawn for a formula the other tautomeric form is also contemplated.

One embodiment of the invention provides a compound of formula (I):

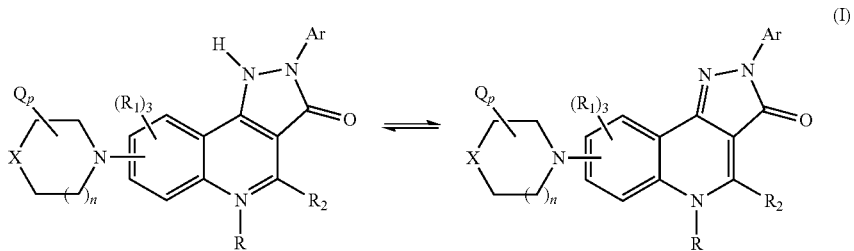

or tautomer thereof, or their pharmaceutically acceptable salts, wherein

R is absent, hydrogen, or oxide;

each $R_1$ is selected from the group consisting of hydrogen, hydroxy, halo, cyano, —$CONR_aR_b$, —$NR_aR_b$, hydroxy($C_1$-$C_6$)alkyl, aryl, heteroaryl, heterocycle, amino($C_1$-$C_6$)alkyl, ($C_1$-$C_6$)alkyl optionally substituted with up to 5 fluoro, and ($C_1$-$C_6$)alkoxy optionally substituted with up to 5 fluoro;

$R_2$ is selected from the group consisting of hydrogen, hydroxy, halo, hydroxy($C_1$-$C_6$)alkyl, ($C_1$-$C_6$)alkyl optionally substituted with up to 5 fluoro, and ($C_1$-$C_6$)alkoxy optionally substituted with up to 5 fluoro;

each $R_a$ and $R_b$ is independently hydrogen, ($C_1$-$C_6$)alkyl, aryl, heteroaryl, heterocycle, ($C_1$-$C_6$)alkylaryl, —$S(O)_z$($C_1$-$C_6$)alkyl, —$S(O)_z$aryl, —$C(O)(C_1$-$C_6$)alkyl, —$C(O)NR_g$($C_1$-$C_6$)alkyl, —$C(O)NR_g$aryl, —$C(O)O(C_1$-$C_6$)alkyl, arylOC(O)— or arylC(O)—, or $R_a$ together with $R_b$ form a heterocycle group optionally substituted with one or more $R_d$; wherein the heterocycle group optionally include one or more groups selected from O (oxygen), S (sulfur), and $NR_c$;

each $R_c$ is independently hydrogen, ($C_2$-$C_6$)alkenyl, ($C_2$-$C_6$)alkynyl, —$C(O)O(C_1$-$C_6$)alkyl, —$C(O)O$aryl, ($C_1$-$C_6$)alkoxy($C_1$-$C_6$)alkyl, hydroxy($C_1$-$C_6$)alkyl, aryl, heteroaryl, heterocycle, arylO($C_1$-$C_6$)alkyl, —$C(O)NR_g$($C_1$-$C_6$)alkyl, —$C(O)NR_g$aryl, —$S(O)_z$($C_1$-$C_6$)alkyl, —$S(O)_z$aryl, —$C(O)$($C_1$-$C_6$)alkyl, arylC(O)—, ($C_1$-$C_6$)alkyl optionally substituted with up to 5 fluoro, or ($C_1$-$C_6$)alkoxy optionally substituted with up to 5 fluoro;

each $R_d$ is independently selected from the group consisting of hydrogen, halo, oxo, hydroxy, —$C(O)NR_aR_b$, —$NR_aR_b$, hydroxy($C_1$-$C_6$)alkyl, aryl aryl($C_1$-$C_6$)alkyl, ($C_1$-$C_6$)alkyl optionally substituted with up to 5 fluoro, and ($C_1$-$C_6$)alkoxy optionally substituted with up to 5 fluoro;

each $R_e$ and $R_f$ is independently selected from hydrogen, ($C_1$-$C_6$)alkyl, aryl, heteroaryl, heterocycle, ($C_1$-$C_6$)alkylaryl, aryl($C_1$-$C_6$)alkyl, —$C(O)(C_1$-$C_6$)alkyl, —$S(O)_z$($C_1$-$C_6$)alkyl, —$S(O)_z NR_g$($C_1$-$C_6$)alkyl, —$S(O)_z$aryl, —$C(O)NR_g$($C_1$-$C_6$)alkyl, —$C(O)(C_1$-$C_6$)alkyl, arylC(O)—, arylOC(O)—, or —$C(O)O(C_1$-$C_6$)alkyl;

$R_g$ is hydrogen, aryl, heteroaryl, heterocycle or ($C_1$-$C_6$)alkyl optionally substituted with up to 5 fluoro;

Ar is aryl optionally substituted with one or more M or heteroaryl optionally substituted with one or more M;

each Q is independently hydrogen, halo, oxo, hydroxy, —$C(O)NR_aR_b$, —$NR_aR_b$, ($C_1$-$C_6$)alkyl optionally substituted with up to 5 fluoro, ($C_1$-$C_6$)alkoxy optionally substituted with up to 5 fluoro, ($C_1$-$C_6$)alkyl optionally substituted with one or more $R_d$, hydroxy($C_1$-$C_6$)alkyl optionally substituted with one or more $R_d$, aryl optionally substituted with one or more $R_d$, or aryl($C_1$-$C_6$)alkyl optionally substituted with one or more $R_d$;

each M is independently hydrogen, halo, $CF_3$, $CF_2H$, hydroxy, cyano, nitro, ($C_1$-$C_6$)alkyl, hydroxy($C_1$-$C_6$)alkyl, ($C_1$-$C_6$)alkoxy, —$NR_aR_b$, aryl, heteroaryl or heterocycle;

each X is independently NL, oxygen, $C(Q)_2$, or $S(O)_z$;

each L is independently hydrogen, ($C_2$-$C_6$)alkenyl, ($C_2$-$C_6$)alkynyl, —$C(O)O(C_1$-$C_6$)alkyl, —$C(O)O$aryl, ($C_1$-$C_6$)alkoxy($C_1$-$C_6$)alkyl, hydroxy($C_1$-$C_6$)alkyl, aryl, heteroaryl, heterocycle, arylO($C_1$-$C_6$)alkyl, —$CONR_eR_f$, —$S(O)_z$($C_1$-$C_6$)alkyl, —$S(O)_z$aryl, —$C(O)(C_1$-$C_6$)alkyl, arylC(O)—, —$C(O)NR_g$($C_1$-$C_6$)alkyl, ($C_1$-$C_6$)alkyl optionally substituted with up to 5 fluoro, or ($C_1$-$C_6$)alkoxy optionally substituted with up to 5 fluoro;

p is an integer selected from 0, 1, 2 and 3, z is an integer selected from 0, 1, and 2; and n is an integer selected from 0, 1, and 2.

In some embodiments, Ar can be:

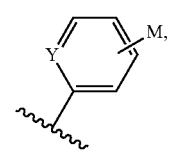

wherein Y is CM or N.

In another embodiment the compound has the formula Ia:

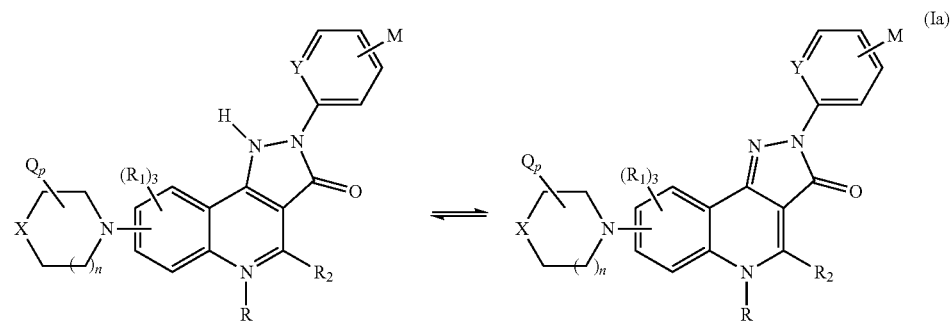

In another embodiment, the compound has the formula Ib:

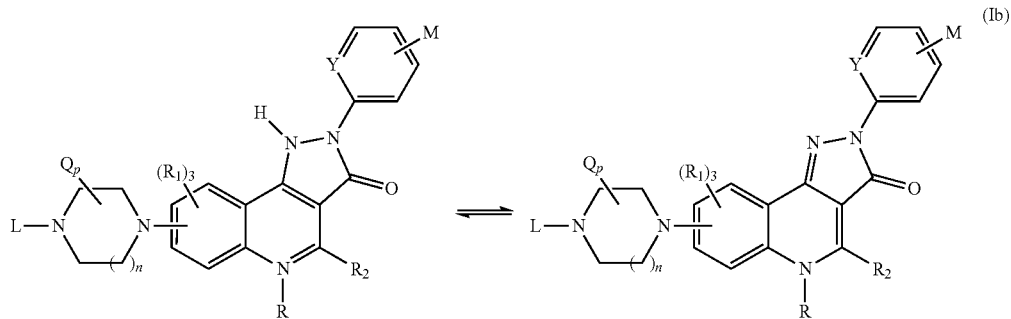

or tautomer thereof, or their pharmaceutically acceptable salts, wherein Y is CM or N.

In another embodiment, the compound has the formula Ic:

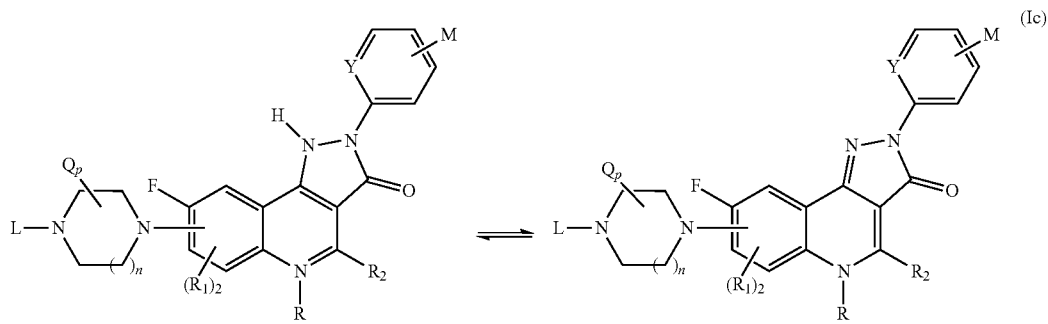

or tautomer thereof, or their pharmaceutically acceptable salts, wherein Y is CM or N.

In another embodiment, the compound has the formula Id:

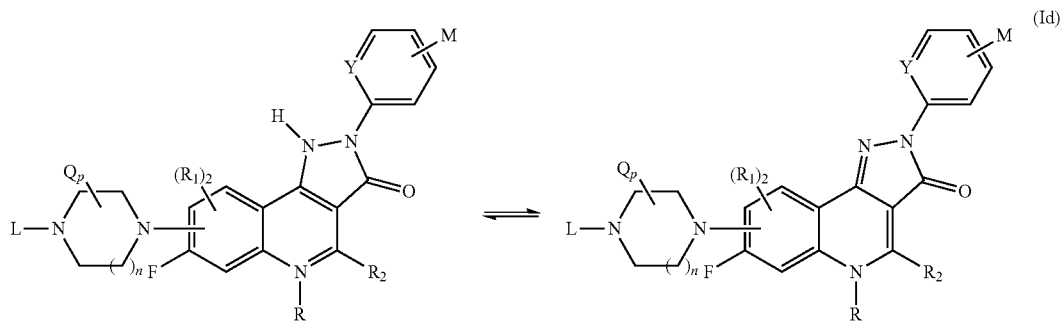

or tautomer thereof, or their pharmaceutically acceptable salts, wherein Y is CM or N.

In another embodiment, the compound has the formula Ie:

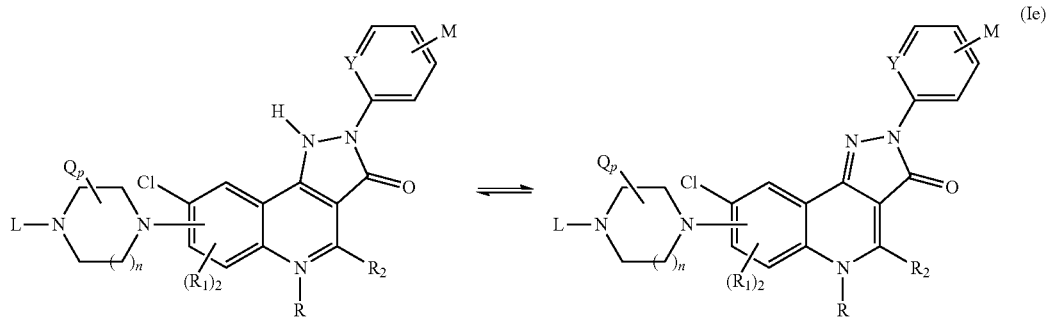

or tautomer thereof, or their pharmaceutically acceptable salts, wherein Y is CM or N.

In another embodiment, the compound has the formula If:

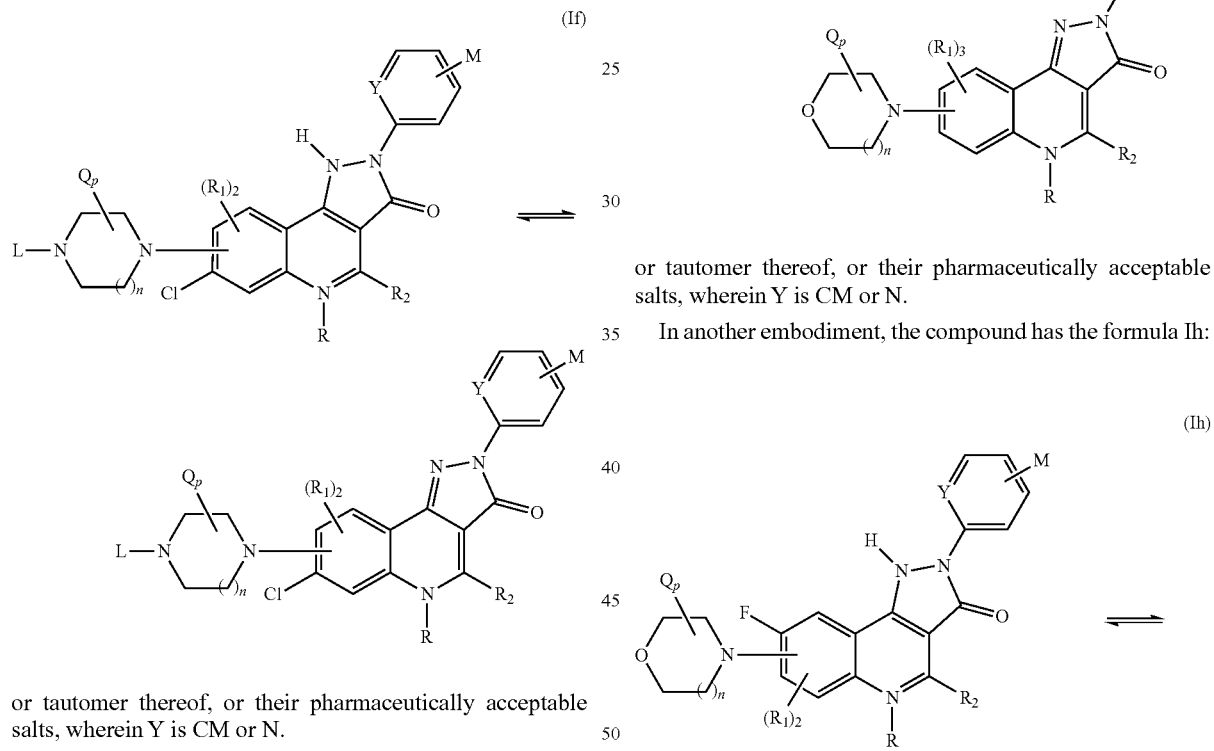

or tautomer thereof, or their pharmaceutically acceptable salts, wherein Y is CM or N.

In another embodiment, the compound has the formula Ig:

-continued or tautomer thereof, or their pharmaceutically acceptable salts, wherein Y is CM or N.

In another embodiment, the compound has the formula Ih:

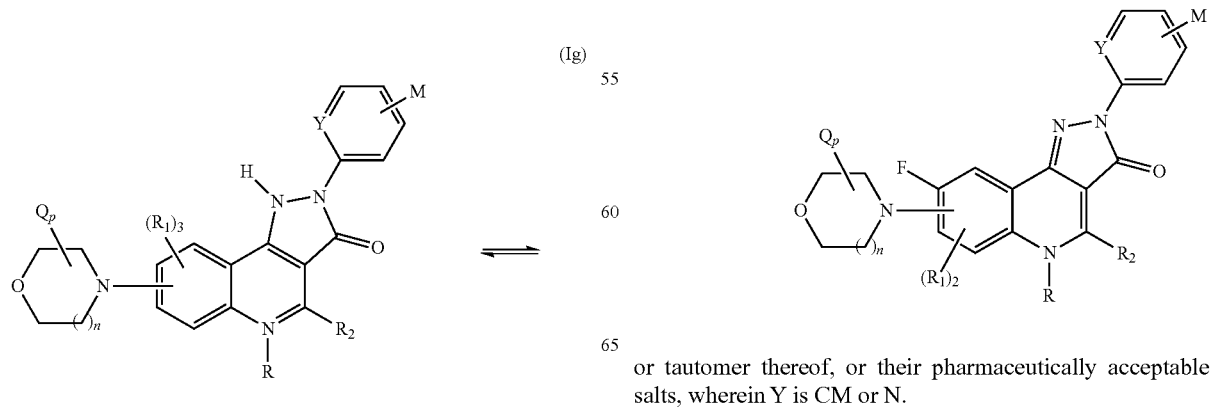

or tautomer thereof, or their pharmaceutically acceptable salts, wherein Y is CM or N.

In another embodiment, the compound has the formula Ii:

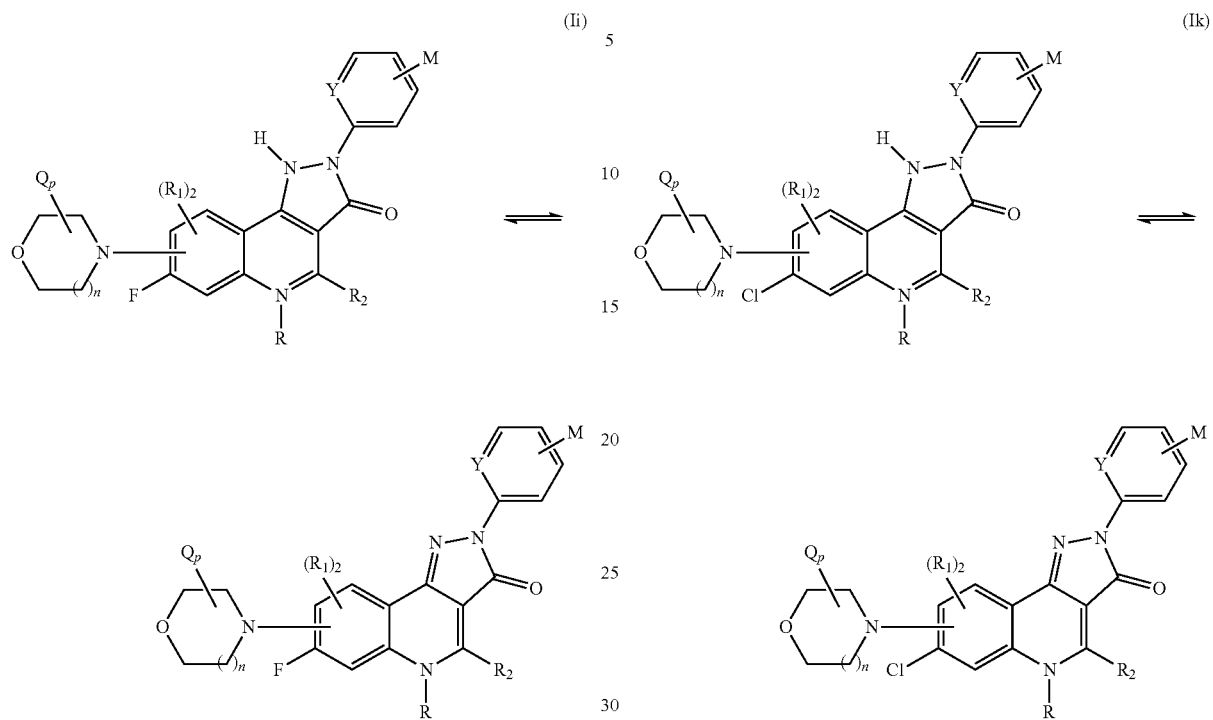

or tautomer thereof, or their pharmaceutically acceptable salts, wherein Y is CM or N.

In another embodiment, the compound has the formula Ij:

In another embodiment, the compound has the formula Ik:

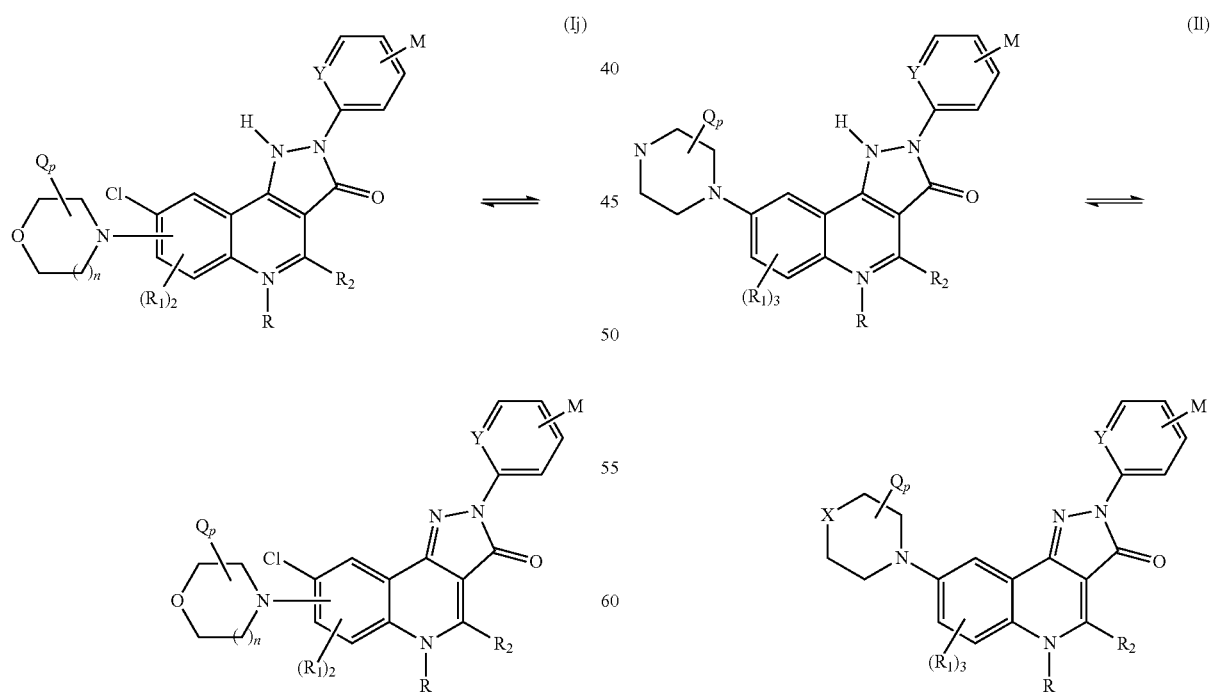

or tautomer thereof, or their pharmaceutically acceptable salts, wherein Y is CM or N.

In another embodiment, the compound has the formula Il:

or tautomer thereof, or their pharmaceutically acceptable salts, wherein Y is CM or N.

or tautomer thereof, or their pharmaceutically acceptable salts, wherein Y is CM or N.

In another embodiment, the compound has the formula Im:

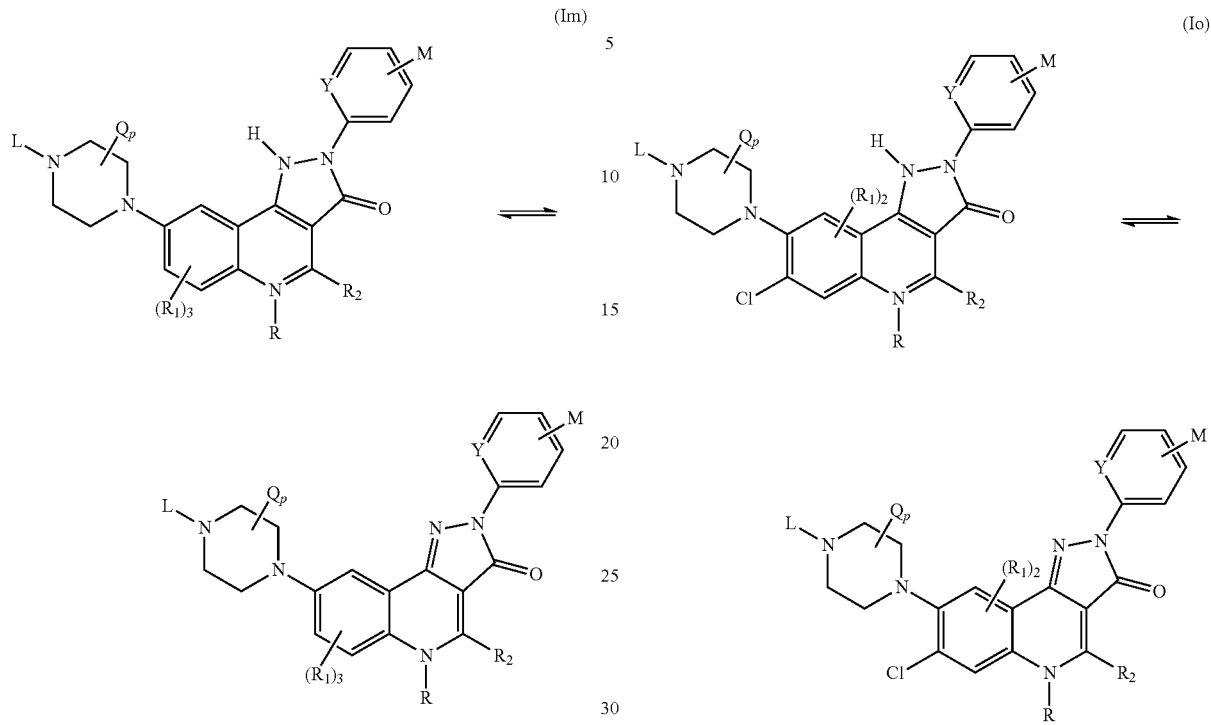

or tautomer thereof, or their pharmaceutically acceptable salts, wherein Y is CM or N.

In another embodiment, the compound has the formula In:

or tautomer thereof, or their pharmaceutically acceptable salts, wherein Y is CM or N.

In another embodiment, the compound has the formula Io:

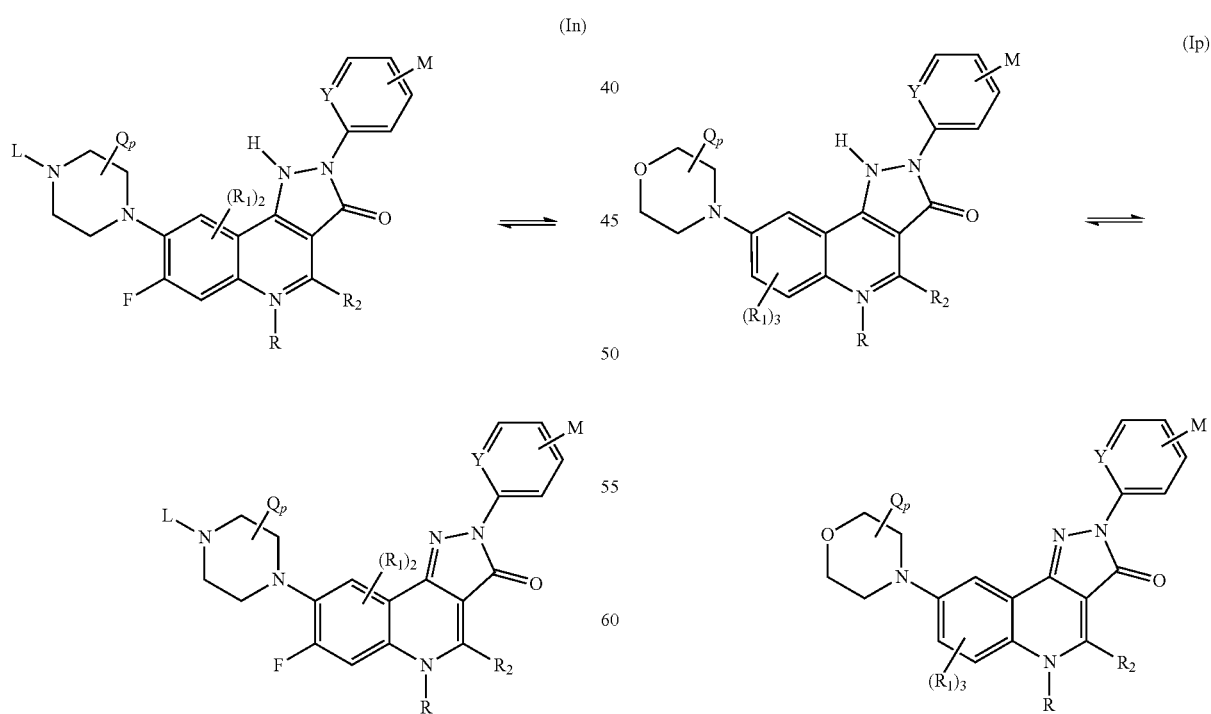

or tautomer thereof, or their pharmaceutically acceptable salts, wherein Y is CM or N.

In another embodiment, the compound has the formula Ip:

or tautomer thereof, or their pharmaceutically acceptable salts, wherein Y is CM or N.

or tautomer thereof, or their pharmaceutically acceptable salts, wherein Y is CM or N.

In another embodiment, the compound has the formula Iq:

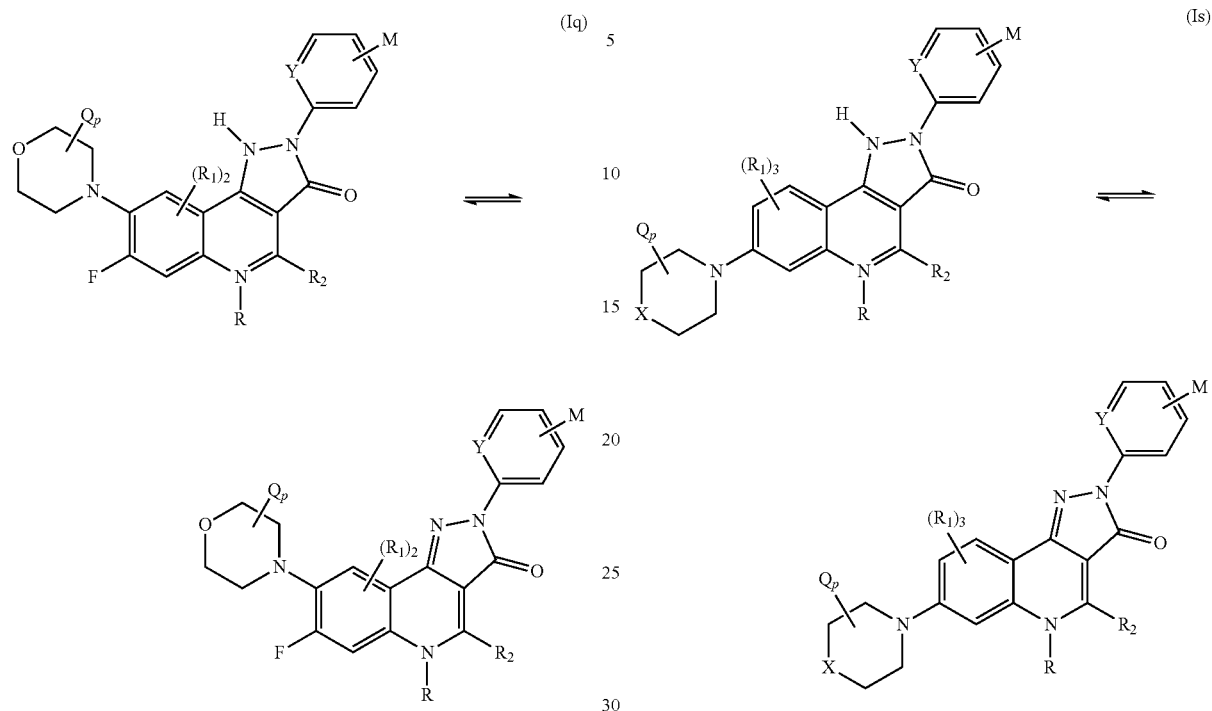

or tautomer thereof, or their pharmaceutically acceptable salts, wherein Y is CM or N.

In another embodiment, the compound has the formula Ir:

In another embodiment, the compound has the formula Is:

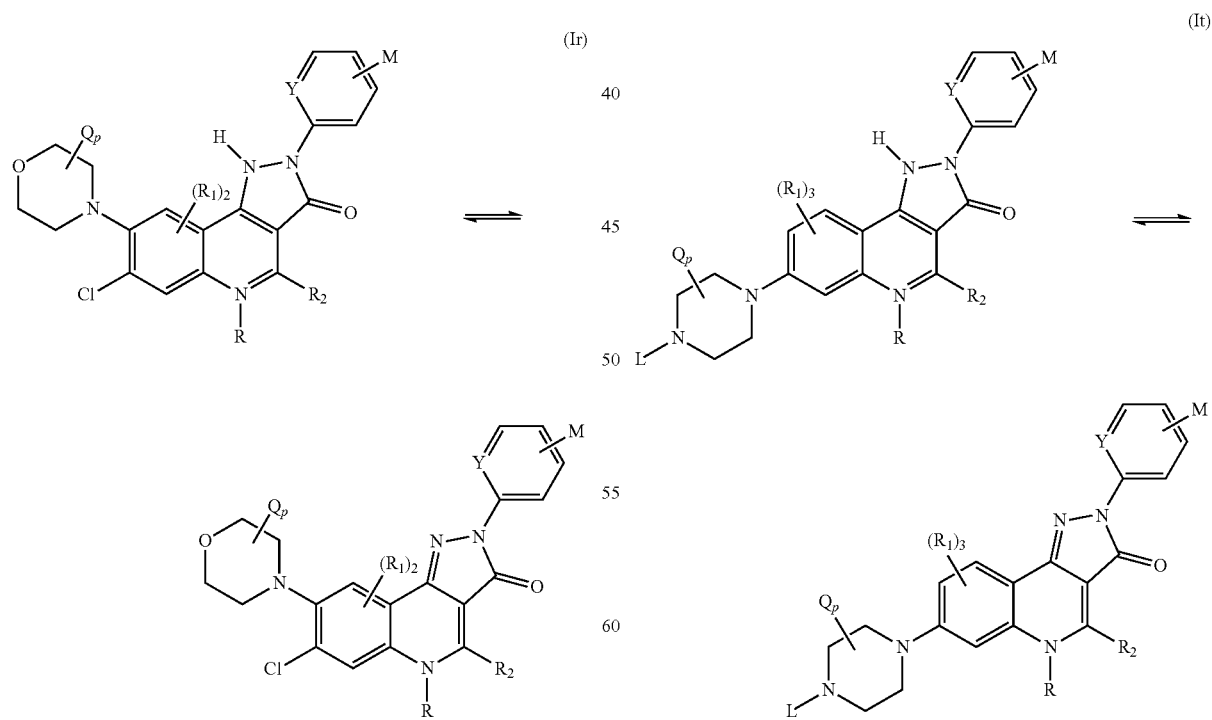

or tautomer thereof, or their pharmaceutically acceptable salts, wherein Y is CM or N.

In another embodiment, the compound has the formula It:

or tautomer thereof, or their pharmaceutically acceptable salts, wherein Y is CM or N.

or tautomer thereof, or their pharmaceutically acceptable salts, wherein Y is CM or N.

In another embodiment, the compound has the formula Iu:

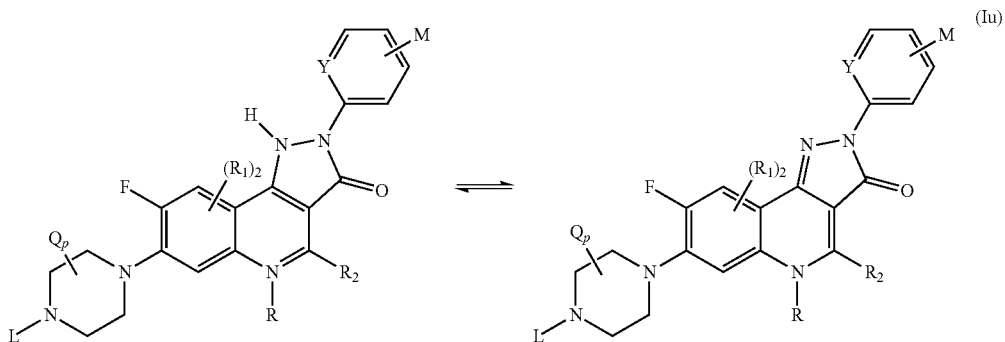

or tautomer thereof, or their pharmaceutically acceptable salts, wherein Y is CM or N.

In another embodiment, the compound has the formula Iv:

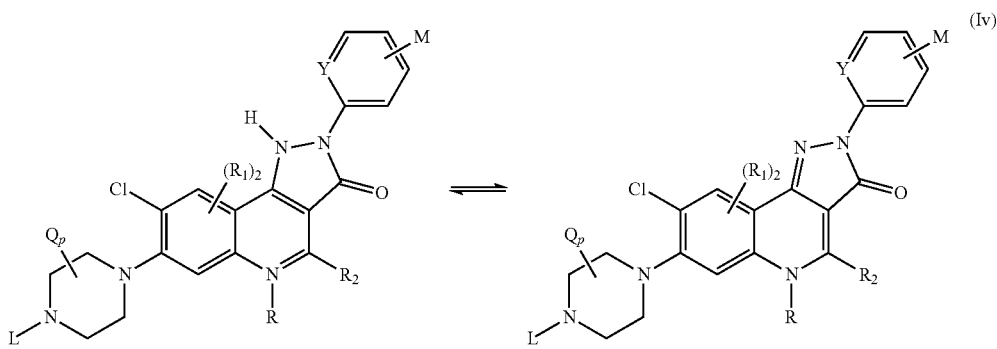

or tautomer thereof, or their pharmaceutically acceptable salts, wherein Y is CM or N.

In another embodiment, the compound has the formula Iw:

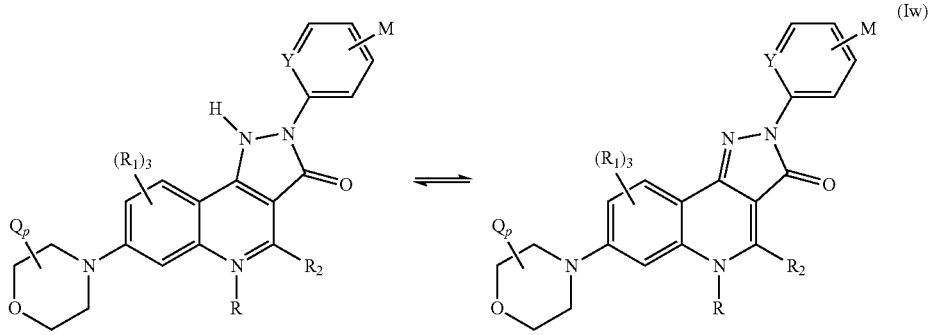

or tautomer thereof, or their pharmaceutically acceptable salts, wherein Y is CM or N.

In another embodiment, the compound has the formula Ix:

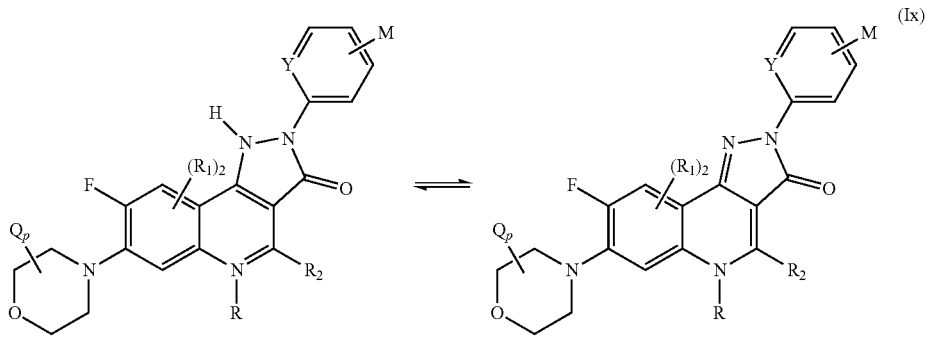

or tautomer thereof, or their pharmaceutically acceptable salts, wherein Y is CM or N.

In another embodiment, the compound has the formula Iy:

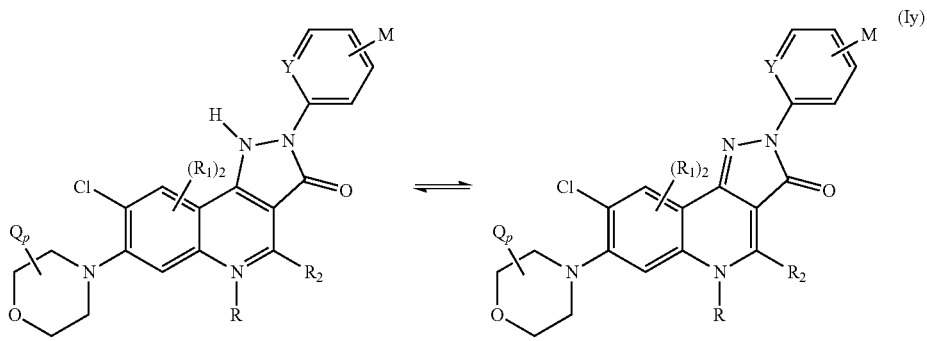

or tautomer thereof, or their pharmaceutically acceptable salts, wherein Y is CM or N.

In another embodiment, the compound has the formula Iz:

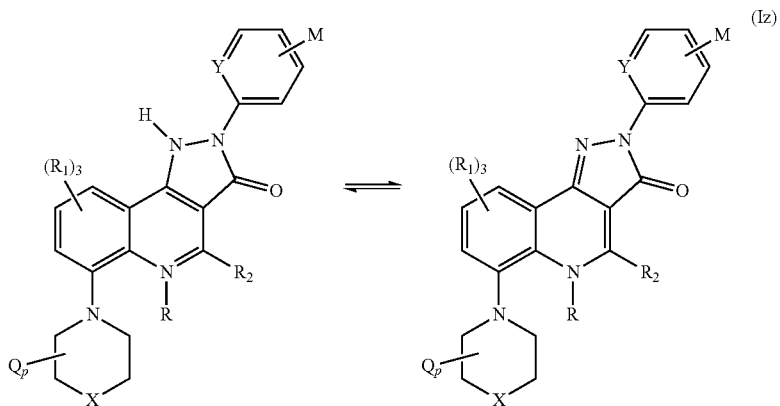

or tautomer thereof, or their pharmaceutically acceptable salts, wherein Y is CM or N.

In another embodiment, the compound has the formula Iaa:

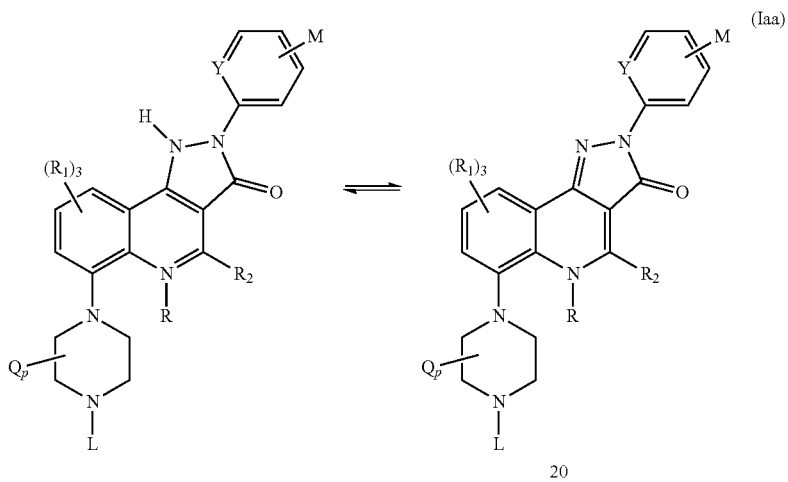

or tautomer thereof, or their pharmaceutically acceptable salts, wherein Y is CM or N.

In another embodiment, the compound has the formula Iab:

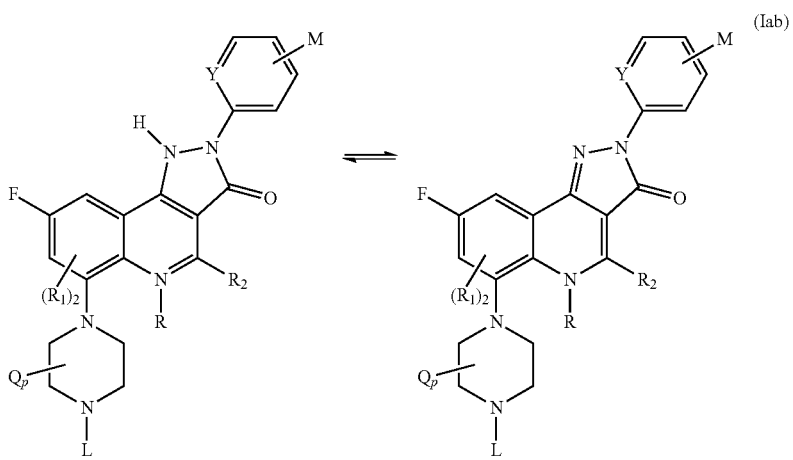

or tautomer thereof, or their pharmaceutically acceptable salts, wherein Y is CM or N.

In another embodiment, the compound has the formula Iac:

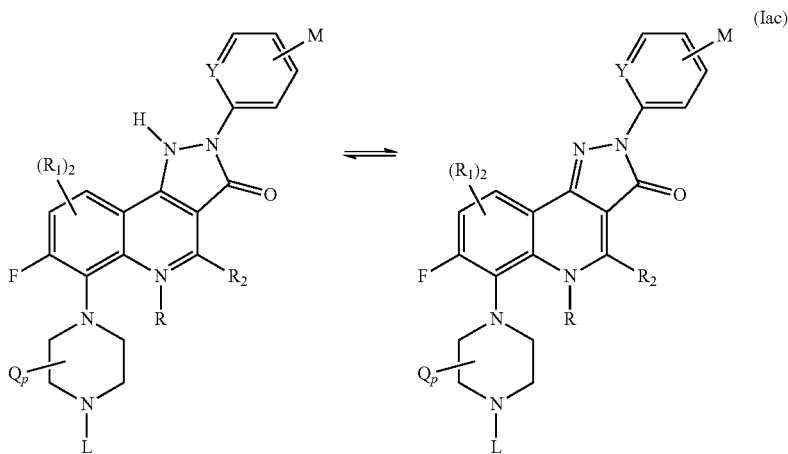

or tautomer thereof, or their pharmaceutically acceptable salts, wherein Y is CM or N.

In another embodiment, the compound has the formula Iad:

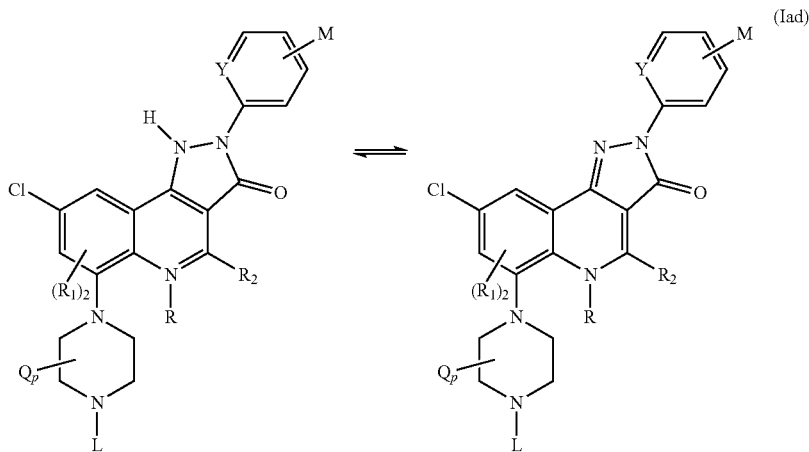

or tautomer thereof, or their pharmaceutically acceptable salts, wherein Y is CM or N.

In another embodiment, the compound has the formula Iae:

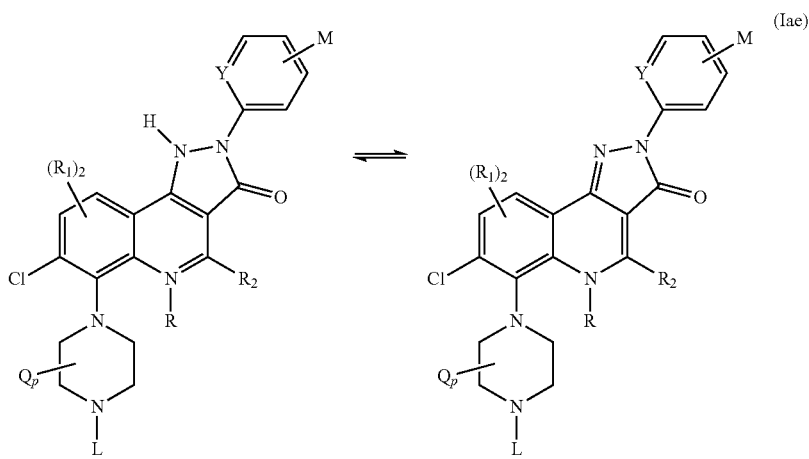

or tautomer thereof, or their pharmaceutically acceptable salts, wherein Y is CM or N.

In another embodiment, the compound has the formula Iaf:

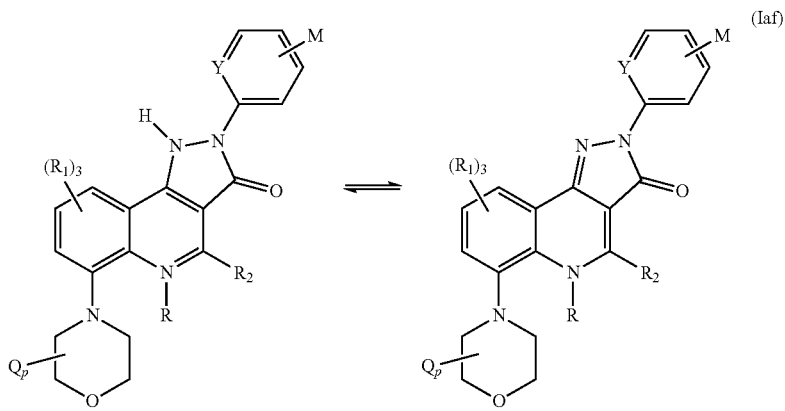

or tautomer thereof, or their pharmaceutically acceptable salts, wherein Y is CM or N.

In another embodiment, the compound has the formula Iag:

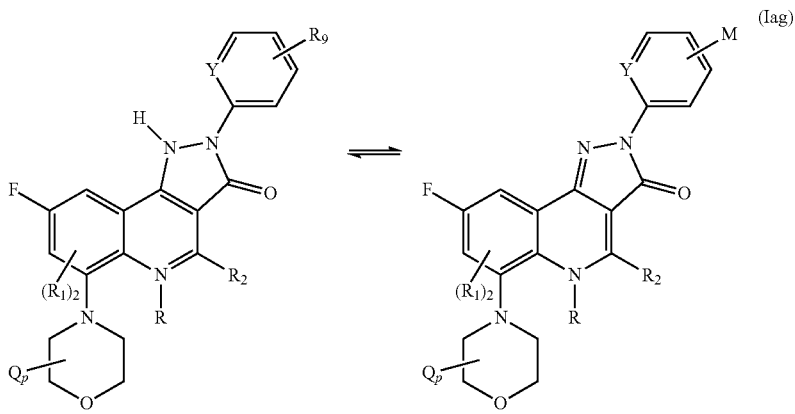

or tautomer thereof, or their pharmaceutically acceptable salts, wherein Y is CM or N.

In another embodiment, the compound has the formula Iah:

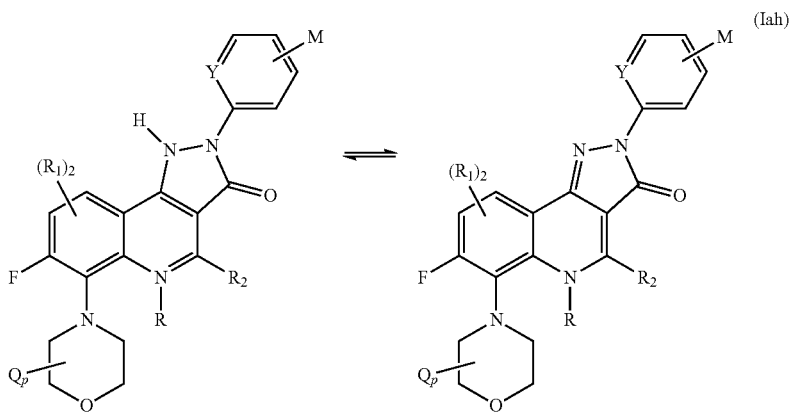

or tautomer thereof, or their pharmaceutically acceptable salts, wherein Y is CM or N.

In another embodiment, the compound has the formula Iaj:

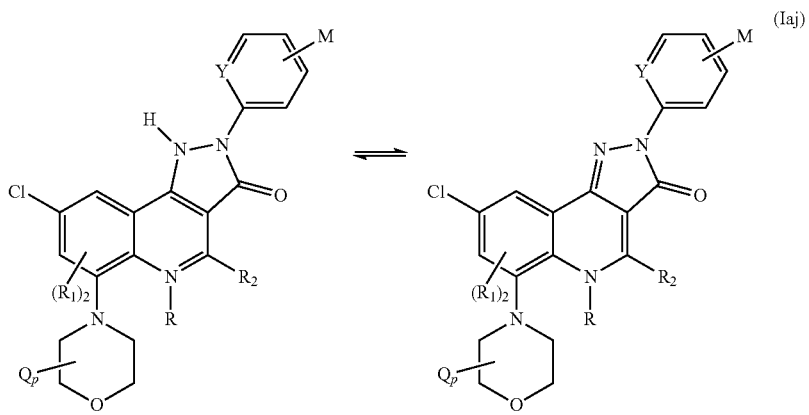

or tautomer thereof, or their pharmaceutically acceptable salts, wherein Y is CM or N.

In another embodiment, the compound has the formula Iak:
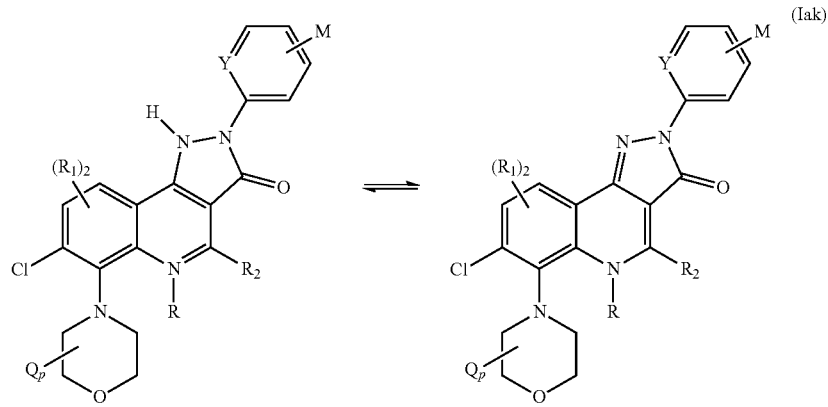
or tautomer thereof, or their pharmaceutically acceptable salts, wherein Y is CM or N.
In another embodiment, the compound is selected from the group consisting of
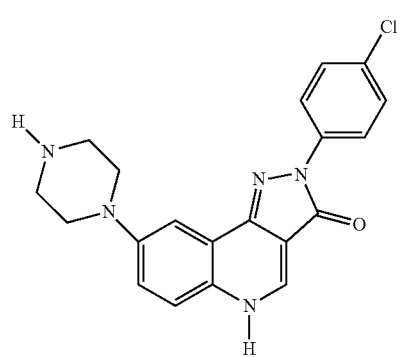
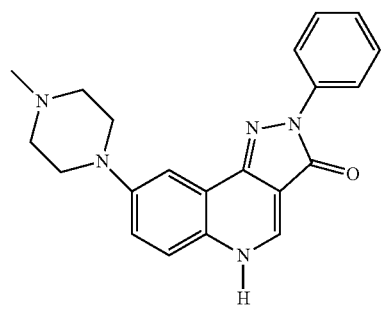
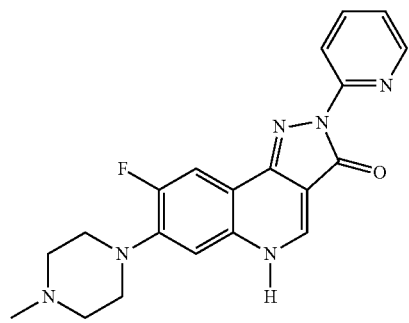
-continued
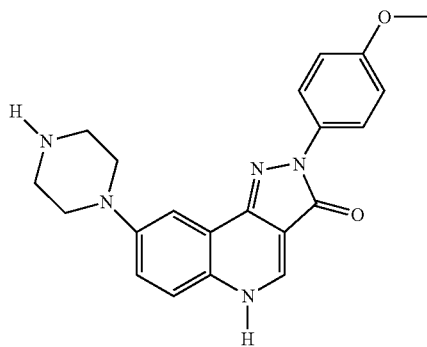
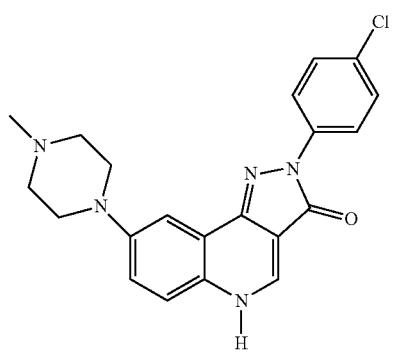
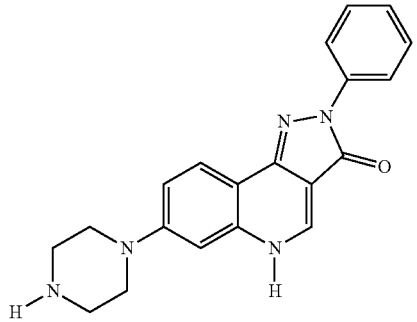

27
-continued
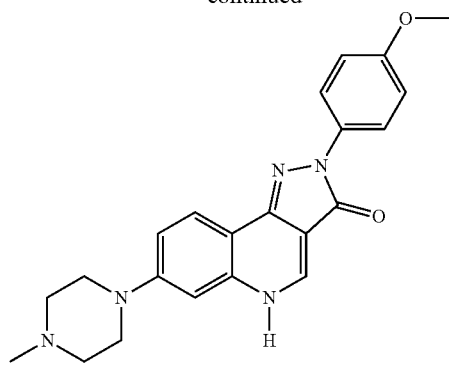
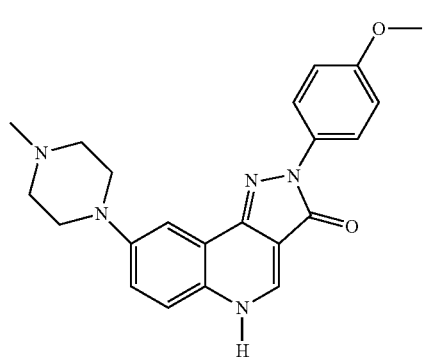
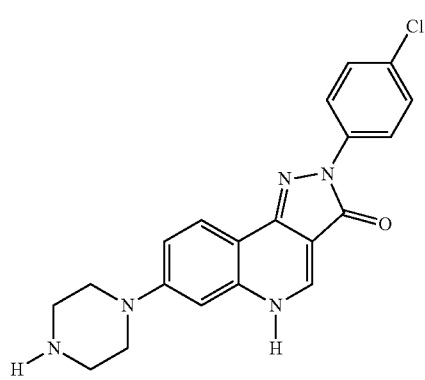
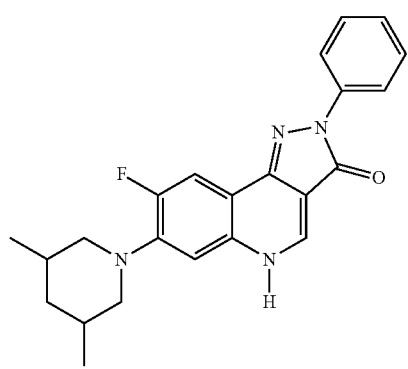
28
-continued
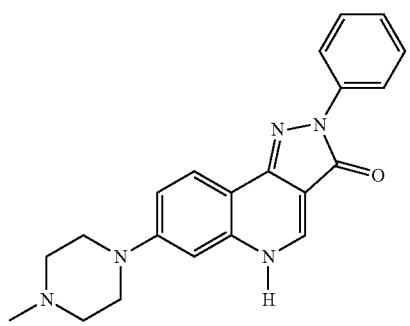
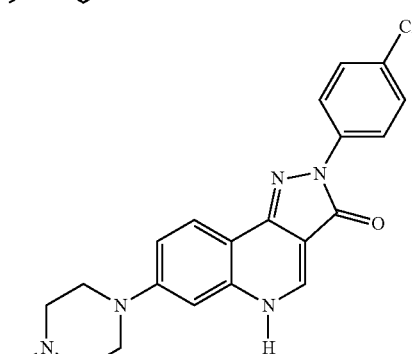
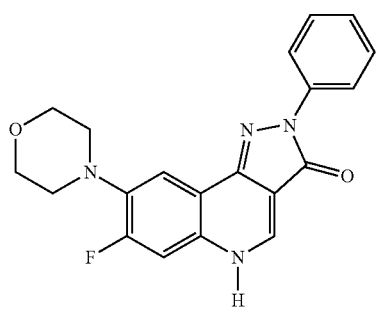
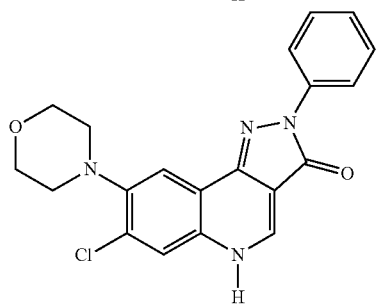
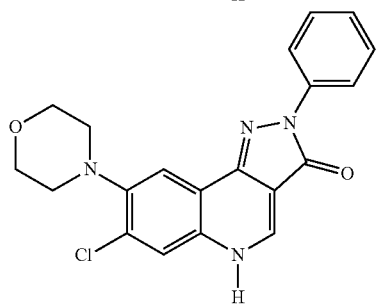

29
-continued
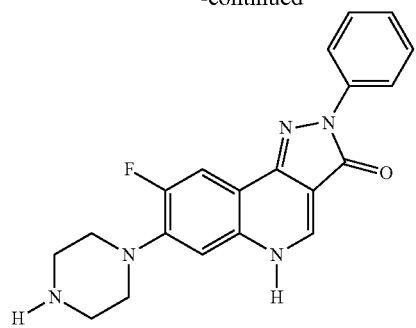
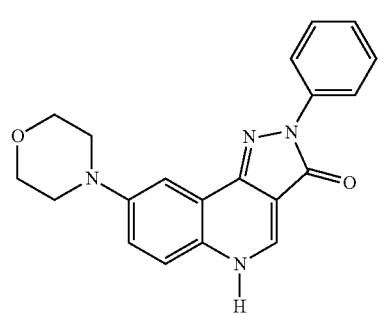
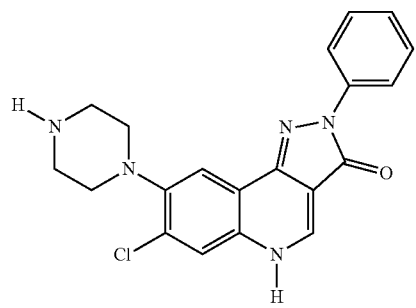
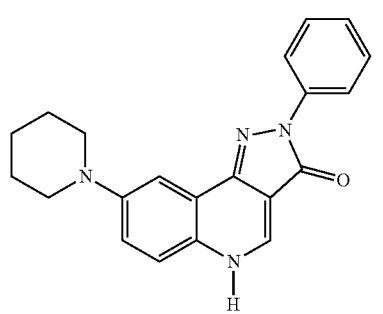
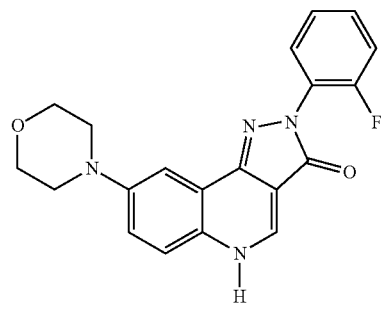
30
-continued
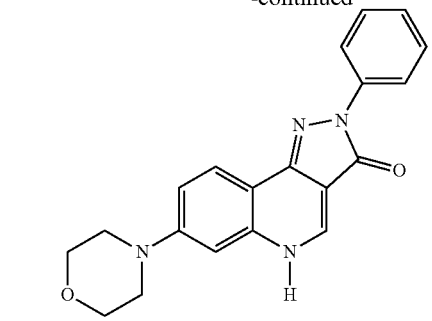
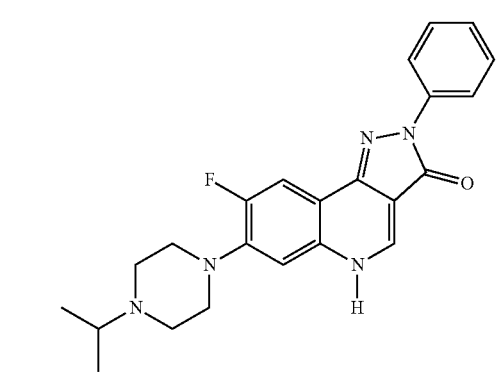
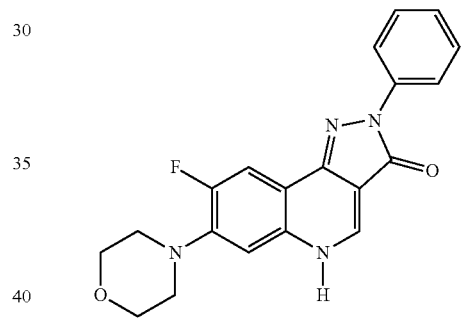
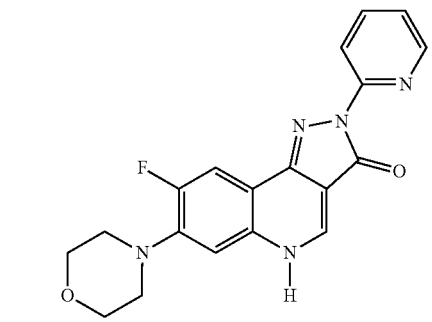
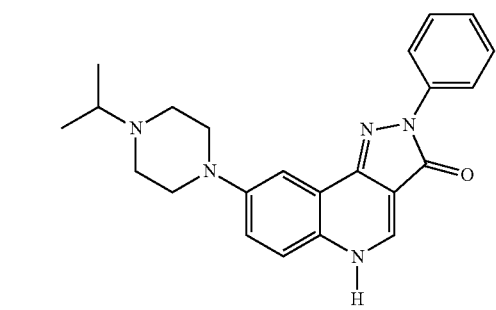

31
-continued
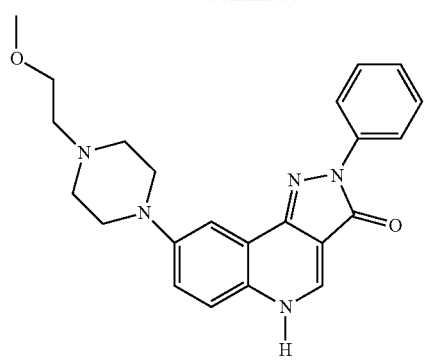
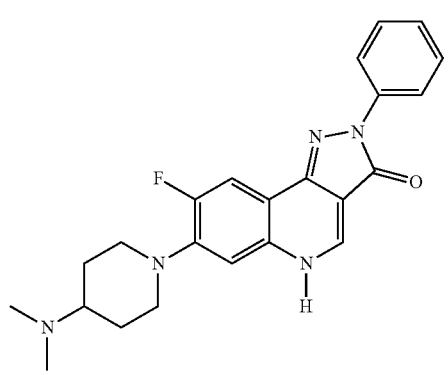
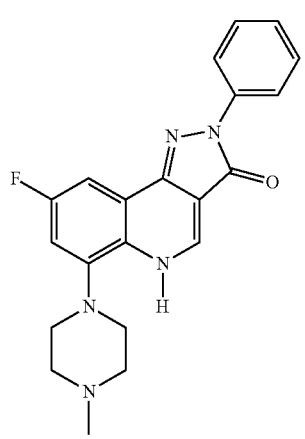
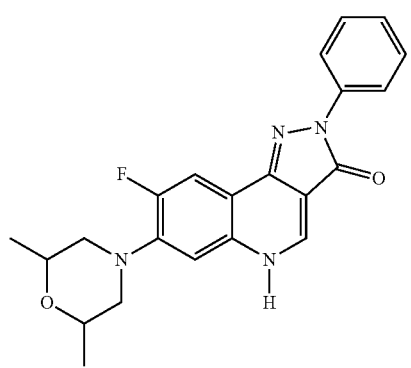
32
-continued
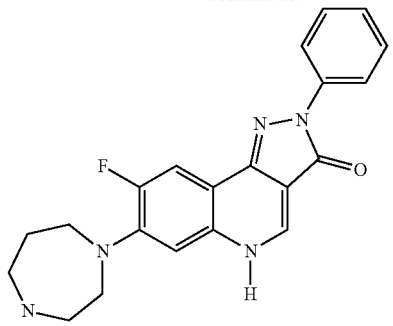
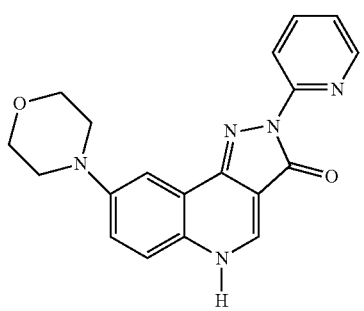
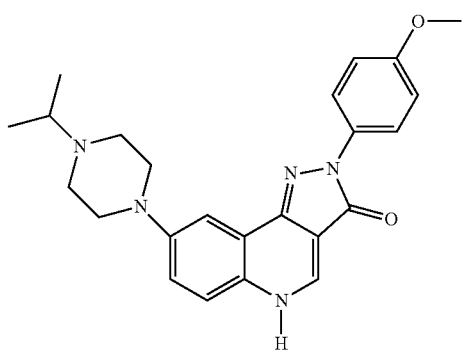
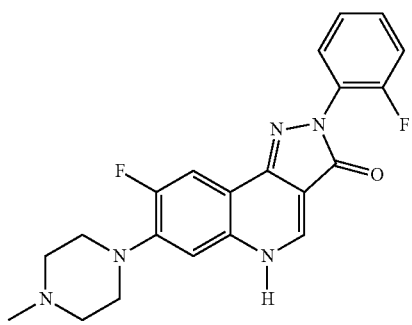
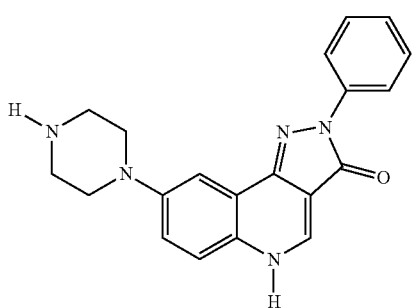

33
-continued
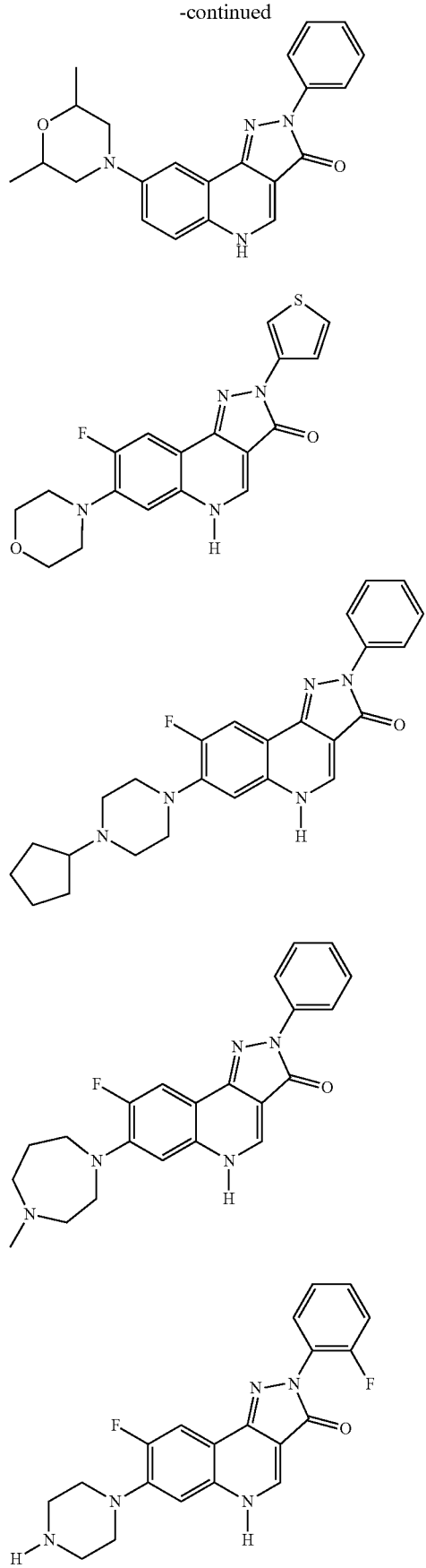
34
-continued
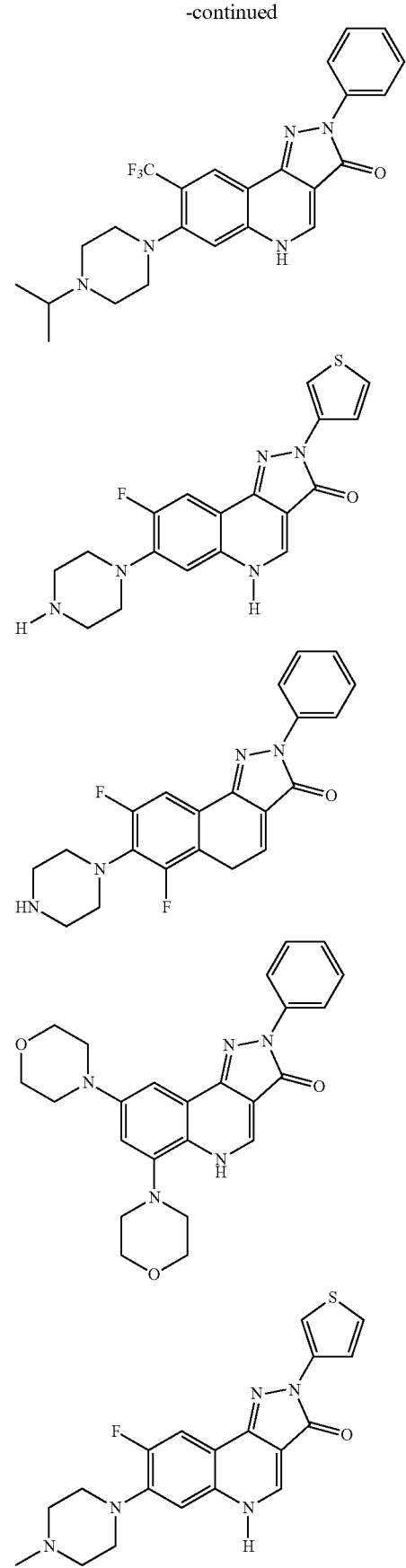

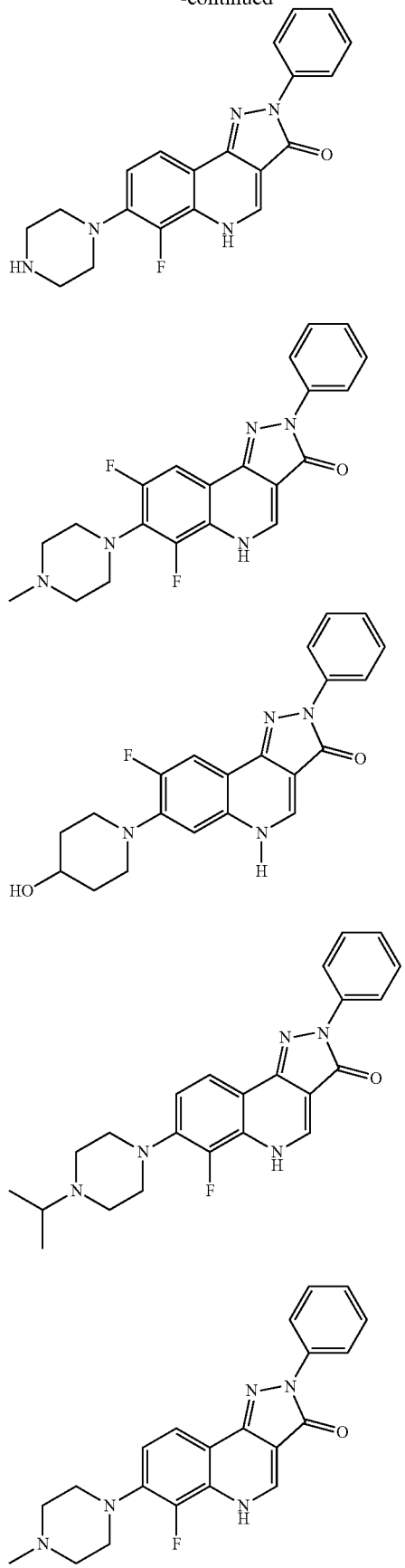
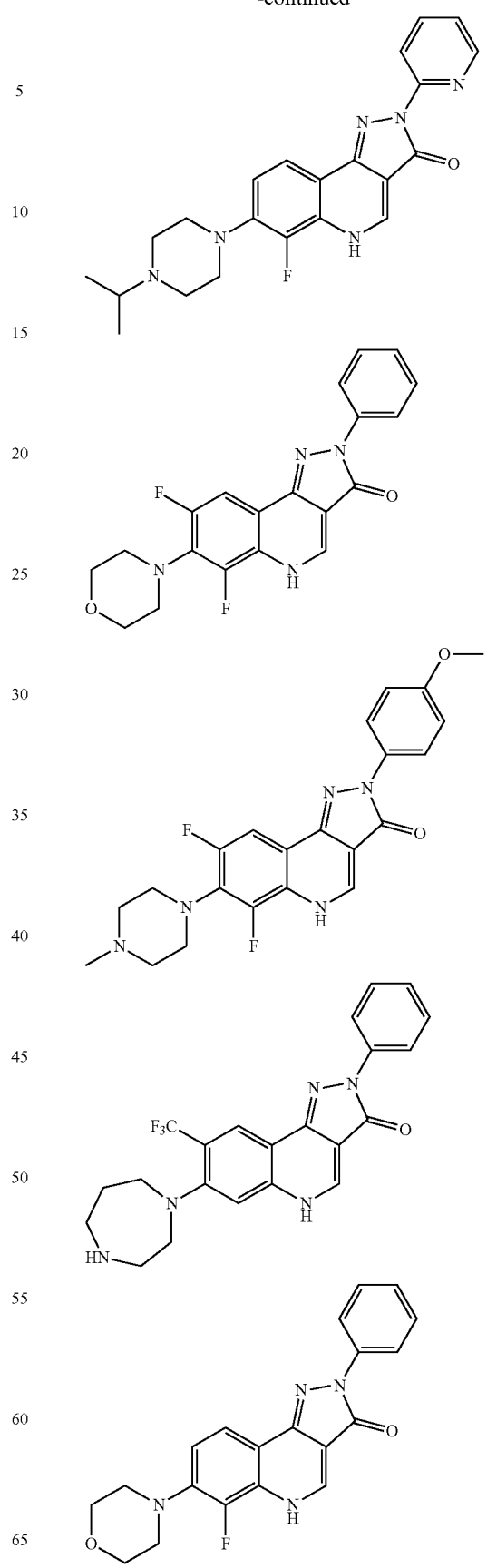

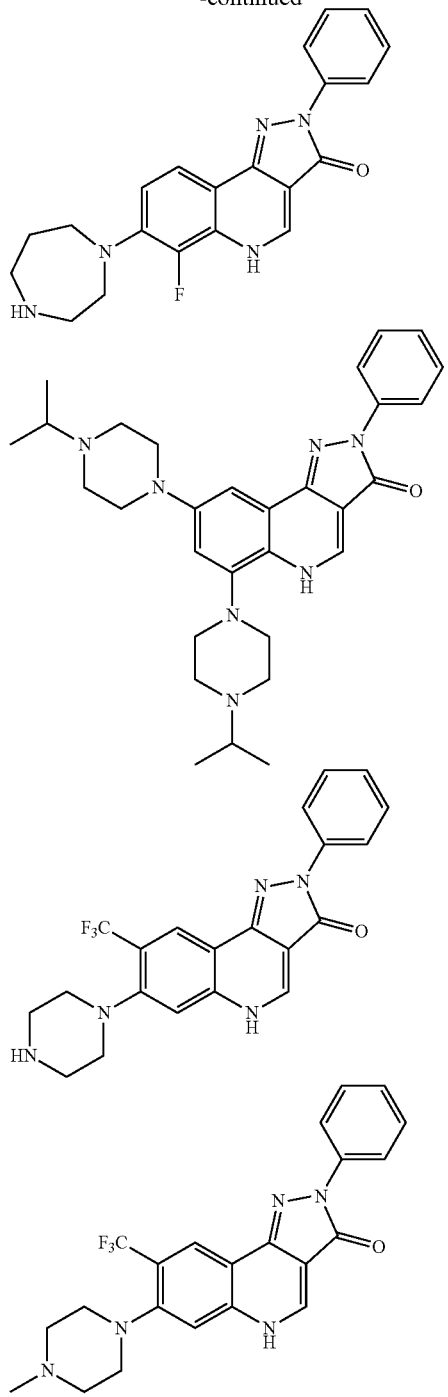
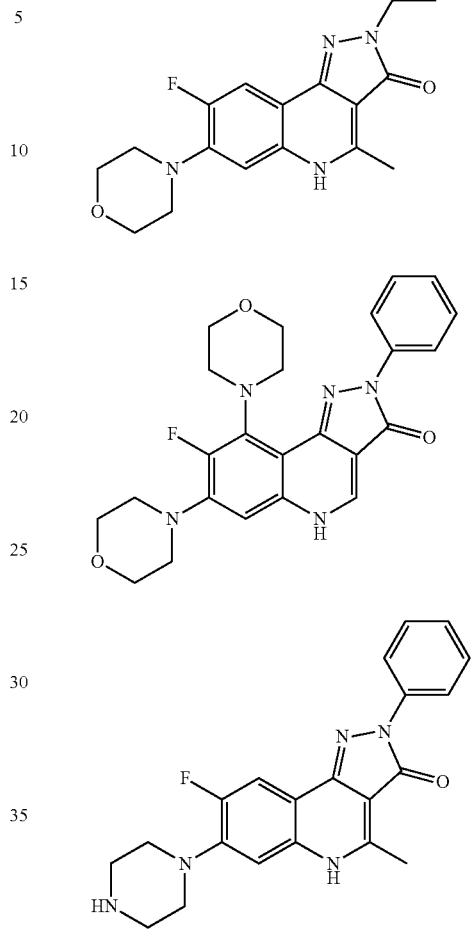

or tautomer thereof, or their pharmaceutically acceptable salts.

One embodiment of the invention provides a pharmaceutical composition comprising:

a) the compound of any of the embodiments and examples disclosed herein; and b) a pharmaceutically acceptable carrier.

The present embodiments provide for a method of modulating one or more GABA$_A$ subtypes in an animal comprising administering to the animal an effective amount of a compound, including enantiomers or diastereomers thereof, of formula (I):

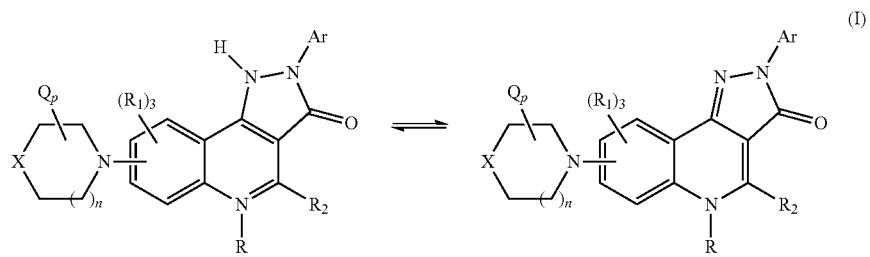

or tautomer thereof, or their pharmaceutically acceptable salts,

R is absent, hydrogen, or oxide;

each $R_1$ is selected from the group consisting of hydrogen, hydroxy, halo, cyano, —$CONR_aR_b$, —$NR_aR_b$, hydroxy($C_1$-$C_6$)alkyl, aryl, heteroaryl, heterocycle, amino($C_1$-$C_6$)alkyl, ($C_1$-$C_6$)alkyl optionally substituted with up to 5 fluoro, and ($C_1$-$C_6$)alkoxy optionally substituted with up to 5 fluoro;

$R_2$ is selected from the group consisting of hydrogen, hydroxy, halo, hydroxy($C_1$-$C_6$)alkyl, ($C_1$-$C_6$)alkyl optionally substituted with up to 5 fluoro, and ($C_1$-$C_6$)alkoxy optionally substituted with up to 5 fluoro;

each $R_a$ and $R_b$ is independently hydrogen, ($C_1$-$C_6$)alkyl, aryl, heteroaryl, heterocycle, ($C_1$-$C_6$)alkylaryl, —$S(O)_z(C_1$-$C_6$)alkyl, —$S(O)_z$aryl, —$C(O)(C_1$-$C_6$)alkyl, —$C(O)NR_g$($C_1$-$C_6$)alkyl, —$C(O)NR_g$aryl, —$C(O)O(C_1$-$C_6$)alkyl, arylOC(O)— or arylC(O)—, or $R_a$ together with $R_b$ form a heterocycle group optionally substituted with one or more $R_d$; wherein the heterocycle group optionally include one or more groups selected from O (oxygen), S (sulfur), and $NR_c$;

each $R_c$ is independently hydrogen, ($C_2$-$C_6$)alkenyl, ($C_2$-$C_6$)alkynyl, —$C(O)O(C_1$-$C_6$)alkyl, —$C(O)O$aryl, ($C_1$-$C_6$)alkoxy($C_1$-$C_6$)alkyl, hydroxy($C_1$-$C_6$)alkyl, aryl, heteroaryl, heterocycle, arylO($C_1$-$C_6$)alkyl, —$C(O)NR_g(C_1$-$C_6$)alkyl, —$C(O)NR_g$aryl, —$S(O)_z(C_1$-$C_6$)alkyl, —$S(O)_z$aryl, —$C(O)(C_1$-$C_6$)alkyl, arylC(O)—, ($C_1$-$C_6$)alkyl optionally substituted with up to 5 fluoro, or ($C_1$-$C_6$)alkoxy optionally substituted with up to 5 fluoro;

each $R_d$ is independently selected from the group consisting of hydrogen, halo, oxo, hydroxy, —$C(O)NR_aR_b$, —$NR_aR_b$, hydroxy($C_1$-$C_6$)alkyl, aryl aryl($C_1$-$C_6$)alkyl, ($C_1$-$C_6$)alkyl optionally substituted with up to 5 fluoro, and ($C_1$-$C_6$)alkoxy optionally substituted with up to 5 fluoro;

each $R_e$ and $R_f$ is independently selected from hydrogen, ($C_1$-$C_6$)alkyl, aryl, heteroaryl, heterocycle, ($C_1$-$C_6$)alkylaryl, aryl($C_1$-$C_6$)alkyl, —$C(O)(C_1$-$C_6$)alkyl, —$S(O)_z(C_1$-$C_6$)alkyl, —$S(O)_zNR_g(C_1$-$C_6$)alkyl, —$S(O)_z$aryl, —$C(O)NR_g$($C_1$-$C_6$)alkyl, —$C(O)(C_1$-$C_6$)alkyl, arylC(O)—, arylOC(O)—, or —$C(O)O(C_1$-$C_6$)alkyl;

$R_g$ is hydrogen, aryl, heteroaryl, heterocycle or ($C_1$-$C_6$) alkyl optionally substituted with up to 5 fluoro;

Ar is aryl optionally substituted with one or more M or heteroaryl optionally substituted with one or more M;

each Q is independently hydrogen, halo, oxo, hydroxy, —$C(O)NR_aR_b$, —$NR_aR_b$, ($C_1$-$C_6$)alkyl optionally substituted with up to 5 fluoro, ($C_1$-$C_6$)alkoxy optionally substituted with up to 5 fluoro, ($C_1$-$C_6$)alkyl optionally substituted with one or more $R_d$, hydroxy($C_1$-$C_6$)alkyl optionally substituted with one or more $R_d$, aryl optionally substituted with one or more $R_d$, or aryl($C_1$-$C_6$)alkyl optionally substituted with one or more $R_d$;

each M is independently hydrogen, halo, $CF_3$, $CF_2H$, hydroxy, cyano, nitro, ($C_1$-$C_6$)alkyl, hydroxy($C_1$-$C_6$)alkyl, ($C_1$-$C_6$)alkoxy, —$NR_aR_b$, aryl, heteroaryl or heterocycle;

each X is independently NL, oxygen, $C(Q)_2$, or $S(O)_z$;

each L is independently hydrogen, ($C_2$-$C_6$)alkenyl, ($C_2$-$C_6$)alkynyl, —$C(O)O(C_1$-$C_6$)alkyl, —$C(O)O$aryl, ($C_1$-$C_6$)alkoxy($C_1$-$C_6$)alkyl, hydroxy($C_1$-$C_6$)alkyl, aryl, heteroaryl, heterocycle, arylO($C_1$-$C_6$)alkyl, —$CONR_eR_f$, —$S(O)_z(C_1$-$C_6$)alkyl, —$S(O)_z$aryl, —$C(O)(C_1$-$C_6$)alkyl, arylC(O)—, —$C(O)NR_g(C_1$-$C_6$)alkyl, ($C_1$-$C_6$)alkyl optionally substituted with up to 5 fluoro, or ($C_1$-$C_6$)alkoxy optionally substituted with up to 5 fluoro;

p is an integer selected from 0, 1, 2 and 3, z is an integer selected from 0, 1, and 2; and n is an integer selected from 0, 1, and 2.

In one embodiment of the method, the modulation is negative. In another embodiment, the modulation is positive. In one embodiment of the method, the $GABA_A$ subtypes is $GABA_A$ α5. In one embodiment of the method, the modulation is negative. In another embodiment, the modulation is positive.

Some embodiments disclosed herein relate to a method of treatment of a cognitive dysfunction in an animal comprising administering to the animal an effective amount of a compound of formula (I), and tautomers thereof, or their pharmaceutically acceptable salts, under conditions wherein the cognitive dysfunction is treated. In one embodiment, the animal is an aged animal. In another embodiment, the cognitive dysfunction is Alzheimer's disease, dementia or another neurodegenerative disease.

Some embodiments disclosed herein relate to a method of treatment of a psychiatric disorder in an animal comprising administering to the animal an effective amount of a compound of formula (I), and tautomers thereof, or their pharmaceutically acceptable salts, under conditions wherein the psychiatric disorder is treated.

Some embodiments disclosed herein relate to the use of a compound of formula (I), and tautomers thereof, or their pharmaceutically acceptable salts, for the manufacture of a medicament useful for modulation of one or more $GABA_A$ subtypes in an animal. In one embodiment of the method, the modulation is negative. In another embodiment, the modulation is positive. In one embodiment of the method, the $GABA_A$ subtypes is $GABA_A$ α5. In one embodiment of the method, the modulation is negative. In another embodiment, the modulation is positive.

Some embodiments disclosed herein relate to the use of a compound of formula (I), and tautomers thereof, or their pharmaceutically acceptable salts, for the manufacture of a medicament useful for treatment of a cognitive dysfunction in an animal. In one embodiment, the animal is a healthy animal. In another embodiment, the animal is an aged animal. In another embodiment, the cognitive dysfunction is Alzheimer's disease, dementia or another neurodegenerative disease.

Some embodiments disclosed herein relate to the use of a compound of formula (I), and tautomers thereof, or their pharmaceutically acceptable salts, for the manufacture of a medicament useful for treatment of psychiatric disorders in an animal. In one embodiment the psychiatric disorder is an anxiety disorder, sleep disorder, depression, or schizophrenia.

Some embodiments disclosed herein relate to the use of a compound of formula (I), and tautomers thereof, or their pharmaceutically acceptable salts, for the manufacture of a medicament useful for treatment of disorders ameliorated by modulation of $GABA_A$ α subunits other than α5 in an animal. In one embodiment, the modulation is positive. In another embodiment, the modulation is negative.

Some embodiments disclosed herein relate to a method for treating cognitive impairment resulting from diseases such as schizophrenia, Alzheimer's, Parkinson's, Pick's, Huntington's, and Creutzfeld-Jakob along with other forms of dementia, MCI, AAMI, and delirium.

One embodiment provides the use of compounds not specifically inverse agonists of α5 for other CNS disorders, such as anxiety.

Some embodiments disclosed herein relate to a method of increasing cognitive function in an animal comprising administering to the animal an effective amount of a compound of formula (I), or a pharmaceutically acceptable salt thereof, under conditions wherein memory is increased. In one embodiment, the animal is healthy. In one embodiment, the memory is long term memory. In one embodiment, the memory is short term memory.

Some embodiments disclosed herein relate to the use of a compound of formula (I), or a pharmaceutically acceptable salt thereof, for the manufacture of a medicament for increasing cognitive function in an animal wherein the $GABA_A$ α5 subtype in the animal is negatively modulated. In one embodiment, the animal is healthy. In one embodiment, the memory is long term memory. In one embodiment, the memory is short term memory.

DETAILED DESCRIPTION OF THE INVENTION

Definitions

As use herein, common organic abbreviations are defined as follows:

| | |
|---|---|
| Ac | Acetyl |
| aq. | Aqueous |
| Bu | n-Butyl |
| cat. | Catalytic |
| CDI | 1,1'-carbonyldiimidazole |
| ° C. | Temperature in degrees Centigrade |
| Dowtherm ® | eutectic mixture of diphenyl ether and biphenyl |
| DBN | 1,5-Diazabicyclo[4.3.0]non-5-ene |
| DBU | 1,8-Diazabicyclo[5.4.0]undec-7-ene |
| DIEA | Diisopropylethylamine |
| DMA | Dimethylacetamide |
| DMF | N,N'-Dimethylformamide |
| DMSO | Dimethylsulfoxide |
| Et | Ethyl |
| g | Gram(s) |
| h | Hour (hours) |
| HPLC | High performance liquid chromatography |
| iPr or isopr | Isopropyl |
| LCMS | Liquid chromatography-mass spectrometry |
| Me | Methyl |
| MeOH | Methanol |
| mL | Milliliter(s) |
| Pd/C | Palladium on activated carbon |
| ppt | Precipitate |
| rt | Room temperature |
| TEA | Triethylamine |
| Tert, t | tertiary |
| μL | Microliter(s) |

The term "halo" used herein refers to fluoro, chloro, bromo, or iodo.

As used herein, the term "alkyl" refers to an aliphatic hydrocarbon group. The alkyl moiety may be a "saturated alkyl" group, which means that it does not contain any alkene or alkyne moieties. An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety may be branched, straight chain, or cyclic. Examples of branched alkyl groups include, but are not limited to, isopropy, sec-butyl, t-butyl and the like. Examples of straight chain alkyl groups include, but are not limited to, methyl, ethyl, propyl, butyl, pentyl, hexyl, heptyl, and the like. Examples of cyclic alkyl groups include, but are not limited to, cyclopropyl, cyclopentyl, cyclohexyl, cycloheptyl, and the like.

The term "alkoxy" used herein refers to straight or branched chain alkyl radical covalently bonded to the parent molecule through an —O— linkage. Examples of alkoxy groups include, but are not limited to, methoxy, ethoxy, propoxy, isopropoxy, butoxy, n-butoxy, sec-butoxy, t-butoxy and the like.

The term "alkenyl" used herein refers to a monovalent straight or branched chain radical of from two to twenty carbon atoms containing a carbon double bond including, but not limited to, 1-propenyl, 2-propenyl, 2-methyl-1-propenyl, 1-butenyl, 2-butenyl, and the like.

The term "alkynyl" used herein refers to a monovalent straight or branched chain radical of from two to twenty carbon atoms containing a carbon triple bond including, but not limited to, 1-propynyl, 1-butynyl, 2-butynyl, and the like.

The term "aryl" used herein refers to homocyclic aromatic radical whether one ring or multiple fused rings. Moreover, the term "aryl" includes fused ring systems wherein at least two aryl rings, or at least one aryl and an ortho-fused bicyclic carbocyclic radical having about nine to ten ring atoms in which at least one ring is aromatic share at least one chemical bond. Examples of "aryl" rings include, but are not limited to, optionally substituted phenyl, biphenyl, naphthalenyl, phenanthrenyl, anthracenyl, tetralinyl, fluorenyl, indenyl, and indanyl.

The term, "heterocycle" or "heterocycle group" used herein refers to an optionally substituted monocyclic, bicyclic, or tricyclic ring system comprising at least one heteroatom in the ring system backbone. The heteroatoms are independently selected from oxygen, sulfur, and nitrogen. The term, "heterocycle" includes multiple fused ring systems. Moreover, the term "heterocycle" includes fused ring systems that may have any degree of saturation provided that at least one ring in the ring system is not aromatic. The monocyclic, bicyclic, or tricyclic ring system may be substituted or unsubstituted, and can be attached to other groups via any available valence, preferably any available carbon or nitrogen. Preferred monocyclic ring systems are of 4, 5, 6, 7, or 8 members. Six membered monocyclic rings contain from up to three heteroatoms wherein each heteroatom is individually selected from oxygen, sulfur, and nitrogen, and wherein when the ring is five membered, preferably it has one or two heteroatoms wherein each heteroatom is individually selected from oxygen, sulfur, and nitrogen. Preferred bicyclic cyclic ring systems are of 8 to 12 members and include spirocycles.

The term "heteroaryl" used herein refers to an aromatic heterocyclic group, whether one ring or multiple fused rings. In fused ring systems, the one or more heteroatoms may be present in only one of the rings. Examples of heteroaryl groups include, but are not limited to, benzothiazyl, benzoxazyl, quinazolinyl, quinolinyl, isoquinolinyl, quinoxalinyl, pyridyl, pyrrolyl, oxazolyl, indolyl, thienyl and the like. The term "heterocycle" encompasses heteroaryl fused to a non-aromatic ring system.

The term "heteroatom" used herein refers to, for example, oxygen, sulfur and nitrogen.

The term "amino" used herein refers to a nitrogen radical substituted with hydrogen, alkyl, aryl, or combinations thereof. Examples of amino groups include, but are not limited to, —NHMethyl, —NH$_2$, —NMethyl$_2$, —NPhenylMethyl, —NHPhenyl, —NEthylMethyl, and the like.

The term "arylalkyl" used herein refers to one or more aryl groups appended to an alkyl radical. Examples of arylalkyl groups include, but are not limited to, benzyl, phenethyl, phenpropyl, phenbutyl, and the like.

The term "heteroarylalkyl" used herein refers to one or more heteroaryl groups appended to an alkyl radical. Examples of heteroarylalkyl include, but are not limited to, pyridylmethyl, furanylmethyl, thiopheneylethyl, and the like.

The term "aryloxy" used herein refers to an aryl radical covalently bonded to the parent molecule through an —O— linkage.

The term "alkylthio" used herein refers to straight or branched chain alkyl radical covalently bonded to the parent molecule through an —S— linkage.

The term "carbonyl" used herein refers to C=O (i.e. carbon double bonded to oxygen).

The term "oxo" used herein refers to =O (i.e. double bond to oxygen). For example, cyclohexane substituted with "oxo" is cyclohexanone.

The term "alkanoyl" used herein refers to a "carbonyl" substituted with an "alkyl" group, the "alkanoyl" group is covalently bonded to the parent molecule through the carbon of the "carbonyl" group. Examples of alkanoyl groups include, but are not limited to, methanoyl, ethanoyl, propanoyl, and the like. Methanoyl is commonly known as acetyl.

As used herein, a radical indicates species with a single, unpaired electron such that the species containing the radical can be covalently bonded to another species. Hence, in this context, a radical is not necessarily a free radical. Rather, a radical indicates a specific portion of a larger molecule. The term "radical" can be used interchangeably with the term "group."

As used herein, a substituted group is derived from the unsubstituted parent structure in which there has been an exchange of one or more hydrogen atoms for another atom or group.

Asymmetric carbon atoms may be present in the compounds described. All such isomers, including diastereomers and enantiomers, as well as the mixtures thereof are intended to be included in the scope of the recited compound. In certain cases, compounds can exist in tautomeric forms. All tautomeric forms are intended to be included in the scope. Likewise, when compounds contain an alkenyl or alkenylene group, there exists the possibility of cis- and trans-isomeric forms of the compounds. Both cis- and trans-isomers, as well as the mixtures of cis- and trans-isomers, are contemplated. Thus, reference herein to a compound includes all of the aforementioned isomeric forms unless the context clearly dictates otherwise.

Various forms are included in the embodiments, including polymorphs, solvates, hydrates, conformers, salts, and prodrug derivatives. A polymorph is a composition having the same chemical formula, but a different structure. A solvate is a composition formed by solvation (the combination of solvent molecules with molecules or ions of the solute). A hydrate is a compound formed by an incorporation of water. A conformer is a structure that is a conformational isomer. Conformational isomerism is the phenomenon of molecules with the same structural formula but different conformations (conformers) of atoms about a rotating bond. Salts of compounds can be prepared by methods known to those skilled in the art. For example, salts of compounds can be prepared by reacting the appropriate base or acid with a stoichiometric equivalent of the compound.

The term "animal" as used herein includes birds, reptiles, and mammals (e.g. domesticated mammals and humans).

The terms "individual," "host," "subject," and "patient" are used interchangeably herein, and refer to a mammal, including, but not limited to, murines, simians, humans, mammalian farm animals, mammalian sport animals, and mammalian pets.

Exemplified Embodiments

In an exemplified embodiment of the invention, the compound of formula (I) is a compound of any of the formulae Ia-Iak.

Exemplified values listed below for radicals, substituents, and ranges, are for illustration only; they do not exclude other defined values or other values within defined ranges for the radicals and substituents.

An exemplified value for Ar is phenyl, 4-chlorophenyl, 4-methoxyphenyl, 2-fluorophenyl, or 2-pyridyl.

An exemplified value for X is carbon, oxygen, or nitrogen.

An exemplified value for n is 1.

An exemplified value for L is hydrogen, methyl, isopropyl, or 2-methoxyethyl.

An exemplified value for Q is hydrogen, and methyl.

Process of Preparation

Processes for preparing compounds of formula (I) are provided as further embodiments of the invention and are illustrated by the following procedures in which the meanings of the generic radicals are as given above unless otherwise qualified.

Compounds of the general formula (I) can be prepared using a number of general synthetic approaches, as illustrated below in Schemes 1-7. In one example, shown in Scheme 1, a 4-hydroxy-6-nitroquinoline of formula 3 is prepared by reacting aniline 1 with diethyl 2-(ethoxymethylene)malonate. Compound 3 is converted to the 4-chloro-6-nitroquinoline 4 by reaction with oxalyl chloride. The pyrazoloquinoline 5 is formed by reaction of 4 with aryl hydrazines. Conversion to the final product is accomplished by reduction of the 8-nitro group and reaction of resulting free amine with an appropriately N-substituted bis(chloroethyl)amine. The other approaches, shown in schemes 2-14, use methods common to those skilled in the art.

It will be understood by those of skill in the art that depicted structures that can exist in other isomeric forms, either by tautomerization or via sigmatropic rearrangements, encompass said isomeric forms.

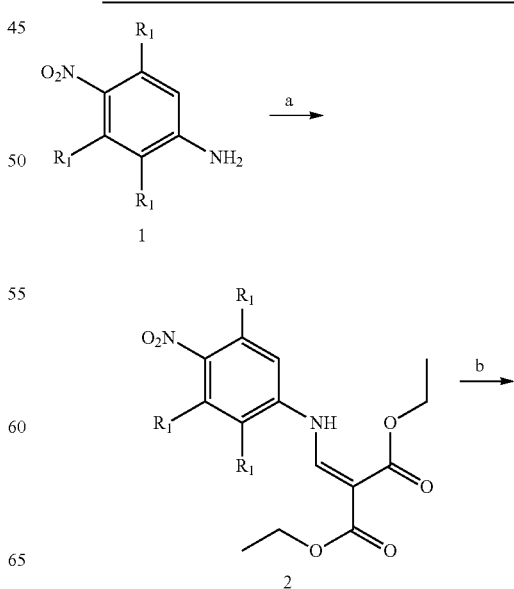

Scheme 1: General Reaction Scheme to 8-(Piperazin-1-yl)-pyrazoloquinoline

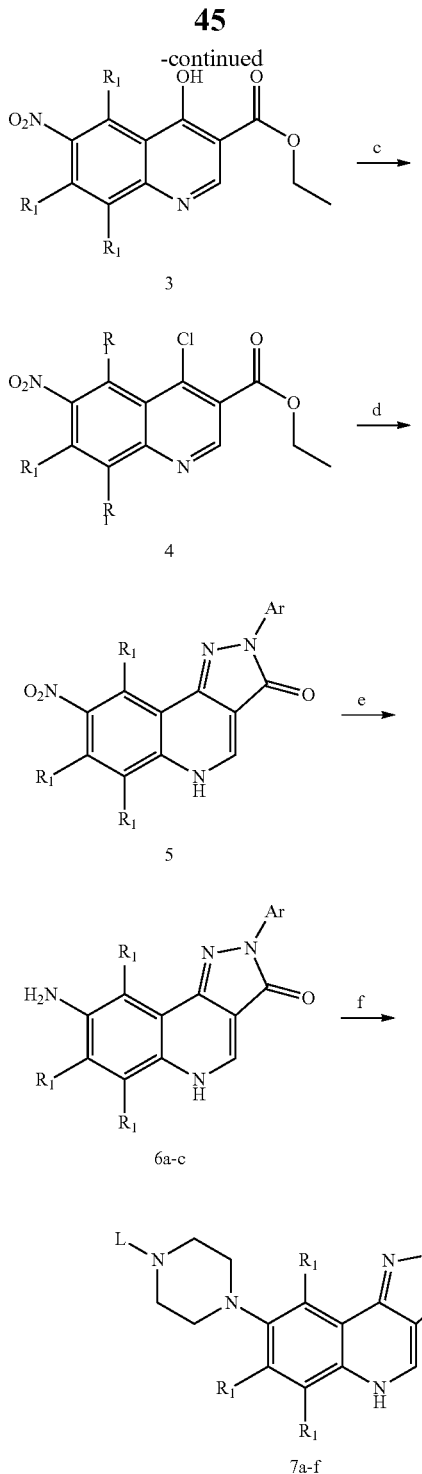

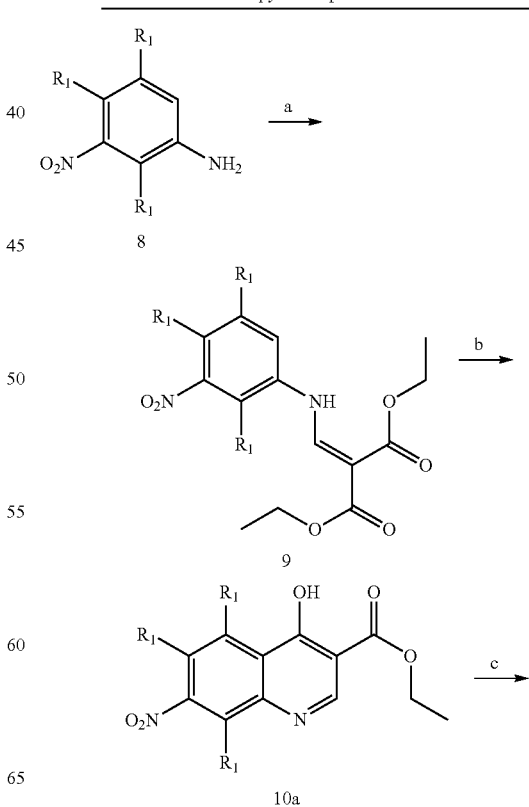

a) 1 equiv. diethyl 2-(ethoxymethylene)malonate, 125° C., 3 hrs, b) Ph₂O, reflux, 30 min-3 hrs, c) 4 equiv. oxalyl chloride, cat. DMF, CHCl₃, reflux, 3 hrs, d) 2 equiv. aryl hydrazine, 2 equiv. triethylamine, o-xylene, reflux, 12 hrs. e) SnCl₂, methanol, reflux, 12 hrs. f) bis(chloroethyl)NL·HCl, chlorobenzene, reflux, 72 hrs.

General Reaction Scheme 1 shows a representative synthetic method for the synthesis of 8-(piperazin-1-yl)-pyrazoloquinoline. The 4-nitro-aniline of Formula 1 can be reacted with diethyl 2-(ethoxymethylene)malonate under heating to afford, in an addition-elimination type reaction, the 4-nitro-enamine of Formula 2. Thermal cyclization of the compound of Formula 2 provides the hydroxyquinoline of formula 3. Solvents that can be used in step (b) include but are not limited to diphenyl ether, Dowtherm® and similar high boiling point stable solvents. Conversion of the hydroxyquinoline of formula 3 to the chloro-quinoline of formula 4 can be accomplished using a chlorinating agent in a halogenated solvent and optionally catalytic DMF. Chlorinating agents that can be used in step (c) include but are not limited to oxalyl chloride, P(O)Cl₃, PCl₅, thionyl chloride, phosgene, triphosgene, and similar chlorinating agents. Solvents that can be used in step (c) include but are not limited to chlorobenzene, methylene chloride, 1,2-dichloroethane and similar solvents. The chloro-quinoline of formula 4 can be reacted with aryl or heteroaryl hydrazine to form the tricyclic oxopyrazole of formula 5. Organic bases that can be used in step (d) include but are not limited to triethyl amine (TEA), diisopropylethyl amine (DIEA), 1,8-Diazabicyclo[5.4.0]undec-7-ene (DBU), 1,5-Diazabicyclo[4.3.0]non-5-ene (DBN), N-methylpiperidine, and the like. Solvents that can be used in step (d) include but are not limited to o-xylene, xylenes, chlorobenzene, toluene, and the like. Reduction of the nitro group of the compound of formula 5 provides the compound of formula 6a-c. The nitro group can be reduced to an amine using reducing agent such as SnCl₂ in methanol, Fe/H₂, Raney Nickel, Pt/H₂, PtO₂/H₂, and the like. The amine of the compound of formula 6a-c can be reacted with bis(chloroalkyl)amines to provide the compound of formula 7a-f. Solvents that can be used in step (f) include but are not limited to o-xylene, xylenes, chlorobenzene, toluene, and the like. Bis(chloroalkyl)amines that can be used in step (f) include but are not limited to optionally substituted bis(chloroethyl) amine, and the like.

Scheme 2: General Reaction Scheme to 7-(Piperazin-1-yl)-pyrazoloquinoline

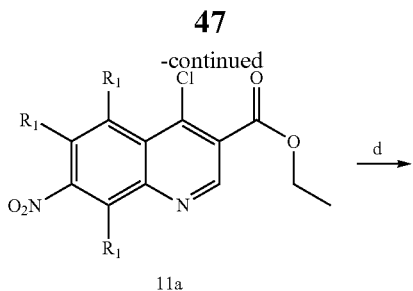

11a

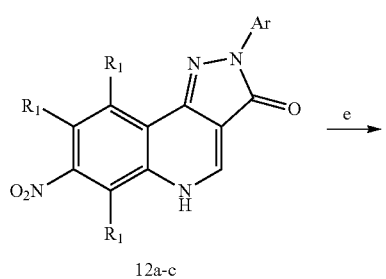

12a-c

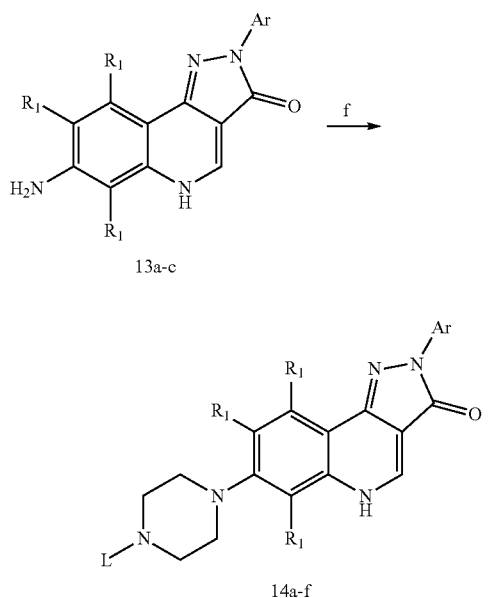

13a-c 14a-f a) 1 equiv. diethyl 2-(ethoxymethylene)malonate, 125° C., 3 hrs; b) Ph₂O, reflux, 30 min-3 hrs; c) 4 equiv. oxalyl chloride, cat. DMF, CH₂Cl₂, reflux, 3 hrs; d) 2 equiv. aryl hydrazine, 2 equiv. triethylamine, o-xylene, reflux, 12 hrs; e) SnCl₂, methanol, reflux, 12 hrs; f) bis(chloroethyl)NL·HCl, chlorobenzene, reflux, 72 hrs.

General Reaction Scheme 2 shows a representative synthetic method for the synthesis of 7-(piperazin-1-yl)-pyrazoloquinoline. The 3-nitro-aniline of formula 8 can be reacted with diethyl 2-(ethoxymethylene)malonate under heating to afford, in an addition-elimination type reaction, the 3-nitro-enamine of formula 9. Thermal cyclization of the compound of formula 9 provides the hydroxyquinoline of formula 10a. Solvents that can be used in step (b) include but are not limited to diphenyl ether, Dowtherm® and similar high boiling point stable solvents. Conversion of the hydroxyquinoline of formula 10a to the chloro-quinoline of formula 11a can be accomplished using a chlorinating agent in a halogenated solvent and optionally catalytic DMF. Chlorinating agents that can be used in step (c) include but are not limited to oxalyl chloride, P(O)Cl₃, PCl₅, thionyl chloride, phosgene, triphosgene, and similar chlorinating agents. Solvents that can be used in step (c) include but are not limited to chlorobenzene, methylene chloride, 1,2-dichloroethane, chloroform and similar solvents. The chloro-quinoline of formula 11a can be reacted with aryl or heteroaryl hydrazine to form the tricyclic oxo-pyrazole of formula 12a-c. Organic bases that can be used in step (d) include but are not limited to triethyl amine (TEA), diisopropylethyl amine (DIEA), 1,8-Diazabicyclo[5.4.0]undec-7-ene (DBU), 1,5-Diazabicyclo[4.3.0]non-5-ene (DBN), N-methylpiperidine, and the like. Solvents that can be used in step (d) include but are not limited to o-xylene, xylenes, chlorobenzene, toluene, and the like. Reduction of the nitro group of the compound of formula 12a-c provides the compound of formula 13a-c. The nitro group can be reduced to an amine using reducing agent such as SnCl₂ in methanol, Fe/H₂, Raney Nickel, Pt/H₂, PtO₂/H₂, and the like. The amine of the compound of formula 13a-c can be reacted with bis(chloroalkyl)amines to provide the compound of formula 14a-f. Solvents that can be used in step (f) include but are not limited to o-xylene, xylenes, chlorobenzene, toluene, and the like. Bis(chloroalkyl)amines that can be used in step (f) include optionally substituted bis(chloroethyl)amine, and the like.

Scheme 3: Alternative Method to Synthesize-8-(morpholin-4-yl)-pyrazoloquinoline or 8-(piperidin-1-yl)-pyrazoloquinoline

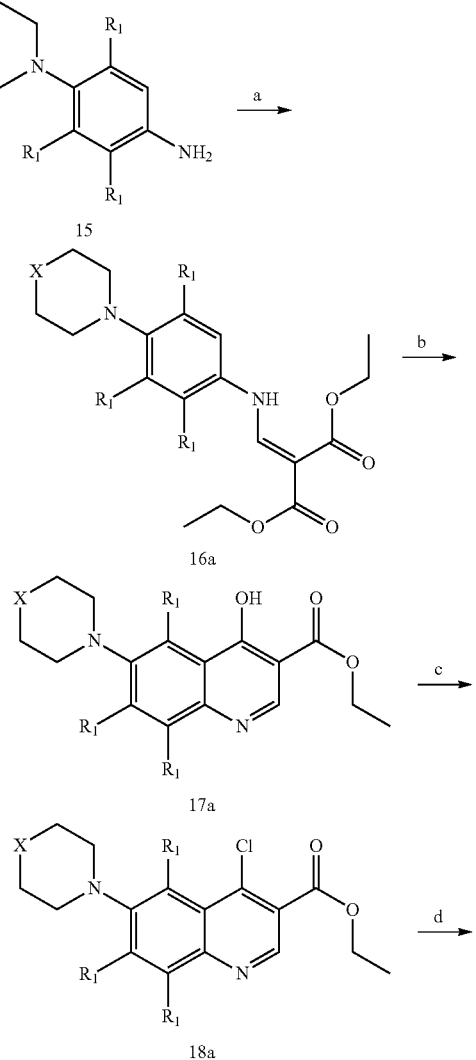

-continued

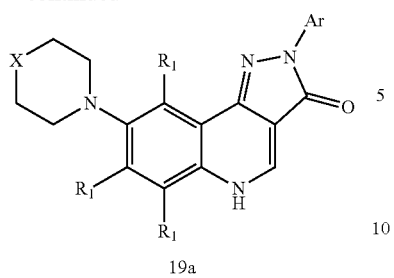

19a

X = NL, O, C(Q)2, or S(O)z;
z is 0, 1, or 2 a) 1 equiv. diethyl 2-(ethoxymethylene)malonate, 125° C., 3 hrs; b) Ph₂O, reflux, 30 min-3 hrs; c) 4 equiv. oxalyl chloride, cat. DMF, CH₂Cl₂, reflux, 3 hrs; d) equiv. aryl hydrazine, 2 equiv. triethylamine, o-xylene, reflux, 12 hrs.

General Reaction Scheme 3 shows a representative synthetic method for the synthesis of 8-(morpholin-4-yl)-pyrazoloquinoline or 8-(piperidin-1-yl)-pyrazoloquinoline. The 4-morpholine- or piperidine-aniline of formula 15 can be reacted with diethyl 2-(ethoxymethylene)malonate under heating to afford, in an addition-elimination type reaction, the 4-morpholine- or piperidine-enamine of formula 16a. Thermal cyclization of the compound of formula 16a provides the morpholine- or piperidine-hydroxyquinoline of formula 17a. Solvents that can be used in step (b) include but are not limited to diphenyl ether, Dowtherm® and similar high boiling point stable solvents. Conversion of the compound of formula 17a to the chloro-quinoline of formula 18a can be accomplished using a chlorinating agent in a halogenated solvent and optionally catalytic DMF. Chlorinating agents that can be used in step (c) include but are not limited to oxalyl chloride, P(O)Cl₃, PCl₅, thionyl chloride, phosgene triphosgene, and similar chlorinating agents. Solvents that can be used in step (c) include but are not limited to chlorobenzene, methylene chloride, 1,2-dichloroethane, chloroform and similar solvents. The chloro-quinoline of formula 18a can be reacted with aryl or heteroaryl hydrazine to form the tricyclic oxo-pyrazole of formula 19a. Organic bases that can be used in step (d) include but are not limited to triethyl amine (TEA), diisopropylethyl amine (DIEA), 1,8-Diazabicyclo[5.4.0]undec-7-ene (DBU), 1,5-Diazabicyclo[4.3.0]non-5-ene (DBN), N-methylpiperidine, and the like. Solvents that can be used in step (d) include but are not limited to o-xylene, xylenes, chlorobenzene, toluene, and the like.

Scheme 4: Alternative Method to Synthesize 8-(piperazin-1-yl), 8-(piperidin-1-yl), or 8-(morpholin-4-yl)-pyrazoloquinoline

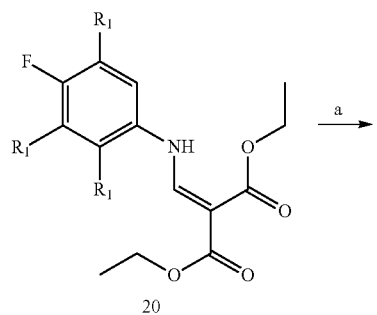

20

-continued

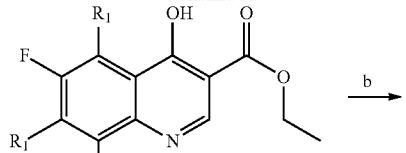

21a

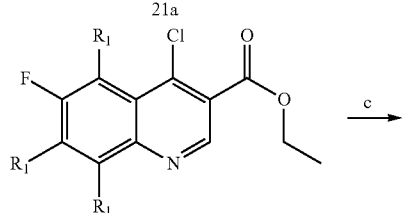

22a

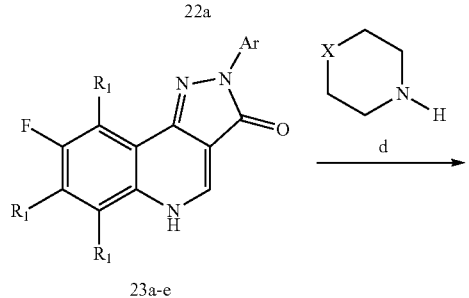

23a-e

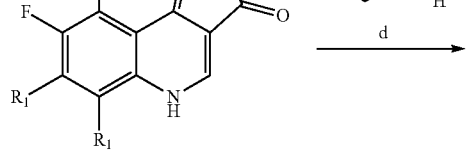

19b-k

X = NL, O, C(Q)2, or S(O)z;
z is 0, 1, or 2 a) Ph₂O, reflux, 30 min-3 hrs; b) 4 equiv. oxalyl chloride, cat. DMF, CH₂Cl₂, reflux, 3 hrs; c) 2 equiv. aryl hydrazine, 2 equiv. triethylamine, o-xylene, reflux, 12 hrs., 175° C., 12 hrs; d) 175° C., 72 hrs General Reaction Scheme 4 shows a representative synthetic method for the synthesis of 8-(piperazin-1-yl), 8-(piperidin-1-yl), or 8-(morpholin-4-yl)-pyrazoloquinoline. Thermal cyclization of the enamine of formula 20 provides the fluoro-hydroxyquinoline of formula 21a. Solvents that can be used in step (a) include but are not limited to diphenyl ether, Dowtherm® and similar high boiling point stable solvents. Conversion of the compound of formula 21a to the fluoro-chloro-quinoline of formula 22a can be accomplished using a chlorinating agent in a halogenated solvent and optionally catalytic DMF. Chlorinating agents that can be used in step (b) include but are not limited to oxalyl chloride, P(O)Cl₃, PCl₅, thionyl chloride, phosgene, triphosgene, and similar chlorinating agents. Solvents that can be used in step (b) include but are not limited to chlorobenzene, methylene chloride, 1,2-dichloroethane, chloroform and similar solvents. The chloro-quinoline of formula 22a can be reacted with aryl or heteroaryl hydrazine to form the tricyclic oxo-pyrazole of formula 23a-e. Organic bases that can be used in step (c) include but are not limited to triethyl amine (TEA), diisopropylethyl amine (DIEA), 1,8-Diazabicyclo[5.4.0]undec-7-ene (DBU), 1,5-Diazabicyclo[4.3.0]non-5-ene (DBN), N-methylpiperidine, and the like. Solvents that can be used in step (c)

include but are not limited to o-xylene, xylenes, chlorobenzene, toluene, and the like. Displacement of the fluoro of the compound of formula 23a-e with a cyclic amine under heating provides the compound of formula 19b-k. Step (d) can be performed with solvent or neat.

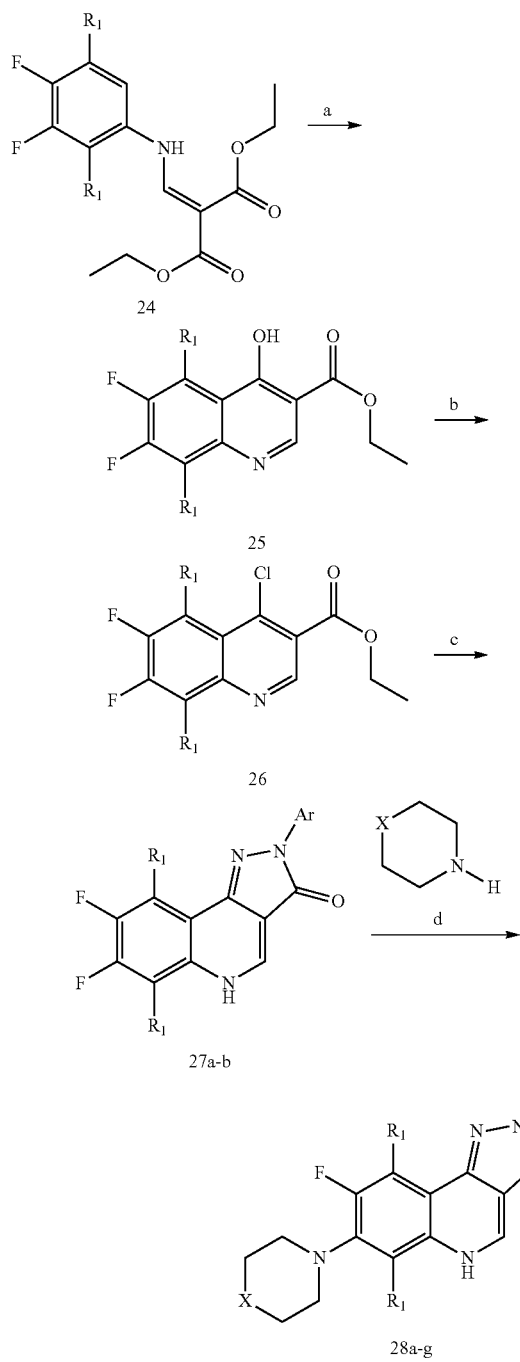

Scheme 5: Alternative Method to Synthesize 7-(piperazin-1-yl), or 7-(morpholin-4-yl-pyrazoloquinoline X = NL, O, C(Q)2, or S(O)z;
z is 0, 1, or 2 a) Ph₂O, reflux, 30 min-3 hrs; b) 4 equiv. oxalyl chloride, cat. DMF, CH₂Cl₂, reflux, 3 hrs; c) 2 equiv. aryl hydrazine, 2 equiv. triethylamine, o-xylene, reflux, 12 hrs., 175° C., 12 hrs; d) 175° C., 72 hrs General Reaction Scheme 5 shows a representative synthetic method for the synthesis of 7-(piperazin-1-yl), 7-(piperidin-1-yl), or 7-(morpholin-4-yl)-pyrazoloquinoline. Thermal cyclization of the enamine of formula 24 provides the difluoro-hydroxyquinoline of formula 25. Solvents that can be used in step (a) include but are not limited to diphenyl ether, Dowtherm® and similar high boiling point stable solvents. Conversion of the compound of formula 25 to the difluoro-chloro-quinoline of formula 26 can be accomplished using a chlorinating agent in a halogenated solvent and optionally catalytic DMF. Chlorinating agents that can be used in step (b) include but are not limited to oxalyl chloride, $P(O)Cl_3$, $PCl_5$, thionyl chloride, phosgene, triphosgene, and similar chlorinating agents. Solvents that can be used in step (b) include but are not limited to chlorobenzene, methylene chloride, 1,2-dichloroethane, chloroform and similar solvents. The chloro-quinoline of formula 26 can be reacted with aryl or heteroaryl hydrazine to form the tricyclic oxo-pyrazole of formula 27a-b. Organic bases that can be used in step (c) include but are not limited to triethyl amine (TEA), diisopropylethyl amine (DIEA), 1,8-Diazabicyclo[5.4.0]undec-7-ene (DBU), 1,5-Diazabicyclo[4.3.0]non-5-ene (DBN), N-methylpiperidine, and the like. Solvents that can be used in step (c) include but are not limited to o-xylene, xylenes, chlorobenzene, toluene, and the like. Displacement of the fluoro of the compound of formula 27a-b with a cyclic amine under heating provides the compound of formula 28a-g. Step (d) can be performed with solvent or neat.

Scheme 6: Alternative Method to Synthesize 7-(piperazin-1-yl), 7-(piperidin-1-yl), or 7-(morpholin-4-yl)-pyrazoloquinoline

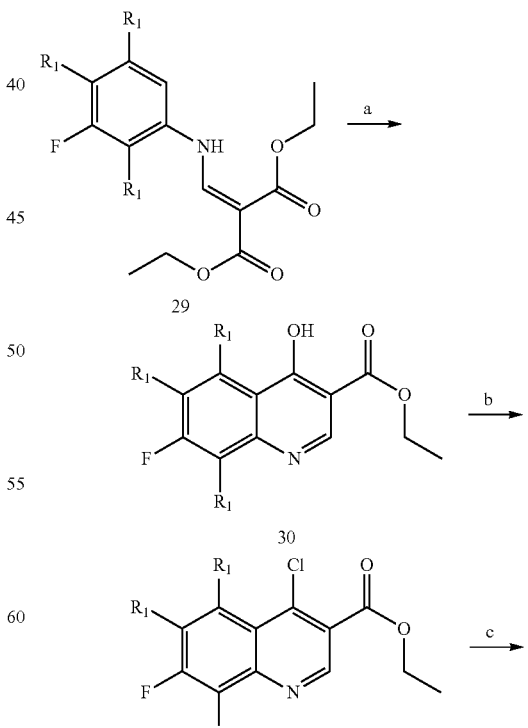

-continued

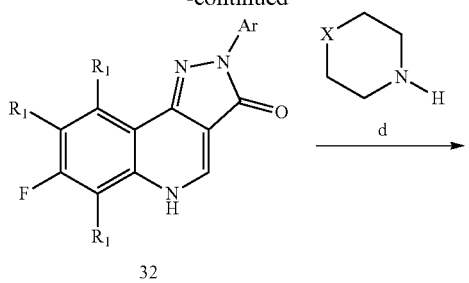
32

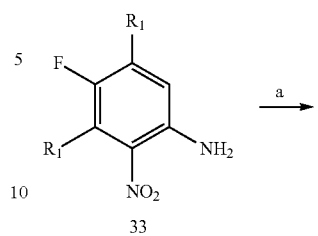

28h

X = NL, O, C(Q)2, or S(O)z;
z is 0, 1, or 2 a) Ph₂O, reflux, 30 min-3 hrs; b) 4 equiv. oxalyl chloride, cat. DMF, CH₂Cl₂, reflux, 3 hrs; c) 2 equiv. aryl hydrazine, 2 equiv. triethylamine, o-xylene, reflux, 12 hrs. 175° C., 12 hrs; d) 175° C., 72 hrs General Reaction Scheme 6 shows a representative synthetic method for the synthesis of 7-(piperazin-1-yl), 7-(piperidin-1-yl), or 7-(morpholin-4-yl)-pyrazoloquinoline. Thermal cyclization of the enamine of formula 29 provides the fluoro-hydroxyquinoline of formula 30. Solvents that can be used in step (a) include but are not limited to diphenyl ether, Dowtherm® and similar high boiling point stable solvents. Conversion of the compound of formula 30 to the fluoro-chloro-quinoline of formula 31 can be accomplished using a chlorinating agent in a halogenated solvent and optionally catalytic DMF. Chlorinating agents that can be used in step (b) include but are not limited to oxalyl chloride, P(O)Cl₃, PCl₅, thionyl chloride, phosgene, triphosgene, and similar chlorinating agents. Solvents that can be used in step (b) include but are not limited to chlorobenzene, methylene chloride, 1,2-dichloroethane, chloroform and similar solvents. The chloro-quinoline of formula 31 can be reacted with aryl or heteroaryl hydrazine to form the tricyclic oxo-pyrazole of formula 32. Organic bases that can be used in step (c) include but are not limited to triethyl amine (TEA), diisopropylethyl amine (DIEA), 1,8-Diazabicyclo[5.4.0]undec-7-ene (DBU), 1,5-Diazabicyclo[4.3.0]non-5-ene (DBN), N-methylpiperidine, and the like. Solvents that can be used in step (c) include but are not limited to o-xylene, xylenes, chlorobenzene, toluene, and the like. Displacement of the fluoro of the compound of formula 32 with a cyclic amine under heating provides the compound of formula 28h. Step (d) can be performed with solvent or neat.

Scheme 7: Method to Synthesize 6-Substituted Pyrazoloquinoline

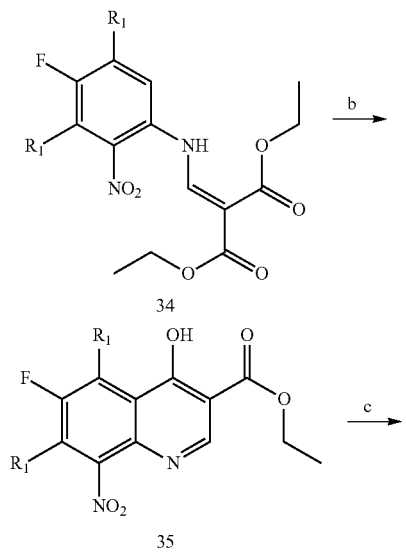

34

35

36

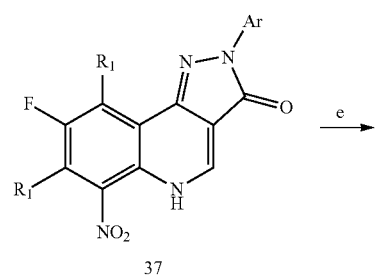
37

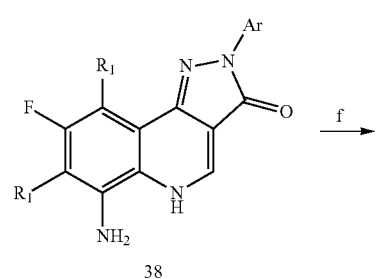
38

-continued

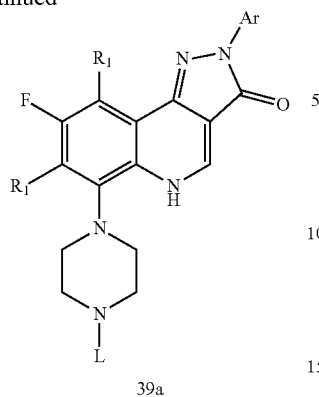

39a a) 1 equiv. diethyl 2-(ethoxymethylene)malonate, 125° C., 3 hrs, b) Ph₂O, reflux, 30 min-3 hrs, c) 4 equiv. oxalyl chloride, cat. DMF, CH₂Cl₂, reflux, 3 hrs, d) 2 equiv. aryl hydrazine, 2 equiv. triethylamine, o-xylene, reflux, 12 hrs. e) SnCl₂, methanol, reflux, 12 hrs. f) bis(chloroethyl)N-L•HCl, chlorobenzene, reflux, 72 hrs.

General Reaction Scheme 7 shows a representative synthetic method for the synthesis of 6-Substituted Pyrazoloquinoline. The 2-nitro-aniline of formula 33 can be reacted with diethyl 2-(ethoxymethylene)malonate under heating to afford, in an addition-elimination type reaction, the 2-nitroenamine of formula 34. Thermal cyclization of the compound of formula 34 provides the hydroxyquinoline of formula 35. Solvents that can be used in step (b) include but are not limited to diphenyl ether, Dowtherm® and similar high boiling point stable solvents. Conversion of the hydroxyquinoline of formula 35 to the chloro-quinoline of formula 36 can be accomplished using a chlorinating agent in a halogenated solvent and optionally catalytic DMF. Chlorinating agents that can be used in step (c) include but are not limited to oxalyl chloride, P(O)Cl₃, PCl₅, thionyl chloride, phosgene, triphosgene, and similar chlorinating agents. Solvents that can be used in step (c) include but are not limited to chlorobenzene, methylene chloride, 1,2-dichloroethane, chloroform and similar solvents. The chloro-quinoline of formula 36 can be reacted with aryl or heteroaryl hydrazine to form the tricyclic oxo-pyrazole of formula 37. Organic bases that can be used in step (d) include but are not limited to triethyl amine (TEA), diisopropylethyl amine (DIEA), 1,8-Diazabicyclo[5.4.0]undec-7-ene (DBU), 1,5-Diazabicyclo[4.3.0]non-5-ene (DBN), N-methylpiperidine, and the like. Solvents that can be used in step (d) include but are not limited to o-xylene, xylenes, chlorobenzene, toluene, and the like. Reduction of the nitro group of the compound of formula 37 provides the compound of formula 38. The nitro group can be reduced to an amine using reducing agent such as SnCl₂ in methanol, Fe/H₂, Raney Nickel, Pt/H₂, PtO₂/H₂, and the like. The amine of the compound of formula 38 can be reacted with bis(chloroalkyl)amines to provide the compound of formula 39a. Solvents that can be used in step (f) include but are not limited to o-xylene, xylenes, chlorobenzene, toluene, and the like. Bis(chloroalkyl)amines that can be used in step (f) include but are not limited to optionally substituted bis(chloroethyl)amine, and the like.

Scheme 8: Method to Synthesize 2-thiopheno-Pyrazoloquinoline

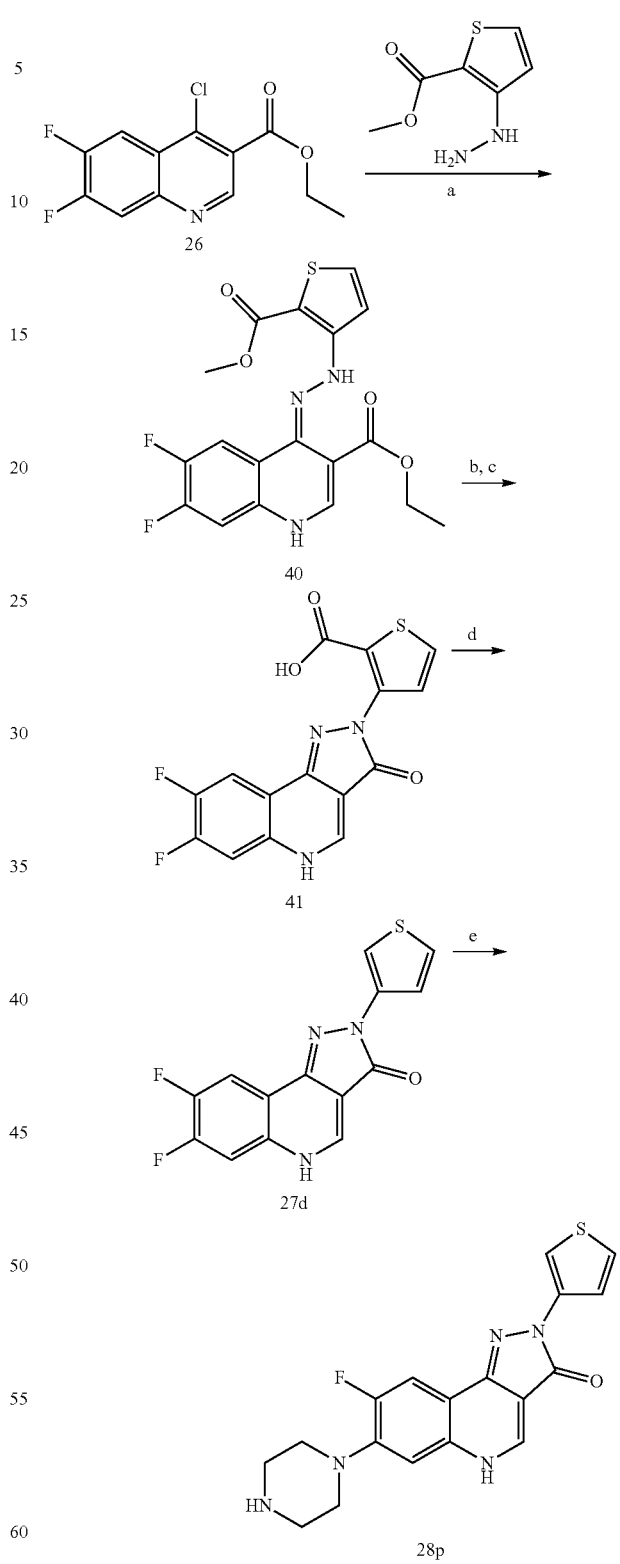

a) NaOH/Ethanol, b) NaOH, Ethanol, c) NaOH, Ethanol, d) Cu, Quinoline, e) piperazine, 175° C., 72 hrs Reaction Scheme 8 shows a representative synthetic method for the synthesis of 2-thiopheno-Pyrazoloquinoline. Reaction of the chloro-quinoline of formula 26 with methyl 3-hydrazinylthiophene-2-carboxylate under basic conditions can provide a compound of formula 40. Conditions that can be used in step (a) include but are not limited to NaOH in ethanol, NaOH in MeOH, and the like. The compound of formula 40 can be converted to the compound of formula 41 under basic conditions. Conditions that can be used for the conversion of the compound of formula 40 to the carboxylic acid of formula 41 include but are not limited to NaOH in ethanol, NaOH in MeOH, and the like. The compound of formula 41 can be converted to the compound of formula 27d by decarboxylation using Copper in the presence of quinoline. Displacement of a fluoro group of the compound of formula 27d with piperazine under heating provides the compound of formula 28p. Step (e) can be performed with solvent or neat.

Reaction Scheme 9 shows a representative synthetic method for the synthesis of 6,8-difluoro-7-(piperazin-1-yl)-pyrazoloquinoline. Conversion of the compound of formula 41 to the trifluoro-chloro-quinoline of formula 42 can be accomplished using a chlorinating agent in a halogenated solvent and optionally catalytic DMF. Chlorinating agents that can be used in step (a) include but are not limited to oxalyl chloride, P(O)Cl$_3$, PCl$_5$, thionyl chloride, phosgene, triphosgene, and similar chlorinating agents. Solvents that can be used in step (a) include chlorobenzene, methylene chloride, 1,2-dichloroethane, chloroform and similar solvents. The chloro-quinoline of formula 42 can be reacted with phenylhydrazine to form the tricyclic oxo-pyrazole of formula 43a. Organic bases that can be used in step (b) include but are not limited to triethyl amine (TEA), diisopropylethyl amine (DIEA), 1,8-Diazabicyclo[5.4.0]undec-7-ene (DBU), 1,5-Diazabicyclo[4.3.0]non-5-ene (DBN), N-methylpiperidine, and the like. Solvents that can be used in step (b) include but are not limited to o-xylene, xylenes, chlorobenzene, toluene, and the like. Displacement of a fluoro of the compound of formula 43a with a cyclic amine under heating provides the compound of formula 44a-d. Step (c) can be performed with solvent or neat.

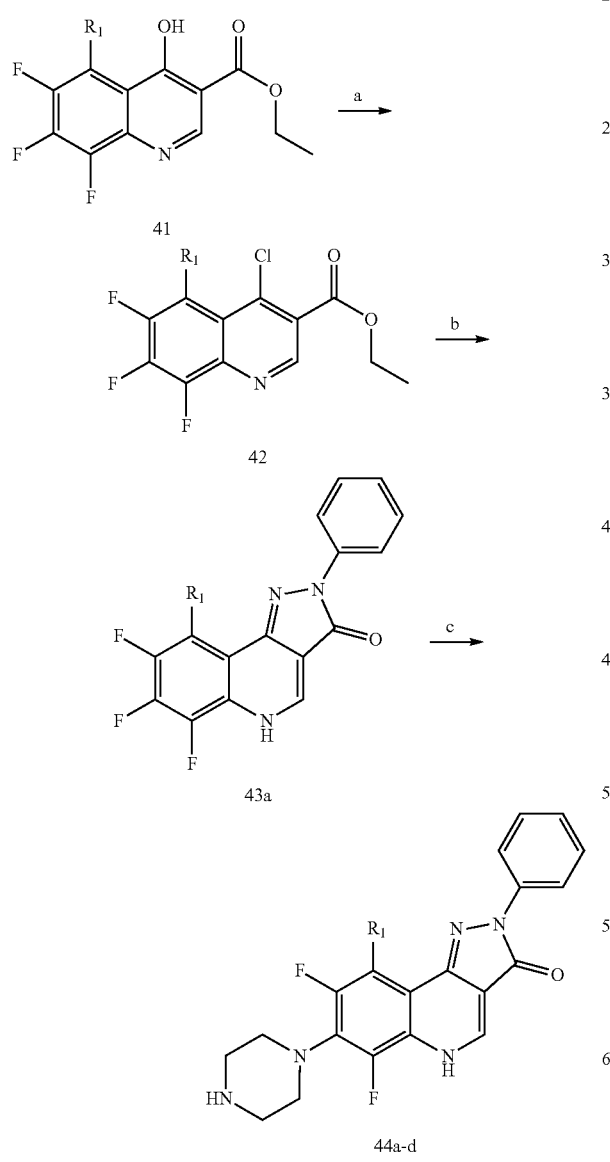

Scheme 9: Alternative Method to Synthesize 6,8-difluoro-7-(piperazin-1-yl)-pyrazoloquinoline a) 4 equiv. oxalyl chloride, cat. DMF, CH$_2$Cl$_2$, reflux, 3 hrs; b) 2 equiv. aryl hydrazine, 2 equiv. triethylamine, o-xylene, reflux, 12 hrs. 175° C., 12 hrs; c) 175° C., 72 hrs

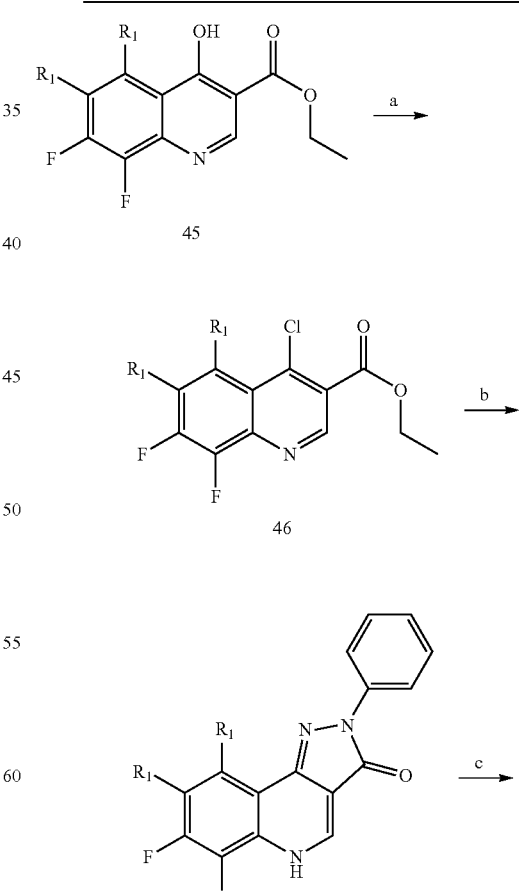

Scheme 10: Method to Synthesize 6-fluoro-7-(piperazin-1-yl)-pyrazoloquinoline

-continued

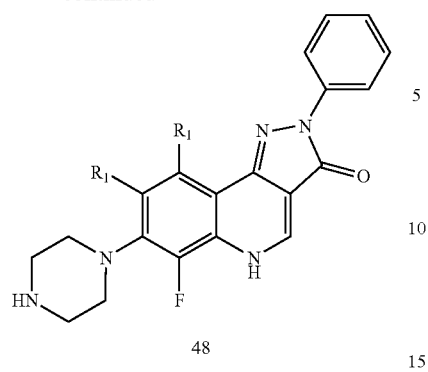

48 a) 4 equiv. oxalyl chloride, cat. DMF, CH$_2$Cl$_2$, reflux, 3 hrs; b) 2 equiv. aryl hydrazine, 2 equiv. triethylamine, o-xylene, reflux, 12 hrs. 175° C., 12 hrs; c) 175° C., 72 hrs Reaction Scheme 10 shows a representative synthetic method for the synthesis of 6-fluoro-7-(piperazin-1-yl)-pyrazoloquinoline. Conversion of the compound of formula 45 to the difluoro-chloro-quinoline of formula 46 can be accomplished using a chlorinating agent in a halogenated solvent and optionally catalytic DMF. Chlorinating agents that can be used in step (a) include but are not limited to oxalyl chloride, P(O)Cl$_3$, PCl$_5$, thionyl chloride, phosgene, triphosgene, and similar chlorinating agents. Solvents that can be used in step (a) include but are not limited to chlorobenzene, methylene chloride, 1,2-dichloroethane, chloroform and similar solvents. The difluoro-chloro-quinoline of formula 46 can be reacted with phenylhydrazine to form the tricyclic oxo-pyrazole of formula 47. Organic bases that can be used in step (b) include but are not limited to triethyl amine (TEA), diisopropylethyl amine (DIEA), 1,8-Diazabicyclo[5.4.0]undec-7-ene (DBU), 1,5-Diazabicyclo[4.3.0]non-5-ene (DBN), N-methylpiperidine, and the like. Solvents that can be used in step (b) include but are not limited to o-xylene, xylenes, chlorobenzene, toluene, and the like. Displacement of a fluoro of the compound of formula 47 with piperizine under heating provides the compound of formula 48. Step (c) can be performed with solvent or neat.

Scheme 11: Method to Synthesize 6-(piperazin-1-yl)-8-trifluoromethyl-pyrazoloquinoline

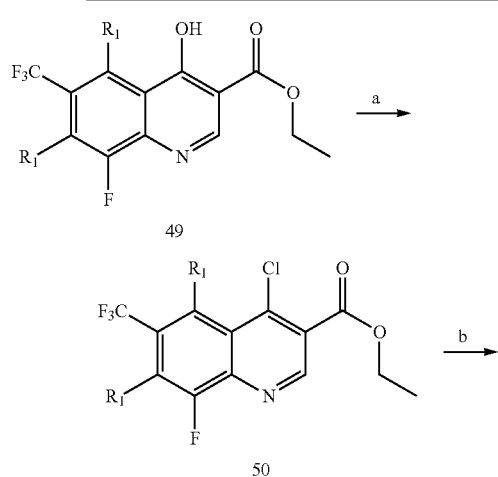

-continued

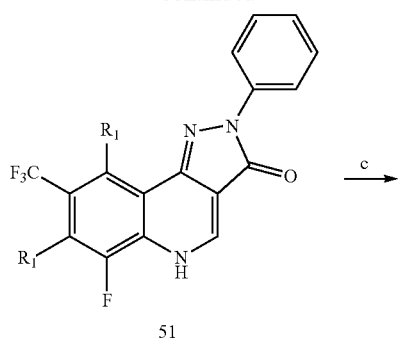

51

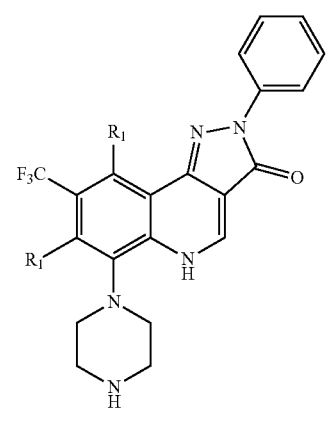

52 a) 4 equiv. oxalyl chloride, cat. DMF, CH$_2$Cl$_2$, reflux, 3 hrs; b) equiv. aryl hydrazine, 2 equiv. triethylamine, o-xylene, reflux, 12 hrs. 175° C., 12 hrs; c) 175° C., 72 hrs Reaction Scheme 11 shows a representative synthetic method for the synthesis of 6-(piperazin-1-yl)-8-trifluoromethyl-pyrazoloquinoline. Conversion of the compound of formula 49 to the fluoro-chloro-quinoline of formula 50 can be accomplished using a chlorinating agent in a halogenated solvent and optionally catalytic DMF. Chlorinating agents that can be used in step (a) include but are not limited to oxalyl chloride, P(O)Cl$_3$, PCl$_5$, thionyl chloride, phosgene, triphosgene, and similar chlorinating agents. Solvents that can be used in step (a) include but are not limited to chlorobenzene, methylene chloride, 1,2-dichloroethane, chloroform and similar solvents. The fluoro-chloro-quinoline of formula 50 can be reacted with phenylhydrazine to form the tricyclic oxo-pyrazole of formula 51. Organic bases that can be used in step (b) include but are not limited to triethyl amine (TEA), diisopropylethyl amine (DIEA), 1,8-Diazabicyclo[5.4.0]undec-7-ene (DBU), 1,5-Diazabicyclo[4.3.0]non-5-ene (DBN), N-methylpiperidine, and the like. Solvents that can be used in step (b) include but are not limited to o-xylene, xylenes, chlorobenzene, toluene, and the like. Displacement of a fluoro of the compound of formula 51 with piperizine under heating provides the compound of formula 52. Step (c) can be performed with solvent or neat.

Scheme 12: Method to Synthesize 7,9-bis(morpholin-4-yl)-8-fluoro-pyrazoloquinoline

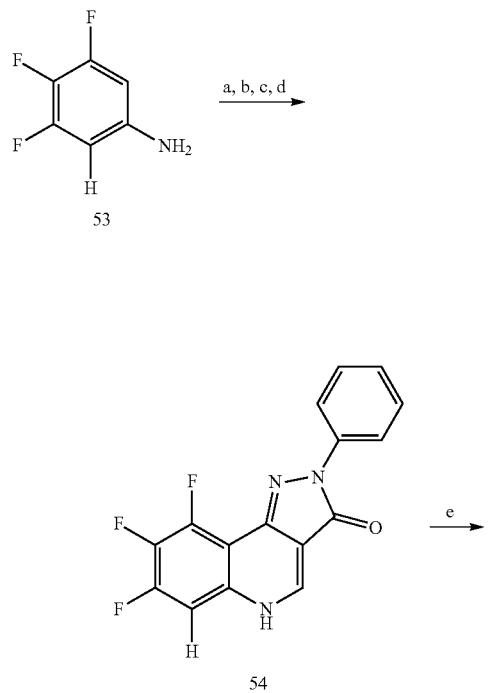

Scheme 13: Method to Synthesize 6,8-bis(morpholin-4-yl)-pyrazoloquinoline

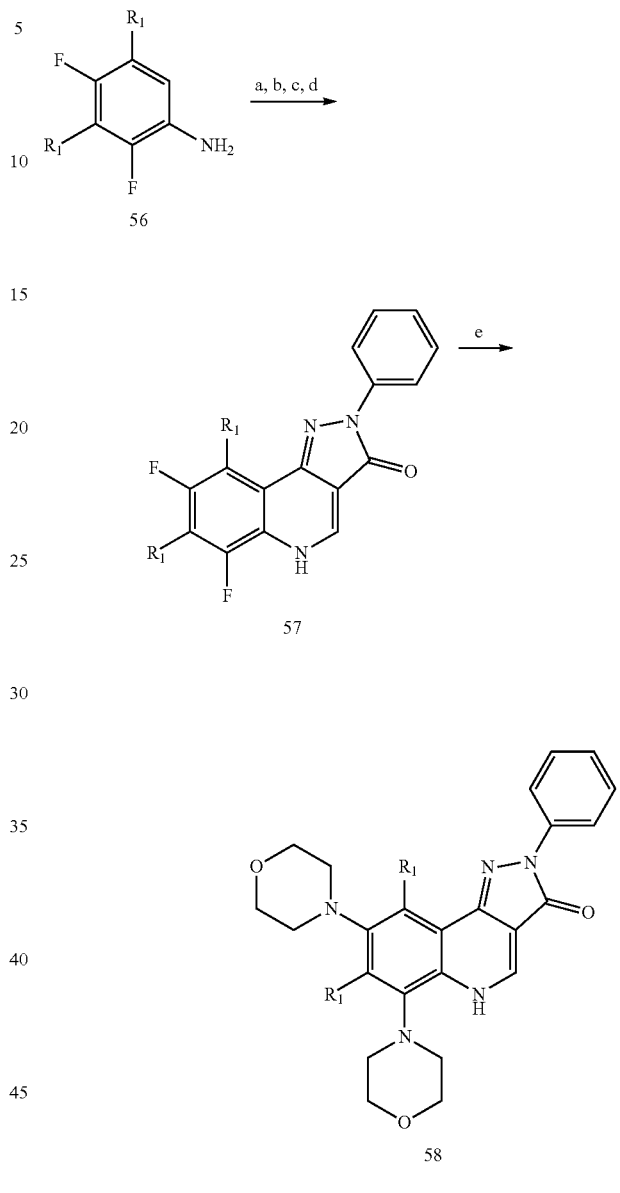

a) 1 equiv. diethyl 2-(ethoxymethylene)malonate, 125° C., 3 hrs; b) Ph$_2$O, reflux, 30 min-3 hrs; c) 4 equiv. oxalyl chloride, cat. DMF, CH$_2$Cl$_2$, reflux, 3 hrs; d) 2 equiv. aryl hydrazine, 2 equiv. triethylamine, o-xylene, reflux, 12 hrs; e) 5 equiv. morpholine, 175° C.

a) 1 equiv. diethyl 2-(ethoxymethylene)malonate, 125° C., 3 hrs; b) Ph$_2$O, reflux, 30 min-3 hrs; c) 4 equiv. oxalyl chloride, cat. DMF, CH$_2$Cl$_2$, reflux, 3 hrs; d) 2 equiv. phenylhydrazine, 2 equiv. triethylamine, o-xylene, reflux, 12 hrs; e) 5 equiv. morpholine, 175° C.

Reaction Scheme 12 shows a representative synthetic method for the synthesis of 7,9-bis(morpholin-4-yl)-8-fluoro-pyrazoloquinoline. Conversion of the compound of formula 53 to the tricyclic trifluoro-oxo-pyrazole-quinoline of formula 54 can be accomplished using the protocol disclosed in steps a, b, c, and d. Displacement of a fluoro of the compound of formula 54 with morpholine under heating provides the tricyclic trifluoro-oxo-pyrazole of formula 55. Step (e) can be performed with solvent or neat.

General Reaction Scheme 13 shows a representative synthetic method for the synthesis of 6,8-bis(morpholin-4-yl)-pyrazoloquinoline. Conversion of the compound of formula 56 to the tricyclic trifluoro-oxo-pyrazole-quinoline of formula 57 can be accomplished using the protocol disclosed in steps a, b, c, and d. Displacement of a fluoro of the compound of formula 57 with morpholine under heating provides the tricyclic trifluoro-oxo-pyrazole of formula 58. Step (e) can be performed with solvent or neat.

Scheme 14: Method to Synthesize 8-fluoro-4-methyl-7-piperazin-1-yl-pyrazoloquinoline

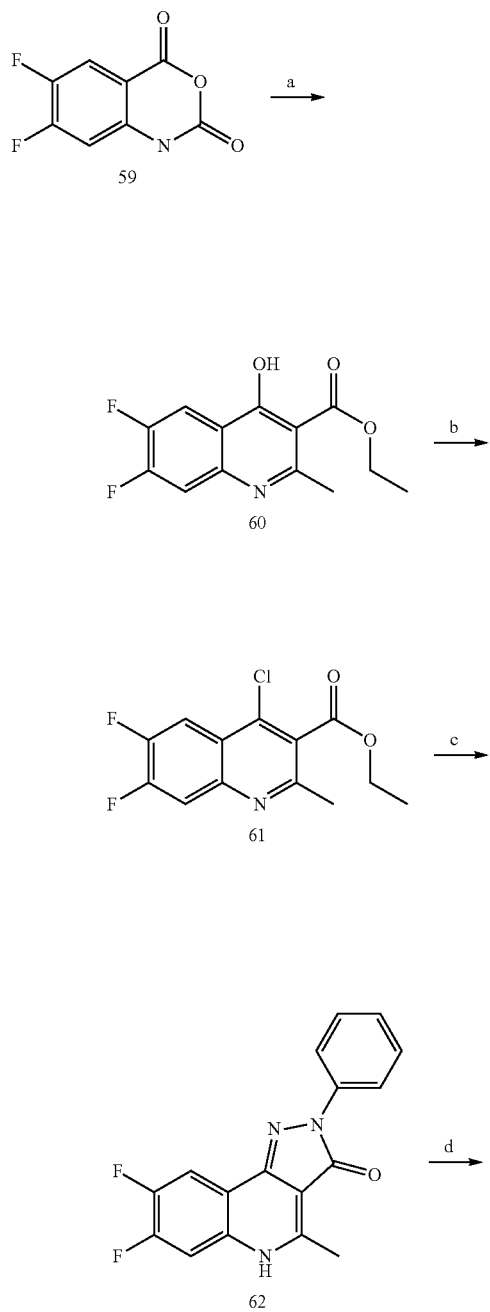

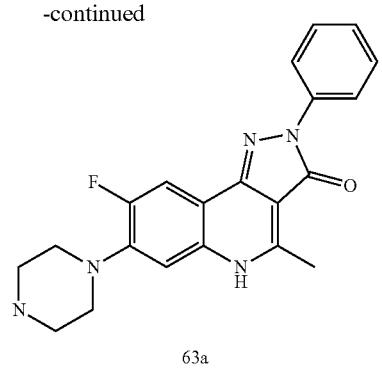

a) 10 equiv. ethyl acetoacetate, 1.1 equiv. NaH, DMA, 125° C., 10 min; b) POCl₃, 0.5 hr; c) 2 equiv. phenyl hydrazine, 2 equiv. triethylamine, o-xylene, reflux, 12 hrs; d) 5 equiv. piperazine, 125° C., 72 hours.

Reaction Scheme 14 shows a representative synthetic method for the synthesis of 8-fluoro-4-methyl-7-piperazin-1-yl-pyrazoloquinoline. Reaction of the difluoro-isatoic anhydride of formula 59 with ethyl acetoacetate in the presence of a base provides the hydroxymethylquinoline of formula 60. Solvents that can be used in step (a) include but are not limited to DMA, DMF, NMP and similar solvents. Bases that can be used in step (a) include but are not limited to sodium hydride, potassium hydride, lithium hydride and the like. Conversion of the compound of formula 60 to the difluoro-chloro-methylquinoline of formula 61 can be accomplished using a chlorinating agent. Chlorinating agents that can be used in step (b) include but are not limited to oxalyl chloride, P(O)Cl₃, PCl₅, thionyl chloride, phosgene, triphosgene, and similar chlorinating agents. The difluoro-chloro-methylquinoline of formula 61 can be reacted with phenylhydrazine to form the tricyclic oxo-pyrazole of formula 62. Organic bases that can be used in step (c) include but are not limited to triethyl amine (TEA), diisopropylethyl amine (DIEA), 1,8-Diazabicyclo[5.4.0]undec-7-ene (DBU), 1,5-Diazabicyclo[4.3.0]non-5-ene (DBN), N-methylpiperidine, and the like. Solvents that can be used in step (c) include but are not limited to o-xylene, xylenes, chlorobenzene, toluene, and the like. Displacement of a fluoro of the compound of formula 62 with piperizine under heating provides the compound of formula 63a. Step (d) can be performed with solvent or neat.

It is understood that compounds of formula (I) may be single components or mixtures of diastereomers or enantiomers if the substitutions on (I) contain chiral centers.

It is understood that compounds of formula (I) can exist in different tautomeric forms or mixtures thereof depending on the environment encompassing the compound, that is, an equilibrium can exist between the different tautomerics forms of the compounds and the equilibrium between said forms can be influenced by outside factors. For example, compounds of formula (I) can exist as tautomers as shown below:

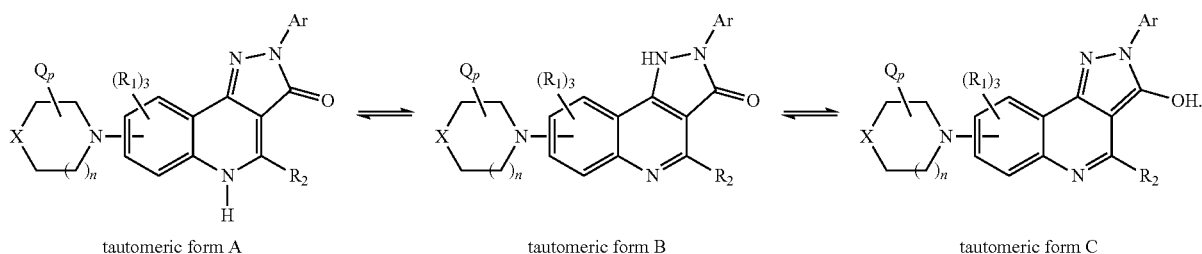

tautomeric form A          tautomeric form B          tautomeric form C

The embodiments of the invention include all possible tautomers of the compounds of formula (I). One of skill in the art will understand that depending on the definitions of the radicals of formula (I), additional tautomeric forms are anticipated and encompassed.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, besylate, tosylate, methanesulfonate, acetate, citrate, malonate, tartarate, succinate, benzoate, ascorbate, cc ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium), or alkaline earth metal (for example calcium) salts of carboxylic acids can also be made.

The compounds of formula (I) can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds of formula I can be determined by comparing their in vitro activity, and in vivo activity in animal models. Methods for the extrapolation of effective dosages in mice, and other animals, to humans are known to the those practiced in the art.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.15 to about 100 mg/kg, e.g., from about 1 to about 75 mg/kg of body weight per day, such as 0.75 to about 50 mg per kilogram body weight of the recipient per day, preferably in the range of 1 to 90 mg/kg/day, most preferably in the range of 1 to 60 mg/kg/day.

The compound is conveniently administered in unit dosage form; for example, containing 1 to 1000 mg, conveniently 10 to 750 mg, most conveniently, 5 to 500 mg of active ingredient per unit dosage form.

Ideally, the active ingredient should be administered to achieve peak plasma concentrations of the active compound of from about 0.5 to about 75 µM, preferably, about 1 to 50 µM, most preferably, about 2 to about 30 µM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The compounds of the invention can optionally be administered alone or in combination with one or more other therapeutic agents that are effective to treat disorders of the CNS, including, but not limited to, AAMI (Age Associated Memory Impairment), MCI (Mild Cognitive Impairment), Alzheimer's disease, schizophrenia, dementia (due to HIV disease, Parkinson's disease, head trauma, Huntington's disease, Pick's disease, Creutzfeld-Jakob disease), and delirium.

The routes used to synthesize the compounds of the invention are shown in Schemes 1-7 and the general methods used are detailed below

SYNTHETIC EXAMPLES

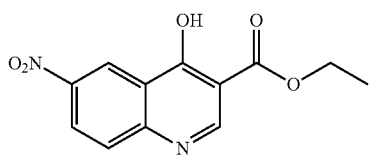

3a

Step 1: Ethyl 4-hydroxy-6-nitro-quinoline-3-carboxylate (3a): Equimolar quantities of 4-nitroaniline and diethylethoxymethylene malonate were combined and refluxed for 3 hours at 120° C., Ethanol was removed in vacuo to afford the 2-(4-nitrophenyl)-aminomethylene-malonic acid diethyl ester in quantitative yield. The resulting solid was added to refluxing Dowtherm A® and maintained at that temperature for 1 hour. The mixture was cooled to 80° C. and added to ligroin. The solid formed was collected by filtration and washed with hexane to afford product in 30-80% yield. $^1$H-NMR (DMSO-d6) δ (ppm): 1.24 (3H, t, J=7.14 Hz), 4.21 (2H, q, J=7.14 Hz), 7.79 (1H, d, J=9.06, Hz), 8.47 (1H, dd, J=9.06, 2.47 Hz), 8.65 (1H, br), 8.85 (1H, d, J=2.47 Hz). m/z 263.3 (MH$^+$).

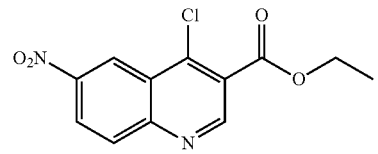

4a

Step 2: Ethyl 4-chloro-6-nitro-quinoline-3-carboxylate (4a): To a suspension of 3a in chloroform were added 4 equivalents of oxalyl chloride followed by 0.1 equiv. of dimethylformamide. The solution was refluxed for 3 hours and was quenched with 5 M sodium hydroxide solution at 4° C. The chloroform layer was collected, washed with 100 mL water and brine solution, dried over anhydrous sodium sulfate, filtered and concentrated in vacuo. Product was obtained by recrystallization using acetone. $^1$H-NMR (CDCl$_3$) δ (ppm): 1.48 (3H, t, J=7.08 Hz), 4.55 (2H, q, J=7.08 Hz), 8.31 (1H, d, J=9.27 Hz), 8.62 (1H, m), 9.36 (2H, m). m/z 281.7 (MH$^+$).

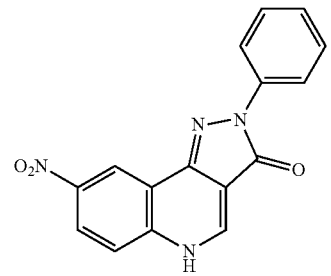

5a

Step 3: 8-Nitro-2-phenyl-2,5-dihydro-pyrazolo-[4,3-c] quinolin-3-one (5a): In a vial were added 4a, phenyl hydrazine and triethylamine. The vial was sealed and heated to 135° C. for 12 hours. The product was collected by filtration and was washed with methanol in 85% yield. $^1$H-NMR (DMSO-d6) δ (ppm): 7.19 (1H, tt, J=7.32, 1.22 Hz), 7.42 (2H, t, J=7.56 Hz), 7.84 (1H, d, J=9.03 Hz), 8.16 (2H, dd, J=8.30, 1.22 Hz), 8.82 (1H, s), 8.89 (1H, d, J=2.44 Hz). m/z 307.3 (MH$^+$).

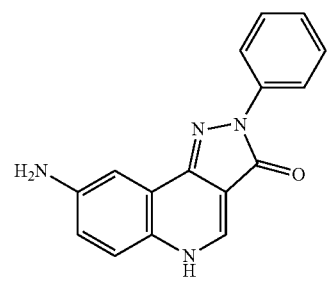

6a

Step 4: 8-Amino-2-phenyl-2,5-dihydro-pyrazolo-[4,3-c] quinolin-3-one (6a): To a solution of 5a in methanol were added catalytic amounts of Pd on carbon. Reaction mixture was stirred at 20 psi of hydrogen overnight. Solid was filtered off and methanol was removed in vacuo to afford 8-amino-2-phenyl-2,5-dihydro-pyrazolo-(4,3-c) quinolin-3-one in 87% yield. $^1$H-NMR (DMSO-d6) δ (ppm): 6.92 (1H, dd, J=8.79, 2.47 Hz), 7.13 (1H, m), 7.28 (1H, d, J=2.47 Hz), 7.43 (3H, m), 8.20 (2H, dd, J=7.69, 1.10 Hz), 8.44 (1H, d, J=6.59 Hz). m/z 277.3 (MH$^+$).

Example 1

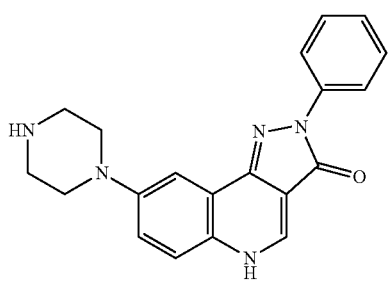
7a

Step 5: 2-Phenyl-8-piperazin-1-yl-2,5-dihydro-pyrazolo[4,3-c]quinolin-3-one (7a): Equimolar quantities of 6a and bis(chloroethyl)amine hydrochloride were suspended in chlorobenzene and stirred at 175° C. for 60 hours. The solid was collected by filtration and washed with methanol, acetonitrile and diethylether in 75% yield. $^1$H-NMR (DMSO-d6) δ (ppm): 3.25 (4H, br), 3.52 (4H, br), 7.12 (1H, t, J=7.47 Hz), 7.39 (3H, m), 7.45 (1H, m), 7.68 (1H, m), 8.22 (2H, dd, J=8.55, 0.98 Hz), 8.60 (1H, d, J=5.86 Hz), 9.12 (1H, br). m/z 346.4 (MH$^+$).

Example 2

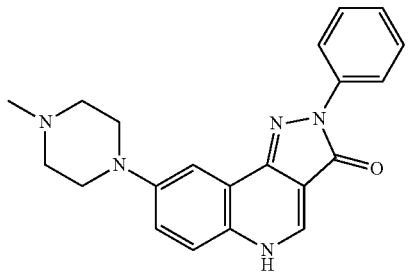
7b 8-(4-Methylpiperazin-1-yl)-2-phenyl-2,5-dihydro-pyrazolo[4,3-c]quinolin-3-one (7b): The title compound was prepared following the procedure described for 7a using 1-methylpiperazine instead of piperazine. $^1$H-NMR (DMSO-d6) δ (ppm): 3.25 (4H, br), 3.41 (3H, s), 3.52 (4H, br), 7.12 (1H, t, J=7.47 Hz), 7.39 (3H, m), 7.45 (1H, m), 7.68 (1H, m), 8.22 (2H, dd, J=8.55, 0.98 Hz), 8.60 (1H, d, J=5.86 Hz), 9.12 (1H, br). m/z 346.4 (MH$^+$). m/z 360.4 (MH$^+$).

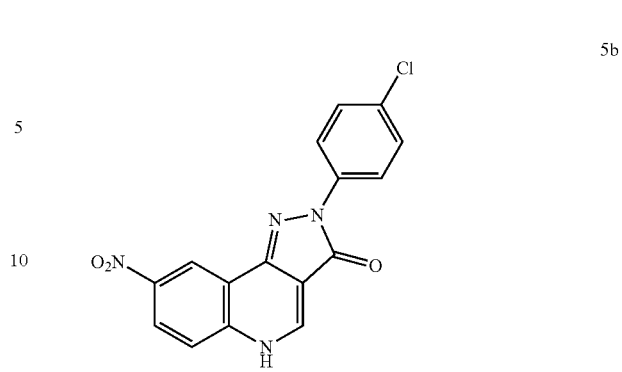
5b 2-(4'-Chlorophenyl)-8-nitro-2,5-dihydro-pyrazolo-[4,3-c]quinolin-3-one (5b): The title compound was prepared following the procedure described for 5a using 4-chlorophenylhydrazine instead of phenylhydrazine. $^1$H-NMR (DMSO-d6) δ (ppm): 7.50 (2H, d, J=8.91 Hz), 7.90 (1H, d, J=8.91 Hz), 8.29 (2H, d, J=8.91 Hz), 8.48 (1H, dd, J=8.91, 2.38 Hz), 8.88 (1H, s), 8.91 (1H, d, J=2.67 Hz). m/z 341.8 (MH$^+$).

6b

8-Amino-2-(4-chlorophenyl)-2,5-dihydro-pyrazolo-[4,3-c]quinolin-3-one (6b): The title compound was prepared following the procedure described for 6a using 5b. $^1$H-NMR (DMSO-d6) δ (ppm): 7.19 (1H, tt, J=7.32, 1.22 Hz), 7.44 (4H, m), 8.22 (4H, m), 8.48 (1H, d, J=6.59 Hz). m/z 311.8 (MH$^+$).

Example 3

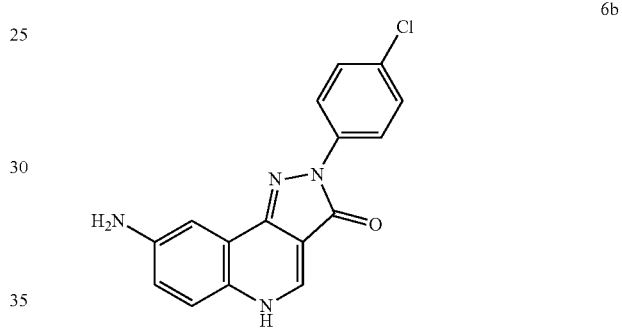
7c 2-(4'-Chlorophenyl)-8-piperazin-1-yl-2,5-dihydro-pyrazolo[4,3-c]quinolin-3-one (7c): The title compound was prepared following the procedure described for 7a using 6b. $^1$H-NMR (DMSO-d6) δ (ppm): 3.25 (4H, br), 3.50 (4H, br), 3.75 (3H, s), 7.00 (1H, d, J=9.06 Hz), 7.40 (1H, m), 7.48 (1H, br), 7.68 (1H, d, J=9.06 Hz), 7.92 (1H, d, J=8.79 Hz), 8.05 (2H, d, J=8.79 Hz), 8.56 (1H, br), 9.12 (1H, br). m/z 380.9 (MH$^+$).

Example 4

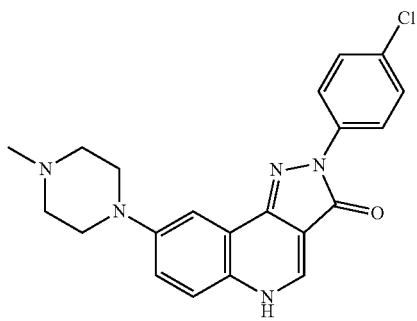

2-(4'-Chlorophenyl)-8-(4-methylpiperazin-1-yl)-2,5-dihydro-pyrazolo[4,3-c]quinolin-3-one (7d): The title compound was prepared following the procedure described for 7a using 6b and 1-methyl-piperazine. $^1$H-NMR (DMSO-d6) δ (ppm): 3.25 (4H, br), 3.50 (7H, br), 3.75 (3H, s), 7.00 (1H, d, J=9.06 Hz), 7.40 (1H, m), 7.48 (1H, br), 7.68 (1H, d, J=9.06 Hz), 7.92 (1H, d, J=8.79 Hz), 8.05 (2H, d, J=8.79 Hz), 8.56 (1H, br), 9.12 (1H, br). m/z 394.9 (MH$^+$).

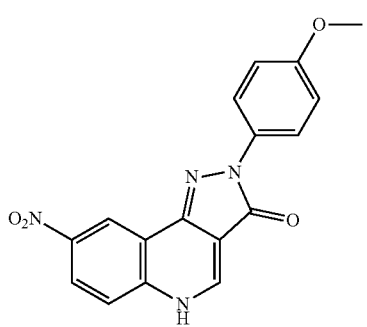

2-(4'-Methoxyphenyl)-8-nitro-2,5-dihydro-pyrazolo-[4,3-c]quinolin-3-one (5c): The title compound was prepared following the procedure for 5a using 4-methoxy phenylhydrazine instead of phenylhydrazine. $^1$H-NMR (DMSO-d6) δ (ppm): 3.77 (3H, s), 6.89 (1H, dd, J=8.91, 2.37 Hz), 6.95 (2H, m), 7.25 (1H, d, J=2.08 Hz), 7.44 (1H, d, J=8.91 Hz), 8.05 (2H, m), 8.39 (1H, d, J=6.53 Hz). m/z 337.3 (MH$^+$).

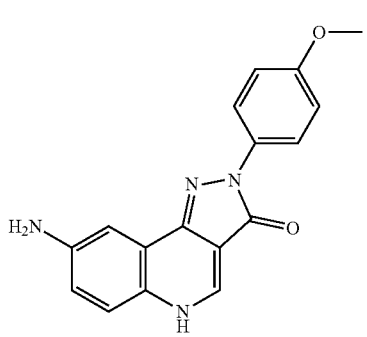 [SMILES: COc1ccc(-n2nc3c4cc([N+](=O)[O-])ccc4[nH]cc-3c2=O)cc1]

8-Amino-2-(4'-methoxyphenyl)-2,5-dihydro-pyrazolo-[4,3-c]quinolin-3-one (6c): The title compound was prepared following the procedure for 6a using 5c. $^1$H-NMR (DMSO-d6) δ (ppm): 3.77 (3H, s), 6.75 (1H, dd, J=8.91, 2.37 Hz), 6.90 (2H, m), 7.10 (1H, d, J=2.08 Hz), 7.44 (1H, d, J=8.91 Hz), 8.05 (2H, m), 8.39 (1H, d, J=6.53 Hz). m/z 307.3 (MH$^+$).

Example 5

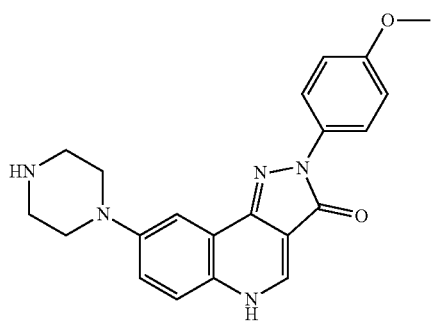

2-(4'-Methoxyphenyl)-8-piperazin-1-yl-2,5-dihydro-pyrazolo[4,3-c]quinolin-3-one (7e): The title compound was prepared following the procedure for 7a using 6c. $^1$H-NMR (DMSO-d6) δ (ppm): 3.25 (4H, br), 3.50 (4H, br), 3.75 (3H, s), 7.00 (1H, d, J=9.06 Hz), 7.40 (1H, m), 7.48 (1H, br), 7.68 (1H, d, J=9.06 Hz), 7.92 (1H, d, J=8.79 Hz), 8.05 (2H, d, J=8.79 Hz), 8.56 (1H, br), 9.12 (1H, br). m/z 376.4 (MH$^+$).

Example 6

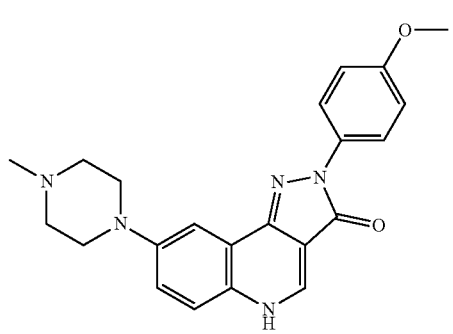

2-(4'-Methoxyphenyl)-8-(4-methylpiperazin-1-yl)-2,5-dihydro-pyrazolo[4,3-c]quinolin-3-one (7f): The title compound was prepared following the procedure for 7a using 6c and 1-methylpiperazine. $^1$H-NMR (DMSO-d6) δ (ppm): 3.25 (4H, br), 3.45 (3H, s), 3.50 (4H, br), 3.75 (3H, s), 7.00 (1H, d, J=9.06 Hz), 7.40 (1H, m), 7.48 (1H, br), 7.68 (1H, d, J=9.06 Hz), 7.92 (1H, d, J=8.79 Hz), 8.05 (2H, d, J=8.79 Hz), 8.56 (1H, br), 9.12 (1H, br). m/z 390.4 (MH$^+$).

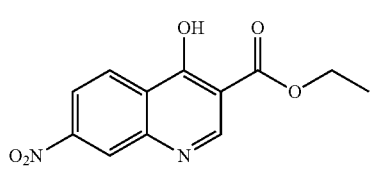

Ethyl 4-hydroxy-7-nitro-quinoline-3-carboxylate (10a): The title compound was prepared following the procedure described in Step 1 using 3-nitroaniline instead of 4-nitroaniline. $^1$H-NMR (DMSO-d6) δ (ppm): 1.24 (3H, t, J=7.14 Hz), 4.18 (2H, q, J=7.14 Hz), 8.10 (1H, dd, J=9.06, 2.19 Hz), 8.32 (1H, d, J=8.79 Hz), 8.48 (1H, d, J=2.19 Hz), 8.71 (1H, d, J=5.76 Hz). m/z 263.3 (MH$^+$).

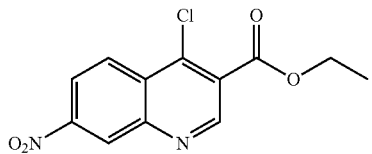

Ethyl 4-chloro-7-nitro-quinoline-3-carboxylate (11a): The title compound was prepared following the procedure described in Step 2 using 10a. $^1$H-NMR (CDCl$_3$) δ (ppm): 1.46 (3H, t, J=7.14 Hz), 4.54 (2H, q, J=7.14 Hz), 8.47 (1H, dd, J=9.34, 2.20 Hz), 8.60 (1H, d, J=9.07 Hz), 9.02 (1H, d, J=2.19 Hz), 9.32 (1H, s). m/z 281.7 (MH$^+$).

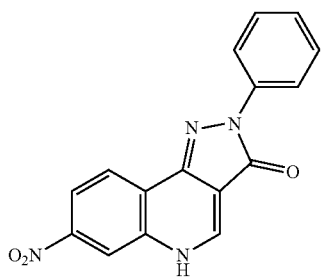

7-Nitro-2-phenyl-2,5-dihydro-pyrazolo-[4,3-c]quinolin-3-one (12a): The title compound was prepared following the procedure described in Step 3 using 11a. $^1$H-NMR (DMSO-d6) δ (ppm): 7.20 (1H, t, J=7.41 Hz), 7.48 (3H, m), 8.19 (2H, m), 8.43 (1H, dd, J=8.79, 2.46 Hz), 8.54 (1H, d, J=2.20 Hz), 8.92 (1H, s). m/z 307.3 (MH$^+$).

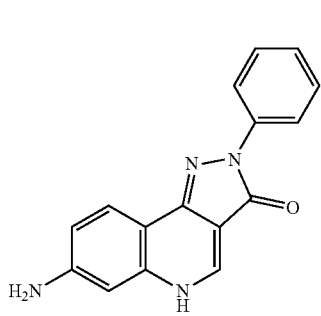

7-Amino-2-phenyl-2,5-dihydro-pyrazolo-[4,3-c]quinolin-3-one (13a): The title compound was prepared following the procedure described in Step 4 using 12a. $^1$H-NMR (DMSO-d6) δ (ppm): 6.73 (1H, d, J=1.93 Hz), 6.79 (1H, dd, J=8.51, 2.20 Hz), 7.12 (1H, t, J=7.14 Hz), 7.39 (2H, t, J=7.96 Hz), 7.87 (1H, d, J=8.79 Hz), 8.17 (2H, dd, J=7.41, 1.10 Hz), 8.49 (1H, d, J=6.32 Hz). m/z 277.3 (MH$^+$).

Example 7

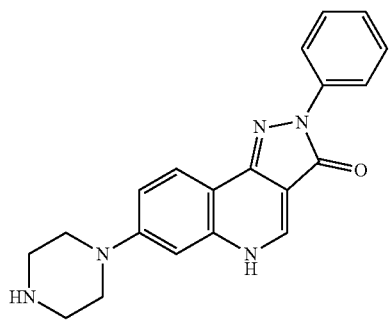

2-Phenyl-7-piperazin-1-yl-2,5-dihydro-pyrazolo[4,3-c]quinolin-3-one (14a): The title compound was prepared following the procedure in Step 5 using 13a. $^1$H-NMR (DMSO-d6) δ (ppm): 2.84 (4H, brm), 3.17 (4H, brm), 6.99 (1H, d, J=2.47 Hz), 7.10 (1H, t, J=7.42 Hz), 7.21 (1H, dd, J=8.79, 2.47 Hz), 7.41 (2H, m), 8.00 (1H, d, J=8.79 Hz), 8.17 (2H, dd, J=8.79, 1.10 Hz), 8.54 (1H, s). m/z 346.4 (MH$^+$).

Example 8

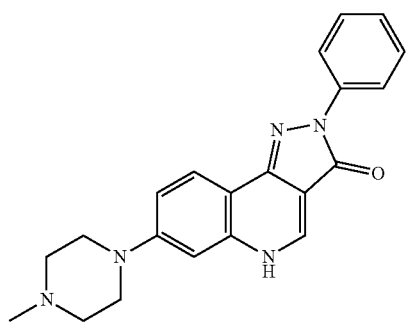

7-(4-Methylpiperazin-1-yl)-2-phenyl-2,5-dihydro-pyrazolo[4,3-c]quinolin-3-one (14b): The title compound was prepared following the procedure in Step 5 using 13a and 1-methylpiperazine. $^1$H-NMR (CD$_3$OD) δ (ppm): 2.44 (3H, s), 2.74 (4H, brm), 3.44 (4H, brm), 7.03 (1H, d, J=2.20 Hz), 7.27 (1H, ddd, J=7.41, 1.64, 1.10 Hz), 7.35 (1H, dd, J=9.07, 2.47 Hz), 7.65 (2H, m), 7.99 (2H, m), 8.17 (1H, d, J=9.07 Hz), 8.53 (1H, s). m/z 360.4 (MH$^+$).

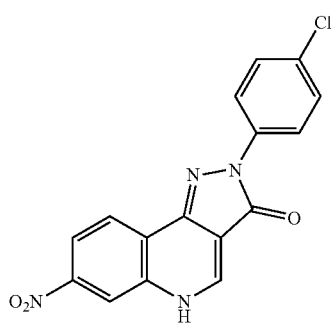

2-(4'-Chlorophenyl)-7-nitro-2,5-dihydro-pyrazolo-[4,3-c]quinolin-3-one (12b): The title compound was prepared following the procedure described for 12a using 11a and 4-chlorophenylhydrazine. ¹H-NMR (DMSO-d6) δ (ppm): 7.48 (2H, d, m), 8.20 (2H, m), 8.26 (1H, dd, J=8.61, 2.08 Hz), 8.40 (1H, d, J=8.61 Hz), 8.52 (1H, d, J=2.08 Hz), 8.92 (1H, s). m/z 341.8 (MH⁺).

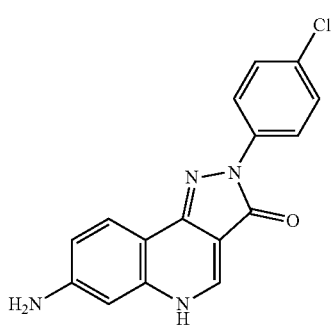

13b

7-Amino-2-(4'-chlorophenyl)-2,5-dihydro-pyrazolo-[4,3-c]quinolin-3-one (13b): The title compound was prepared following the procedure described in Step 4 using 12b. ¹H-NMR (DMSO-d6) δ (ppm): 6.74 (1H, d, J=2.20 Hz) 6.79 (1H, dd, J=8.79, 2.19 Hz), 7.42 (1H, d, J=8.79 Hz), 7.43 (1H, q, J=5.22 Hz), 7.86 (1H, d, J=8.51 Hz), 8.20 (1H, d, J=9.06 Hz), 8.21 (1H, q, J=5.21 Hz), 8.47 (1H, d, J=6.32 Hz). m/z 311.8 (MH⁺).

Example 9

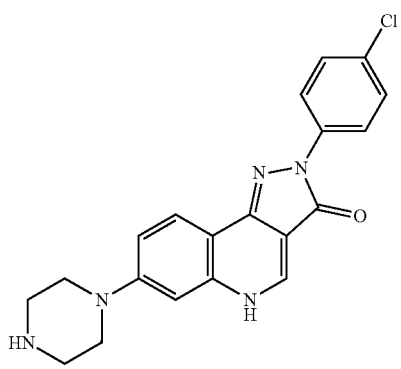

14c 2-(4'-Chlorophenyl)-7-piperazin-1-yl-2,5-dihydro-pyrazolo[4,3-c]quinolin-3-one (14c): The title compound was prepared following the procedure for 14a using 13b. ¹H-NMR (DMSO-d6) δ (ppm): 3.07 (2H, br), 3.38 (4H, br), 3.48 (2H, br), 7.12 (1H, br), 7.48 (3H, m), 8.07 (1H, d, J=9.06 Hz), 8.25 (2H, dd, J=9.07, 2.20 Hz), 8.62 (1H, d, J=6.32 Hz). m/z 380.9 (MH⁺).

Example 10

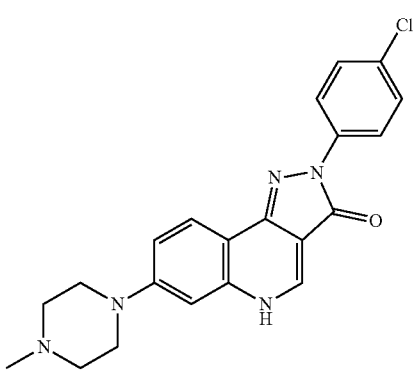

14d 2-(4-Chlorophenyl)-7-(4-methylpiperazin-1-yl)-2,5-dihydro-pyrazolo[4,3-c]quinolin-3-one (14d): The title compound was prepared following the procedure for 14a using 13b and 1-methylpiperazine. ¹H-NMR (CD₃OD) δ (ppm): 2.39 (3H, s), 2.67 (4H, brm), 3.40 (4H, brm), 7.01 (1H, d, J=2.47 Hz), 7.34 (1H, dd, J=9.07, 2.47 Hz), 7.46 (2H, dd, J=6.87, 2.20 Hz), 8.09 (2H, dd, J=7.14, 1.92 Hz), 8.19 (1H, d, J=9.07 Hz), 8.51 (1H, s). m/z 394.9 (MH⁺).

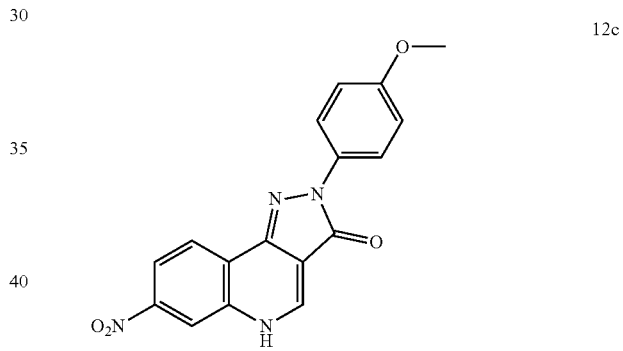

12c 2-(4'-Methoxyphenyl)-7-nitro-2,5-dihydro-pyrazolo-(4,3-c)quinolin-3-one (12c): The title compound was prepared following the procedure described 12a using 11a and 4-methoxyphenylhydrazine. ¹H-NMR (DMSO-d6) δ (ppm): 3.76 (3H, s), 7.02 (2H, d, J=9.34 Hz), 8.02 (2H, d, J=9.06 Hz), 8.27 (1H, dd, J=8.79, 2.19 Hz), 8.39 (1H, d, J=8.79 Hz), 8.52 (1H, q, J=2.20 Hz), 8.88 (1H, d, J=6.04 Hz). m/z 337.3 (MH⁺).

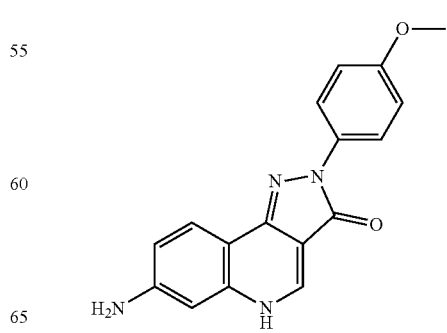

13c 7-amino-2-(4'-Methoxyphenyl)-2,5-dihydro-pyrazolo-[4,3-c]quinolin-3-one (13c): The title compound was prepared following the procedure described for 13a using 12c. ¹H-NMR (DMSO-d6) δ (ppm): 6.74 (1H, d, J=2.20 Hz) 6.79 (1H, dd, J=8.79, 2.19 Hz), 7.42 (1H, d, J=8.79 Hz), 7.43 (1H, q, J=5.22 Hz), 7.86 (1H, d, J=8.51 Hz), 8.20 (1H, d, J=9.06 Hz), 8.21 (1H, q, J=5.21 Hz), 8.47 (1H, d, J=6.32 Hz). m/z 307.3 (MH⁺).

Example 11

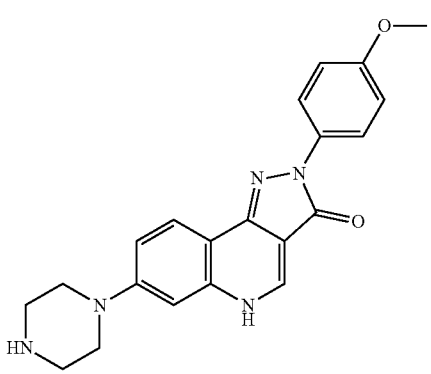 [SMILES: COc1ccc(-n2nc3c4ccc(N5CCNCC5)cc4[nH]cc-3c2=O)cc1]

2-(4-Methoxyphenyl)-7-piperazin-1-yl-2,5-dihydro-pyrazolo[4,3-c]quinolin-3-one (14e): The title compound was prepared following the procedure for 14a using 13c. ¹H-NMR (DMSO-d6) δ (ppm): 3.04 (4H, br), 3.75 (3H, s), 3.90 (4H, br), 6.8 (1H, m), 7.26 (2H, m), 7.42 (1H, m), 7.87 (1H, d, J=8.79 Hz), 8.05 (2H, d, J=9.06 Hz), 8.62 (1H, br). m/z 376.4 (MH⁺).

Example 12

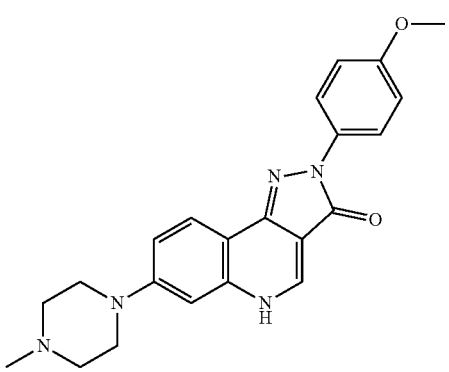

14f 2-(4-Methoxyphenyl)-7-(4-methylpiperazin-1-yl)-2,5-dihydro-pyrazolo[4,3-c]quinolin-3-one (14f): The title compound was prepared following the procedure for 14a using 13c and 1-methylpiperazine. ¹H-NMR (CD₃OD) δ (ppm): 2.32 (3H, s), 2.67 (4H, brm), 3.40 (4H, brm), 3.85 (3H, s), 6.88 (2H, m), 7.02 (1H, d, J=2.47 Hz), 7.31 (1H, dd, J=9.06, 2.20 Hz), 7.66 (2H, m), 8.16 (1H, d, J=9.06 Hz), 8.52 (1H, s). m/z 390.4 (MH⁺).

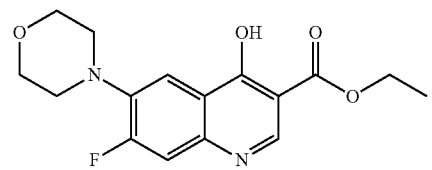

17a

Ethyl 7-fluoro-4-hydroxy-6-morpholino-quinoline-3-carboxylate (17a): The title compound was prepared following the procedure described in Step 1 using 3-fluoro-4-morpholinoaniline instead of 4-nitroaniline. ¹H-NMR (DMSO-d6) δ (ppm): 1.22 (3H, t, J=7.28 Hz), 3.00 (4H, m), 3.75 (4H, m), 4.1 (2H, q, J=7.28 Hz), 7.40 (1H, s), 7.63 (1H, m), 8.50 (1H, m). m/z 321.3 (MH⁺).

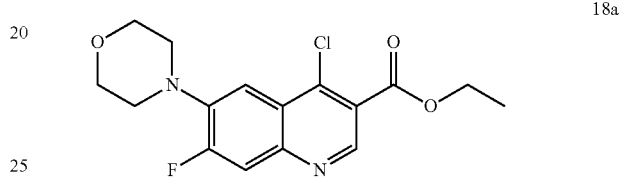

18a

Ethyl 4-chloro-7-fluoro-6-morpholino-quinoline-3-carboxylate (18a): The title compound was prepared following the procedure described in Step 2 using 17a instead of 3a. ¹H-NMR (CDCl₃) δ (ppm): 1.42 (3H, t, J=7.33 Hz), 3.23 (4H, m), 3.95 (4H, m), 4.1 (2H, q, J=7.33 Hz), 7.78 (2H, m), 7.63 (1H, m), 9.07 (1H, s). m/z 339.8 (MH⁺).

Example 13

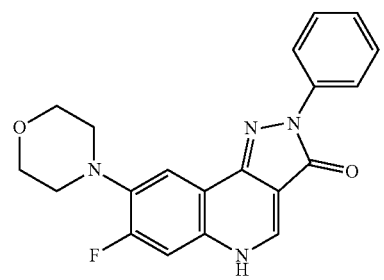

19a

7-Fluoro-8-morpholin-4-yl-2-phenyl-2,5-dihydro-pyrazolo[4,3-c]quinolin-3-one (19a): The title compound was prepared following the procedure described in Step 3 using 18a instead of 5a. ¹H-NMR (DMSO-d6) δ (ppm): 3.15 (4H, m), 3.80 (4H, m), 7.16 (1H, tt, J=7.32, 1.22 Hz), 7.40 (3H, m), 7.64 (1H, d, J=9.03 Hz), 8.20 (2H, dd, J=8.79, 1.22 Hz), 8.75 (1H, br), 12.65 (1H, br). m/z 364.4 (MH⁺).

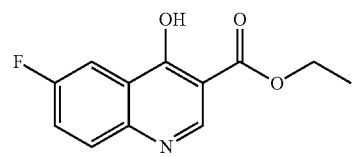

21a

Ethyl 4-hydroxy-6-fluoro-quinoline-3-carboxylate (21a): The title compound was prepared following the procedure described in Step 1 using 4-fluoroaniline instead of 4-nitroaniline. $^1$H-NMR (DMSO-d6) δ (ppm): 1.15 (3H, t, J=7.080 Hz), 4.1 (2H, q, J=7.08 Hz), 7.61 (1H, dd, J=8.30, 2.93 Hz), 7.68 (1H, dd, J=9.03, 4.63 Hz), 7.80 (1H, dd, J=9.27, 2.93 Hz), 8.56 (1H, s). m/z 237.3 (MH$^+$).

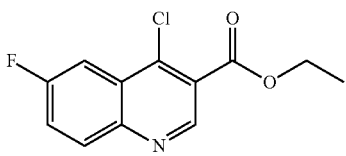

22a

Ethyl 4-chloro-6-fluoro-quinoline-3-carboxylate (22a): The title compound was prepared following the procedure described in Step 2 using 21a instead of 3. $^1$H-NMR (CDCl$_3$) δ (ppm): 1.47 (3H, t, J=7.08 Hz), 4.51 (2H, q, J=7.08 Hz), 7.63 (1H, m), 8.02 (1H, dd, J=9.52, 2.68 Hz), 8.15 (1H, dd, J=9.27, 5.37 Hz), 9.15 (1H, s). m/z 255.7 (MH$^+$).

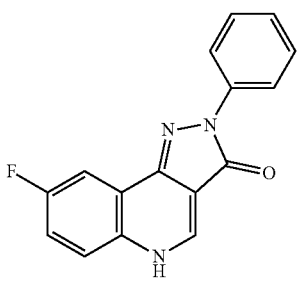

23a

8-Fluoro-2-phenyl-2,5-dihydro-pyrazolo-[4,3-c]quinolin-3-one (23a): The title compound was prepared following the procedure described in Step 3 using 22a instead of 4a. $^1$H-NMR (DMSO-d6) δ (ppm): 7.16 (1H, t, J=13.67 Hz), 7.41 (2H, t, J=7.56 Hz), 7.55 (1H, dt, J=8.54, 2.93 Hz), 7.77 (1H, dd, J=9.27, 4.88 Hz), 7.90 (1H, dd, J=9.27, 2.93 Hz), 8.18 (2H, dd, J=7.58, 1.95 Hz), 8.73 (1H, s). m/z 280.2 (MH$^+$).

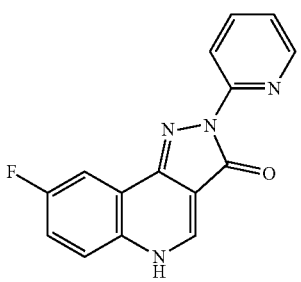

23b

8-Fluoro-2-(2'-pyridyl)-2,5-dihydro-pyrazolo-[4,3-c]quinolin-3-one (23b): The title compound was prepared following procedure for 23a using pyridyl-2-hydrazine instead of phenyl hydrazine. $^1$H-NMR (DMSO-d6) δ (ppm): 7.24 (1H, ddd, J=7.42, 4.95, 1.10 Hz), 7.57 (1H, m, J=9.06, 3.02 Hz), 7.76 (1H, dd, J=9.34, 4.95 Hz), 7.88 (2H, m), 8.18 (1H, brd, J=8.24 Hz), 8.49 (1H, ddd, J=4.95, 2.75, 1.10 Hz), 8.76 (1H, s). m/z 281.3 (MH$^+$).

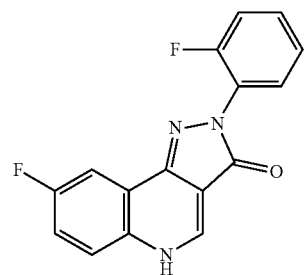

23c

8-Fluoro-2-(2'-fluorophenyl)-2,5-dihydro-pyrazolo-[4,3-c]quinolin-3-one (23c): The title compound was prepared following procedure for 23a using 2-fluorophenyl hydrazine instead of phenyl hydrazine. $^1$H-NMR (DMSO-d6) δ (ppm): 7.37 (3H, m), 7.52 (2H, m), 7.81 (2H, m), 8.74 (1H, s). m/z 298.3 (MH$^+$).

23d

8-Fluoro-2-(4'-methoxyphenyl)-2,5-dihydro-pyrazolo-[4,3-c]quinolin-3-one (23d): The title compound was prepared following procedure for 23a using 4-methoxy phenylhydrazine instead of phenyl hydrazine. $^1$H-NMR (DMSO-d6) δ (ppm): 7.05 (3H, m), 7.52 (1H, dt, J=8.52, 3.02 Hz), 7.80 (1H, dd, J=9.07, 4.94 Hz), 7.88 (1H, dd, J=9.06, 2.75 Hz), 8.05 (2H, m), 8.74 (1H, d, J=5.49 Hz). m/z 310.3 (MH$^+$).

23e

7-Chloro-8-fluoro-2-phenyl-2,5-dihydro-pyrazolo-[4,3-c]quinolin-3-one (23e): The title compound was prepared following procedure for 23a using ethyl-4,7-dichloro-6-fluoro-quinoline-3-carboxylate. $^1$H-NMR (DMSO-d6) δ (ppm): 7.20 (1H, t, J=7.41 Hz), 7.48 (3H, m), 8.19 (2H, m), 8.43 (1H, dd, J=8.79, 2.46 Hz), 8.54 (1H, d, J=2.20 Hz), 8.92 (1H, s). m/z 314.7 (MH$^+$).

Example 14

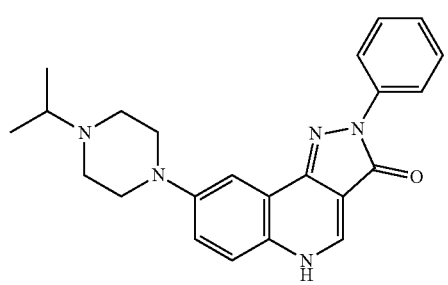

19b 8-(4-Isopropylpiperazin-1-yl)-2-phenyl-2,5-dihydro-pyrazolo[4,3-c]quinolin-3-one (19b): 23a was stirred with excess of N-isopropylpiperazine at 175° C. for 72 hours. The precipitates were collected by filtration and washed with ethyl acetate and purified using column chromatography to obtain title compound in 84% yield. $^1$H-NMR (DMSO-d6) δ (ppm): 1.01 (6H, d, J=6.03 Hz), 2.63 (4H, br), 2.70 (1H, m), 3.22 (4H, br), 7.13 (2H, brt, J=7.32 Hz), 7.42 (3H, m), 7.58 (1H, d, J=9.32 Hz), 8.23 (2H, d, J=8.54 Hz), 8.54 (1H, s). m/z 388.5 (MH$^+$).

Example 15

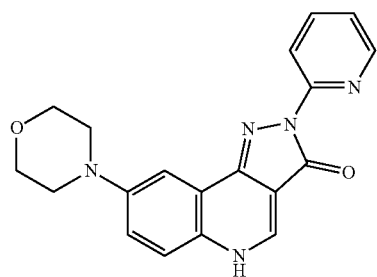

19c

8-Morpholin-4-yl-2-pyridin-2-yl-2,5-dihydro-pyrazolo[4,3-c]quinolin-3-one (19c): The title compound was obtained following procedure described in the synthesis of 19b using 23b and morpholine. $^1$H-NMR (DMSO-d6) δ (ppm): 3.22 (4H, br), 3.80 (4H, br), 7.20 (1H, ddd, J=7.32, 4.88, 0.98 Hz), 7.44 (2H, m), 7.58 (1H, d, J=7.57 Hz), 7.86 (1H, ddd, J=7.57, 1.19, 0.97 Hz), 8.24 (1H, d, J=8.30 Hz), 8.48 (1H, ddd, J=3.66, 1.95, 1.22 Hz), 8.60 (1H, s). m/z 348.6 (MH$^+$).

Example 16

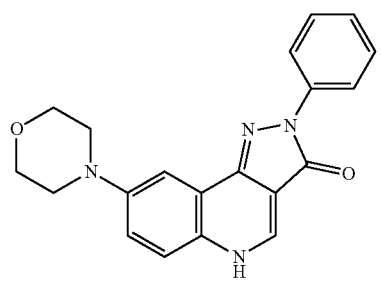

19d

8-Morpholin-4-yl-2-phenyl-2,5-dihydro-pyrazolo[4,3-c]quinolin-3-one (19d): The title compound was obtained following procedure described in the synthesis of 19b using 23a and morpholine. $^1$H-NMR (DMSO-d6) δ (ppm): 3.24 (4H, br), 3.77 (4H, br), 7.13 (1H, t, J=7.42 Hz), 7.38 (4H, m), 7.60 (1H, d, J=9.06 Hz), 8.23 (2H, dd, J=8.24, 1.65 Hz), 8.57 (1H, s). m/z 347.4 (MH$^+$).

Example 17

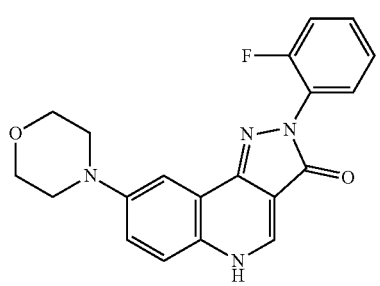

19e 2-(2-Fluorophenyl)-8-morpholin-4-yl-2,5-dihydro-pyrazolo[4,3-c]quinolin-3-one (19e): The title compound was obtained following procedure described in the synthesis of 19b using 23c and morpholine. $^1$H-NMR (DMSO-d6) δ (ppm): 3.21 (4H, br), 3.76 (4H, br), 7.2 (5H, m), 7.54 (1H, dt, J=7.97, 1.37 Hz), 7.62 (1H, d, J=8.79 Hz), 8.58 (1H, d, J=6.32 Hz). m/z 365.4 (MH$^+$).

Example 18

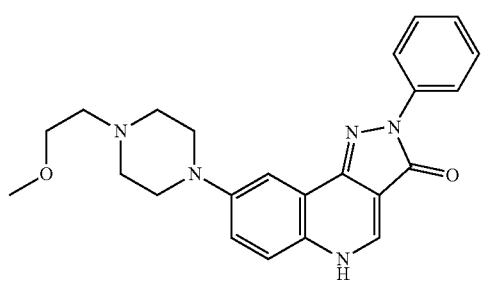

19f

8-[4-(2-Methoxyethyl)-piperazin-1-yl]-2-phenyl-2,5-dihydro-pyrazolo[4,3-c]quinolin-3-one (19f): The title compound was obtained following procedure described in the synthesis of 19b using 1-methoxyethylpiperazine. $^1$H-NMR (DMSO-d6) δ (ppm): 1.18 (3H, d, J=11.86 Hz), 1.21 (3H, d, J=11.72 Hz), 2.67 (2H, dd, J=11.72, 11.47 Hz), 3.72 (4H, br), 7.11 (2H, t, J=7.32 Hz), 7.39 (4H, m), 7.57 (1H, d, J=9.03 Hz), 8.21 (2H, m), 8.57 (1H, s). m/z 404.5 (MH$^+$).

Example 19

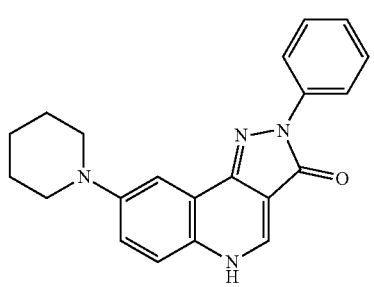

19g

2-Phenyl-8-piperidin-1-yl-2,5-dihydro-pyrazolo[4,3-c]quinolin-3-one (19 g): The title compound was obtained following procedure described in the synthesis of 19b using 23a and piperidine. $^1$H-NMR (DMSO-d6) δ (ppm): 1.1-1.4 (6H, m), 2.84 (2H, br), 3.15 (2H, br), 7.14 (1H, t, J=7.33 Hz), 7.41 (3H, m), 7.86 (1H, d, J=12.94 Hz), 8.20 (2H, dd, J=8.79, 1.22 Hz), 8.66 (1H, s), 8.80 (1H, br). m/z 345.4 (MH$^+$).

Example 20

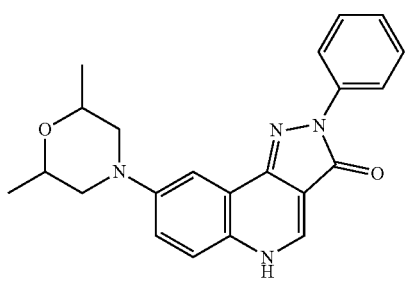

19h 8-(2,6-Dimethylmorpholin-4-yl)-2-phenyl-2,5-dihydro-pyrazolo[4,3-c]quinolin-3-one (19h): The title compound was obtained following procedures described in the synthesis of 19b using 2,6-dimethylmorpholine. $^1$H-NMR (DMSO-d6) δ (ppm): 2.54 (2H, t, J=5.62 Hz), 2.60 (4H, br), 3.24 (3H, s), 3.26 (4H, br), 3.47 (2H, t, J=5.62 Hz), 7.11 (2H, tt, J=7.32, 1.22 Hz), 7.41 (4H, m), 7.59 (1H, d, J=9.03 Hz), 8.20 (2H, dd, J=8.54, 1.22 Hz), 8.56 (1H, s). m/z 375.5 (MH$^+$).

Example 21

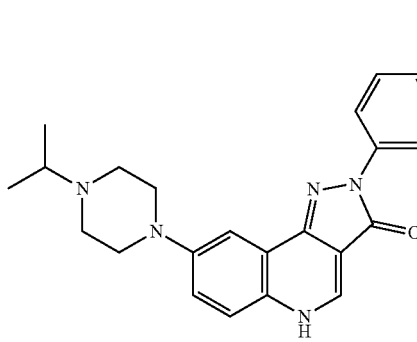

19i 8-(4-Isopropylpiperazin-1-yl)-2-(4-methoxyphenyl)-2,5-dihydro-pyrazolo[4,3-c]quinolin-3-one (19i): The title compound was obtained following procedure described in the synthesis of 19b using 23d. $^1$H-NMR (DMSO-d6) δ (ppm): 1.12 (6H, d, J=6.08 Hz), 3.20 (4H, br), 3.78 (4H, br), 3.76 (3H, s), 6.80 (2H, d, J=8.97 Hz), 7.44 (2H, m), 7.60 (1H, d, J=8.79 Hz), 7.91 (1H, d, J=9.07 Hz), 8.56 (1H, br), 9.33 (1H, s). m/z 418.4 (MH$^+$).

Example 22

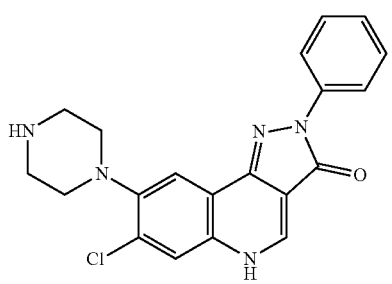

19j

7-Chloro-2-phenyl-8-piperazin-1-yl-2,5-dihydro-pyrazolo[4,3-c]quinolin-3-one (19j): The title compound was obtained following procedure described in the synthesis of 19b using 23e and piperazine. $^1$H-NMR (DMSO-d6) δ (ppm): 3.11 (4H, br), 3.33 (4H, br), 7.15 (1H, t, J=7.32 Hz), 7.41 (2H, dd, J=8.54, 7.32 Hz), 7.74 (2H, d, J=2.93 Hz), 8.20 (2H, dd, J=8.54, 1.22 Hz), 8.65 (1H, s). m/z 380.9 (MH$^+$).

Example 23

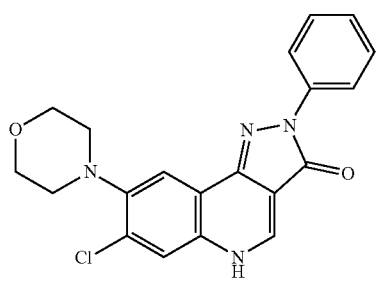

19k

7-Chloro-8-morpholin-4-yl-2-phenyl-2,5-dihydro-pyrazolo[4,3-c]quinolin-3-one (19k): The title compound was obtained following procedure described in the synthesis 19b using 23e and morpholine. $^1$H-NMR (DMSO-d6) δ (ppm): 3.08 (4H, br), 3.78 (4H, br), 7.18 (1H, tt, J=7.32, 1.32 Hz), 7.43 (2H, t, J=7.56 Hz), 7.78 (2H, d, J=2.44 Hz), 8.21 (2H, dd, J=8.54, 1.22 Hz), 8.71 (1H, s). m/z 381.8 (MH$^+$).

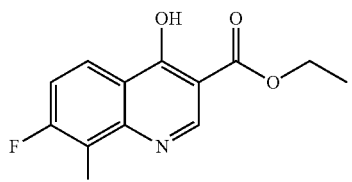

25a

Ethyl 7,8-difluoro-4-hydroxy-quinoline-3-carboxylate (25a): The title compound was prepared following the procedure described in Step 1 using 3,4-difluoroaniline instead of 4-nitroaniline. $^1$H-NMR (DMSO-d6) δ (ppm): 1.15 (3H, t, J=7.08 Hz), 4.1 (2H, q, J=7.08 Hz), 7.61 (1H, dd, J=8.30, 2.93 Hz), 7.68 (1H, dd, J=4.63, 9.03 Hz), 7.80 (1H, dd, J=9.27, 2.93 Hz), 8.56 (1H, s). m/z 254.2 (MH$^+$).

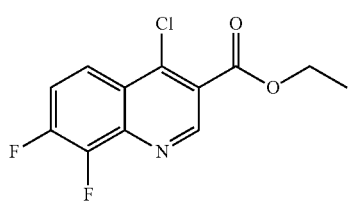

26a

Ethyl 4-chloro-7,8-difluoro-quinoline-3-carboxylate (26a): The title compound was prepared following the procedure described in Step 2 using 25a instead of 3. $^1$H-NMR (CDCl$_3$) δ (ppm): 1.47 (3H, t, J=7.08 Hz), 4.56 (2H, q, J=7.08 Hz), 7.72 (1H, d, J=8.79 Hz), 8.39 (1H, d, J=8.78 Hz), 9.23 (1H, s). m/z 272.7 (MH$^+$).

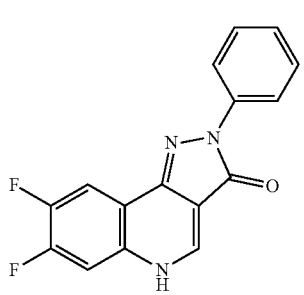

27a 7,8-Difluoro-2-phenyl-2,5-dihydro-pyrazolo-[4,3-c]quinolin-3-one (27a): The title compound was prepared following the procedure described for 4a using 26a. $^1$H-NMR (DMSO-d6) δ (ppm): 7.18 (1H, t, J=7.82 Hz), 7.43 (2H, dd, J=8.30, 7.33 Hz), 7.75 (1H, dd, J=11.22, 7.32 Hz), 8.18, 3H, m), 8.90 (1H, s). m/z 298.3 (MH$^+$).

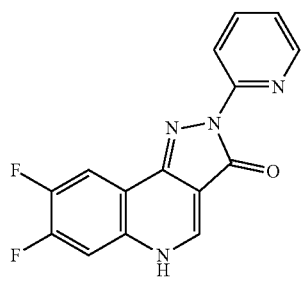

7,8-Difluoro-2-(2'-pyridyl)-2,5-dihydro-pyrazolo-[4,3-c]quinolin-3-one (27b): The title compound was prepared following the procedure described for 23b using 26. $^1$H-NMR (DMSO-d6) δ (ppm): 7.31 (1H, t, J=7.86 Hz), 7.73 (1H, dd, J=11.26, 7.14 Hz), 8.01 (1H, dt, J=8.79, 1.65 Hz), 8.16 (1H, t, J=8.24 Hz), 8.24 (1H, d, J=8.24 Hz), 8.50 (1H, d, J=3.85 Hz), 8.82 (1H, s). m/z 299.3 (MH$^+$).

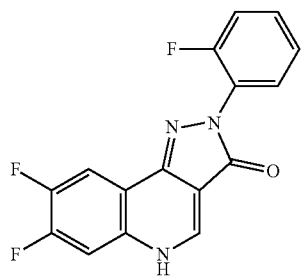

7,8-Difluoro-2-(2'-fluorophenyl)-2,5-dihydro-pyrazolo-[4,3-c]quinolin-3-one (27c): The title compound was prepared following the procedure described for 23b using 26 and 2-fluorophenylhydrazine.HCl. $^1$H-NMR (DMSO-d6) δ (ppm): 7.31 (3H, m), 7.54 (1H, dd, J=7.3, 6.0 Hz), 7.69 (1H, dd, J=11.1, 7.1 Hz), 8.06 (1H, dd, J=10.5, 8.4 Hz), 8.76 (1H, d, J=6.2 Hz). m/z 316.2 (MH$^+$).

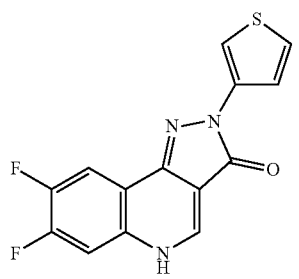

7,8-Difluoro-2-(thiophen-3-yl)-2,5-dihydro-pyrazolo-[4,3-c]quinolin-3-one (27d): 1.05 equiv. of methyl 3-hydrazin-thiophene-2-carboxylate was added to a solution of 3c in ethanol. After 1.5 hr of stirring at room temperature, the solution was concentrated in vacuo and residue was dissolved in chloroform and washed with aq. sodium bicarbonate solution, dried and concentrated in vacuo. The resulting solid was suspended in ethanol and stirred with 1N sodium hydroxide solution for 30 minutes, acidified with acetic acid and concentrated in vacuo. The solid was filtered, washed with water, dried and suspended in ethanol. 1N sodium hydroxide was added and the reaction mixture was refluxed for 1 hr, acidified with acetic acid and the crystals were collected by filtration. The yellow solid was combined with copper powder and quinoline and stirred at 190° C. for 1 hour. The copper was removed by filtration and the filtrate was mixed with 1N sodium hydroxide solution, followed by extraction with ether. The separated aqueous layer was treated with active charcoal, acidified with acetic acid to yield 41 as yellow solid. $^1$H-NMR (DMSO-d6) δ (ppm): 7.58 (1H, dd, J=5.22, 3.30 Hz), 7.69 (1H, dd, J=11.26, 7.14 Hz), 7.74 (1H, dd, J=5.22, 1.38 Hz), 7.80 (1H, m), 8.15 (1H, dd, J=10.7, 8.2 Hz), 8.77 (1H, d, J=6.2 Hz). m/z 304.2 (MH$^+$).

Example 24

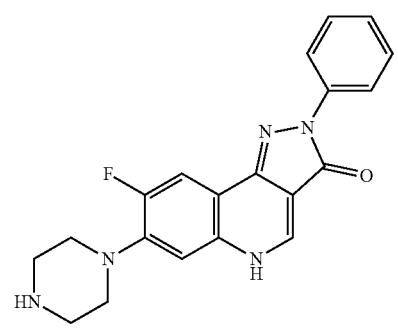

8-Fluoro-2-phenyl-7-piperazin-1-yl-2,5-dihydro-pyrazolo[4,3-c]quinolin-3-one (28a): The title compound was obtained following procedure described in the synthesis of 19b using 27a and piperazine. $^1$H-NMR (DMSO-d6) δ (ppm): 2.92 (4H, brm), 3.04 (4H, brm), 7.11 (1H, t, J=7.41 Hz), 7.23 (1H, d, J=7.97 Hz), 7.39 (2H, m), 7.79 (1H, d, J=13.18 Hz), 8.21 (2H, dd, J=8.52, 1.10 Hz), 8.62 (1H, s). m/z 364.4 (MH$^+$).

Example 25

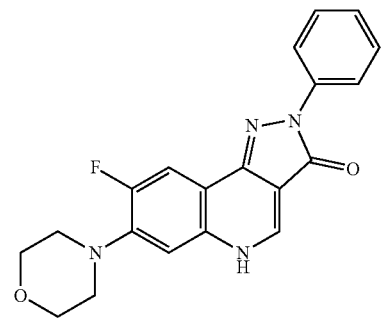

8-Fluoro-7-morpholin-4-yl-2-phenyl-2,5-dihydro-pyrazolo[4,3-c]quinolin-3-one (28b): The title compound was obtained following procedure described in the synthesis of 28a using 27a and morpholine. $^1$H-NMR (DMSO-d6) δ (ppm): 3.11 (4H, br), 3.80 (4H, m), 7.11 (1H, t, J=7.08 Hz), 7.24 (1H, d, J=7.81 Hz), 7.38 (2H, t, J=7.38 Hz), 7.80 (1H, d, J=12.93 Hz), 8.17 (2H, dd, J=8.30 Hz), 8.67 (1H, s). m/z 365.4 (MH$^+$).

Example 26

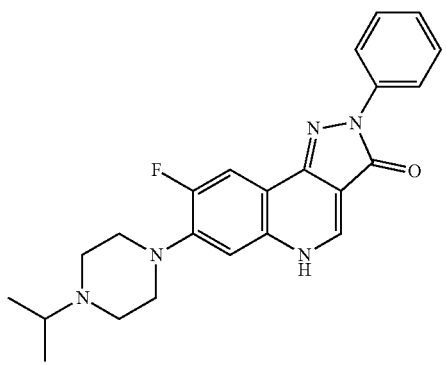

28c

8-Fluoro-7-(4-isopropylpiperazin-1-yl)-2-phenyl-2,5-dihydro-pyrazolo [4,3-c]quinolin-3-one (28c): The title compound was obtained following procedure described in the synthesis of 28a using 27a and 1-isopropylpiperazine. $^1$H-NMR (DMSO-d6) δ (ppm): 1.03 (6H, d, J=6.04 Hz), 2.70 (4H, br), 3.02 (1H, m), 3.13 (4H, m), 7.13 (1H, t, J=7.41 Hz), 7.22 (1H, d, J=7.69 Hz), 7.40 (2H, t, J=7.97 Hz), 7.77 (1H, d, J=13.19 Hz), 8.19 (2H, d, J=7.42 Hz), 8.66 (1H, s). m/z 406.5 (MH$^+$).

Example 27

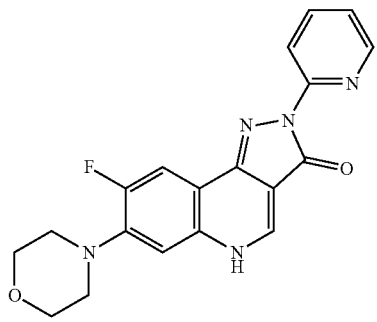

28d

8-Fluoro-7-(morpholin-4-yl)-2-pyridin-2-yl-2,5-dihydro-pyrazolo[4,3-c]quinolin-3-one (28d): The title compound was obtained following procedure described in the synthesis of 28a using 27b and morpholine. $^1$H-NMR (DMSO-d6) δ (ppm): 3.10 (4H, br), 3.77 (4H, m), 7.18 (1H, t, J=7.08 Hz), 7.25 (1H, d, J=7.92 Hz), 7.79 (1H, d, J=13.18 Hz), 7.86 (1H, m), 8.20 (1H, d, J=8.24 Hz), 8.46 (1H, m), 8.66 (1H, d, J=1.65 Hz). m/z 366.4 (MH$^+$).

Example 28

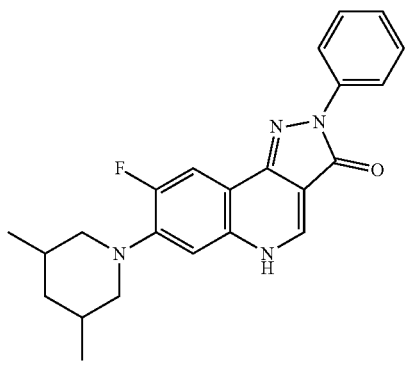

28e 7-(3,5-Dimethylpiperidin-1-yl)-8-fluoro-2-phenyl-2,5-dihydro-pyrazolo[4,3-c]quinolin-3-one (28e): The title compound was prepared following the procedure described in the synthesis of 28a using 27a and 3,5-dimethylpiperidine. $^1$H-NMR (DMSO-d6) δ (ppm): 0.99 (6H, d, J=6.33 Hz), 1.80 (4H, br), 2.47 (2H, t, J=8.62 Hz), 3.46 (2H, brd, J=11.81 Hz), 7.13 (1H, m), 7.26 (1H, d, J=7.97 Hz), 7.40 (2H, t, J=7.69 Hz), 7.79 (1H, d, J=13.18 Hz), 8.19 (2H, d, J=7.69 Hz), 8.65 (1H, s). m/z 391.5 (MH$^+$).

Example 29

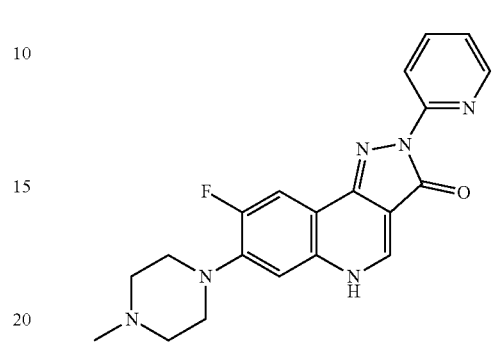

28f

8-Fluoro-7-(4-methylpiperazin-1-yl)-2-pyridin-2-yl-2,5-dihydro-pyrazolo[4,3-c]quinolin-3-one (28f): The title compound was obtained following procedure described in the synthesis of 28a using 27b and 1-methylpiperazine. $^1$H-NMR (DMSO-d6) δ (ppm): 2.46 (3H, s), 3.09 (4H, br), 3.29 (4H, brm), 7.16 (1H, m), 7.22 (1H, d, J=8.24 Hz), 7.84 (2H, m), 8.26 (1H, dd, J=8.24, 0.83 Hz), 8.45 (1H, m), 8.56 (1H, s). m/z 379.4 (MH$^+$).

Example 30

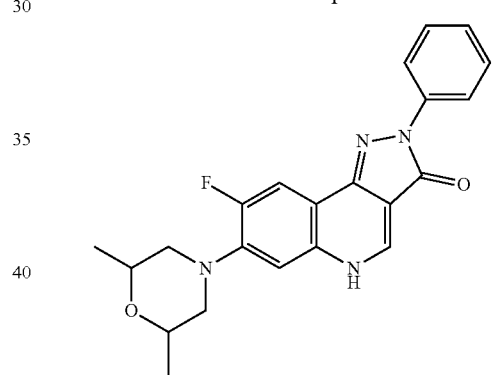

28g 7-(2,6-Dimethylmorpholin-4-yl)-8-fluoro-2-phenyl-2,5-dihydro-pyrazolo[4,3-c]quinolin-3-one (28g): The title compound was prepared following the procedure described in the synthesis of 28a using 27a and 2,6-dimethylmorpholine. $^1$H-NMR (DMSO-d6) δ (ppm): 1.15 (6H, d, J=6.73 Hz), 2.40 (2H, brm), 3.41 (2H, d, J=10.99 Hz), 3.76 (2H, brm), 7.13 (1H, m), 7.26 (1H, d, J=7.69 Hz), 7.41 (2H, t, J=7.42 Hz), 7.83 (2H, d, J=12.91 Hz), 8.19 (2H, m), 8.66 (1H, s). m/z 393.4 (MH$^+$).

Example 31

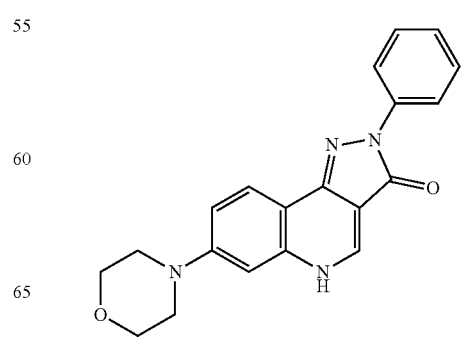

28h

7-Morpholin-4-yl-2-phenyl-2,5-dihydro-pyrazolo[4,3-c]quinolin-3-one (28h): The title compound was prepared following the procedure described in Step 3 using ethyl-4-chloro-7-morpholinoquinoline-3-carboxylate instead of 4a. $^1$H-NMR (DMSO-d6) δ (ppm): 3.25 (4H, br), 3.77 (4H, m), 7.01 (1H, d, J=2.95 Hz), 7.12 (1H, t, J=7.32 Hz), 7.29 (1H, dd, J=9.52, 2.19 Hz), 7.40 (2H, t, J=7.32 Hz), 8.00 (1H, d, J=9.03 Hz), 8.17 (2H, d, J=9.03 Hz), 8.59 (1H, s). m/z 347.4 (MH$^+$).

Example 32

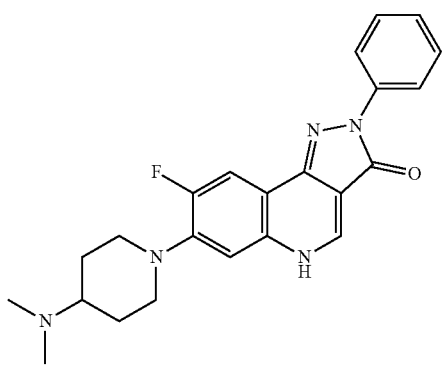

7-(4-Dimethylaminopiperidin-1-yl)-8-fluoro-2-phenyl-2,5-dihydro-pyrazolo[4,3-c]quinolin-3-one (28i): The title compound was prepared following the procedure described in the synthesis of 28a using 27a and 4-dimethylaminopiperidine. $^1$H-NMR (DMSO-d6) δ (ppm): 1.56 (2H, brm), 1.89 (2H, brm), 2.22 (6H, s), 2.74 (2H, brm), 3.13 (1H, brm), 3.52 (2H, brm), 7.10 (1H, m), 7.22 (1H, d, J=7.96 Hz), 7.40 (2H, t, J=7.42 Hz), 7.76 (2H, d, J=2.91 Hz), 8.20 (2H, m), 8.64 (1H, s). m/z 406.4 (MH$^+$).

Example 33

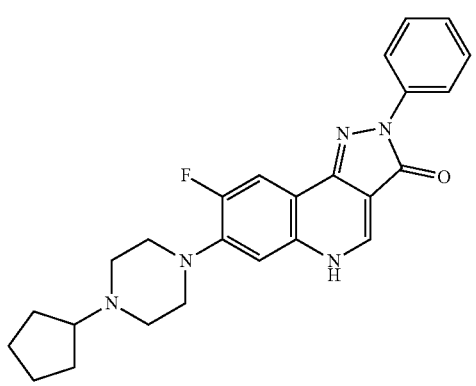

7-(4-Cyclopentylpiperazin-1-yl)-8-fluoro-2-phenyl-2,5-dihydro-pyrazolo[4,3-c]quinolin-3-one (28j): The title compound was prepared following the procedure described in the synthesis of 28a using 27a and 1-cyclopentylpiperazine. $^1$H-NMR (DMSO-d6) δ (ppm): 1.20-1.85 (9H, brm), 2.58 (4H, brm), 3.11 (4H, brm), 7.10 (1H, m), 7.22 (1H, d, J=7.94 Hz), 7.40 (2H, m), 7.76 (1H, d, J=2.91 Hz), 8.19 (2H, m), 8.64 (1H, s). m/z 431.2 (MH$^+$).

Example 34

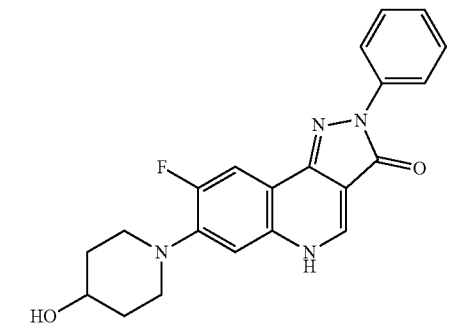

8-Fluoro-7-(4-hydroxypiperidin-1-yl)-2-phenyl-2,5-dihydro-pyrazolo[4,3-c]quinolin-3-one (28k): The title compound was prepared following the procedure described in the synthesis of 28a using 27a and 4-hydroxypiperidine. $^1$H-NMR (DMSO-d6) δ (ppm): 1.54 (2H, brm), 1.87 (2H, brm), 2.85 (2H, brm), 3.20 (1H, m), 3.64 (1H, brm), 4.74 (1H, brd, J=3.84 Hz), 7.10 (1H, m), 7.22 (1H, d, J=7.97 Hz), 7.40 (2H, m), 7.76 (1H, d, J=2.90 Hz), 8.20 (2H, m), 8.64 (1H, s). m/z 379.2 (MH$^+$).

Example 35

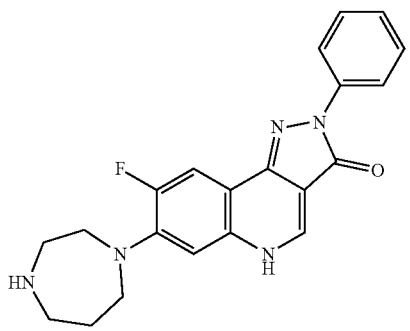

8-Fluoro-7-(perhydro[1,4]-diazepin-1-yl)-2-phenyl-2,5-dihydro-pyrazolo[4,3-c]quinolin-3-one (28l): The title compound was prepared following the procedure described in the synthesis of 28a using 27a and homopiperazine. $^1$H-NMR (DMSO-d6) δ (ppm): 1.98 (2H, brm), 2.48 (2H, brm), 2.67 (2H, brm), 3.45 (4H, brm), 7.15 (2H, m), 7.40 (2H, m), 7.76 (1H, d, J=2.91 Hz), 8.20 (2H, m), 8.64 (1H, s). m/z 378.2 (MH$^+$).

Example 36

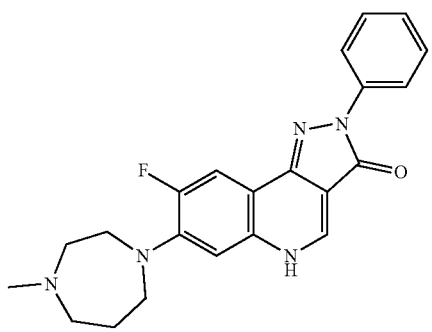

8-Fluoro-7-(4-methylperhydro[1,4]-diazepin-1-yl)-2-phenyl-2,5-dihydro-pyrazolo[4,3-c]quinolin-3-one (28m): The title compound was prepared following the procedure described in the synthesis of 28a using 27a and 1-methylperhydro[1,4]-diazepine. ¹H-NMR (DMSO-d6) δ (ppm): 1.98 (2H, brm), 2.27 (3H, s), 2.68 (4H, brm), 3.24 (4H, brm), 7.15 (2H, m), 7.40 (2H, m), 7.76 (1H, d, J=2.91 Hz), 8.20 (2H, m), 8.64 (1H, s). m/z 392.2 (MH⁺).

Example 37

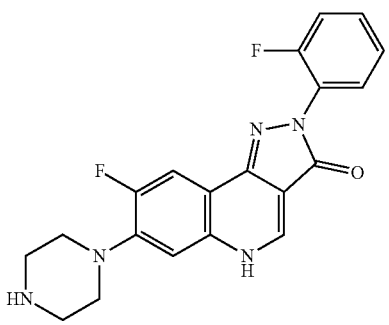

28n

8-Fluoro-2-(2-fluorophenyl)-7-(piperazin-1-yl)-2,5-dihydro-pyrazolo[4,3-c]quinolin-3-one (28n): The title compound was prepared following the procedure described in the synthesis of 28a using 27c and piperazine. ¹H-NMR (CD₃OD) δ (ppm): 3.01 (4H, brm), 3.34 (4H, brm), 7.05 (1H, d, J=7.7 Hz), 7.16 (2H, m), 7.31 (1H, m), 7.40 (1H, m), 7.66 (1H, d, J=13.1 Hz), 8.44 (1H, s). m/z 382.2

Example 38

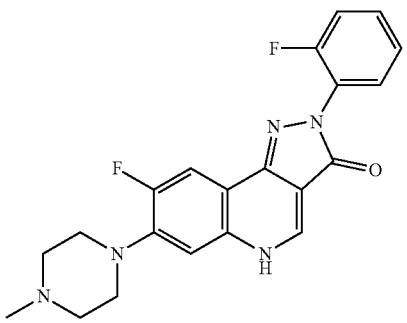

28o 8-fluoro-2-(2-fluorophenyl)-7-(4-methylpiperazin-1-yl)-2,5-dihydro-pyrazolo[4,3-c]quinolin-3-one (28o): The title compound was prepared following the procedure described in the synthesis of 28a using 27c and 1-methylpiperazine. ¹H-NMR (CD₃OD) δ (ppm): 2.23 (3H, s), 2.48 (4H, brm), 2.68 (4H, brm), 7.05 (1H, d, J=7.7 Hz), 7.16 (2H, m), 7.31 (1H, m), 7.40 (1H, m), 7.66 (1H, d, J=13.1 Hz), 8.44 (1H, s). m/z 396.2

Example 39

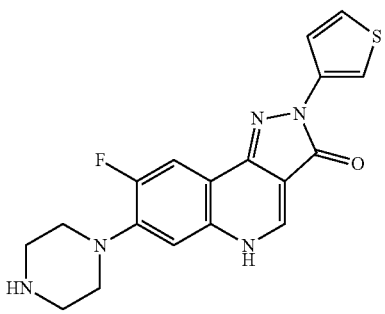

28p 8-fluoro-7-(piperazin-1-yl)-2-(thiophen-3-yl)-2,5-dihydro-pyrazolo[4,3-c]quinolin-3-one (28p): The title compound was prepared following the procedure described in the synthesis of 28a using 27d and piperazine. ¹H-NMR (DMSO-d6) δ (ppm): 2.92 (4H, brm), 3.05 (4H, brm), 7.21 (1H, m), 7.58 (1H, m), 7.79 (3H, m), 8.67 (1H, m). m/z 370.2

Example 40

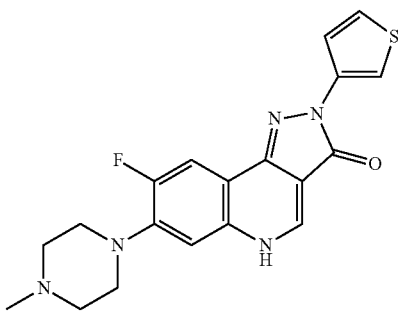

28q 8-fluoro-7-(4-methylpiperazin-1-yl)-2-(thiophen-3-yl)-2,5-dihydro-pyrazolo[4,3-c]quinolin-3-one (28q): The title compound was prepared following the procedure described in the synthesis of 28a using 27d and 1-methylpiperazine. ¹H-NMR (DMSO-d6) δ (ppm): 2.28 (3H, s), 2.64 (4H, brm), 3.22 (4H, brm), 7.21 (1H, m), 7.58 (1H, m), 7.79 (3H, m), 8.67 (1H, m). m/z 384.2

Example 41

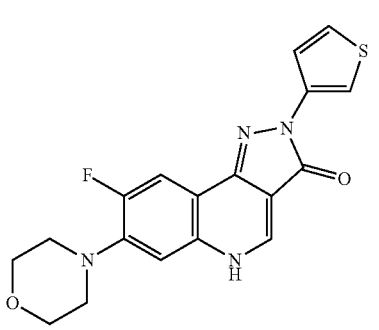

28r 8-fluoro-7-(morpholin-4-yl)-2-(thiophen-3-yl)-2,5-dihydro-pyrazolo[4,3-c]quinolin-3-one (28r): The title compound was prepared following the procedure described in the synthesis of 28a using 27d and morpholine. ¹H-NMR (DMSO-d6) δ (ppm): 3.11 (4H, brm), 3.79 (4H, brm), 7.21 (1H, m), 7.58 (1H, m), 7.79 (3H, m), 8.67 (1H, m). m/z 371.2

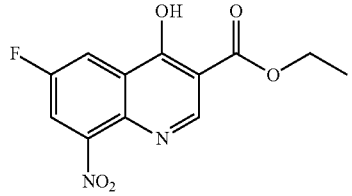

35

Ethyl 6-fluoro-4-hydroxy-8-nitro-quinoline-3-carboxylate (35): The title compound was prepared following the procedure described in Step 1 using 4-fluoro-2-nitroaniline instead of 4-nitroaniline. ¹H-NMR (DMSO-d6) δ (ppm): 1.26 (3H, t, J=7.14 Hz), 4.20 (2H, q, J=7.15 Hz), 8.31 (1H, dd, J=8.24, 3.02 Hz), 8.57 (1H, brs), 8.64 (1H, dd, J=8.24, 3.02 Hz). m/z 281.3 (MH⁺).

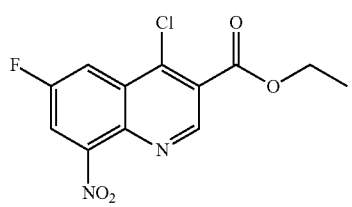

36

Ethyl 4-chloro-6-fluoro-8-nitro-quinoline-3-carboxylate (36): The title compound was prepared following the procedure described in Step 2 using 35. ¹H-NMR (CDCl₃) δ (ppm): 1.46 (3H, t, J=7.14 Hz), 4.55 (2H, q, J=7.14 Hz), 7.94 (1H, dd, J=7.14, 2.75 Hz), 8.29 (1H, dd, J=8.79, 2.74 Hz), 9.27 (1H, s). m/z 299.7 (MH⁺).

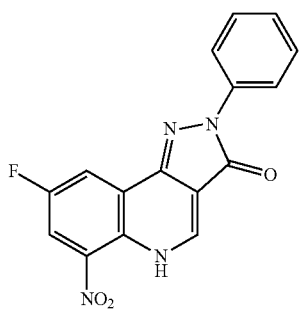

37

8-Fluoro-6-nitro-2-phenyl-2,5-dihydropyrazolo-[4,3-c]quinolin-3-one (37): The title compound was prepared following the procedure described in Step 3 using 36. m/z 325.3 (MH⁺).

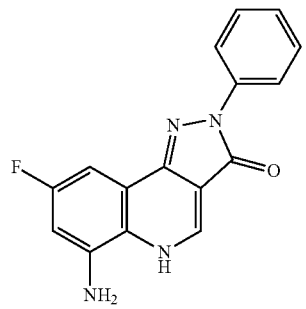

38

6-Amino-8-fluoro-2-phenyl-2,5-dihydropyrazolo-[4,3-c]quinolin-3-one (38): The title compound was prepared following the procedure described in Step 4 using 37. m/z 295.3 (MH⁺).

Example 42

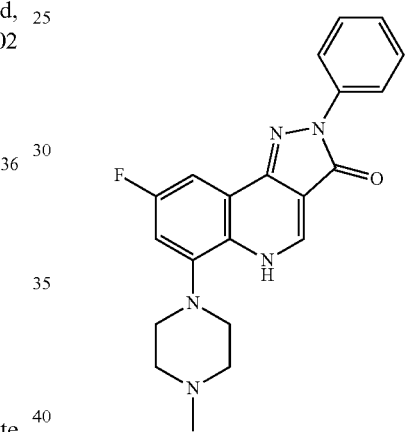

39

8-Fluoro-6-(4-methylpiperazin-1-yl)-2-phenyl-2,5-dihydro-pyrazolo[4,3-c]quinolin-3-one (39): The title compound was prepared following the procedure in Step 5 using 38. ¹H-NMR (DMSO-d6) δ (ppm): 2.40 (3H, s), 3.18 (4H, brm), 3.67 (4H, brm), 7.16 (1H, m), 7.39 (2H, m), 7.48 (1H, dd, J=9.17, 2.74 Hz), 7.69 (2H, dd, J=8.51, 2.75 Hz), 8.19 (2H, d, J=7.70 Hz), 8.46 (1H, d, J=6.59 Hz). m/z 378.4 (MH⁺).

Example 43

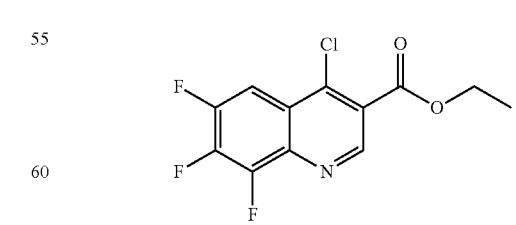

42

Ethyl 4-chloro-6,7,8-trifluoro-quinoline-3-carboxylate (42): The title compound was prepared following the procedure described in Step 2 using ethyl 4-hydroxy-6,7,8-trifluoro-quinoline-3-carboxylate instead of 3. ¹H-NMR (CDCl₃) δ (ppm): 1.44 (3H, t, J=7.14 Hz), 4.55 (2H, q, J=7.14 Hz), 8.04 (1H, m), 9.22 (1H, s). m/z 290.7 (MH⁺).

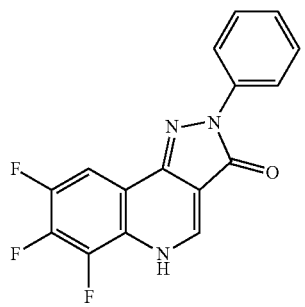

43a 6,7,8-Trifluoro-2-phenyl-2,5-dihydro-pyrazolo-[4,3-c]quinolin-3-one (43a): The title compound was prepared following the procedure described for 4a using 42. ¹H-NMR (DMSO-d6) δ (ppm): 7.22 (1H, m), 7.44 (2H, m), 8.05 (1H, m), 8.18, 3H, m), 8.16 (2H, m), 8.60 (1H, s). m/z 316.2 (MH⁺).

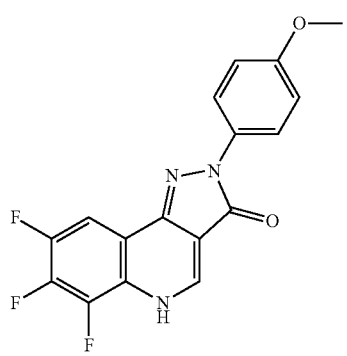

43b 6,7,8-Trifluoro-2-(4-methoxyphenyl)-2,5-dihydro-pyrazolo-[4,3-c]quinolin-3-one (43b): The title compound was prepared following the procedure described for 4a using 42 and 4-methoxyphenylhydrazine. m/z 346.2 (MH⁺).

Example 44

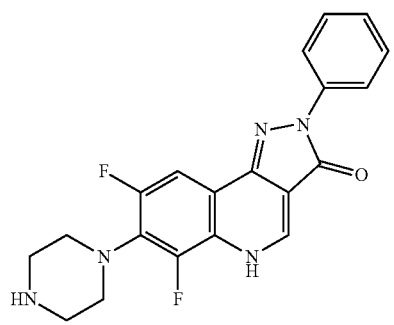

44a 6,8-Difluoro-2-phenyl-7-piperazin-1-yl-2,5-dihydro-pyrazolo[4,3-c]quinolin-3-one (44a): The title compound was obtained following procedure described in the synthesis of 19b using 43a and piperazine. ¹H-NMR (DMSO-d6) δ (ppm): 3.05 (4H, brm), 3.32 (4H, brm), 7.02 (1H, m), 7.36 (3H, m), 7.54 (1H, d, J=12.0 Hz), 8.28 (2H, d, J=7.8 Hz), 8.40 (1H, s). m/z 382.4 (MH⁺).

Example 45

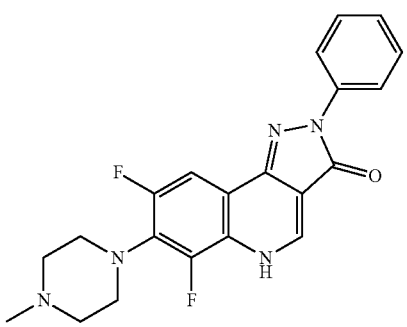

44b 6,8-Difluoro-7-(4-methyl-piperazin-1-yl)-2-phenyl-2,5-dihydro-pyrazolo [4,3-c]quinolin-3-one (44b): The title compound was obtained following procedure described in the synthesis of 19b using 43a and 1-methylpiperazine. ¹H-NMR (DMSO-d6) δ (ppm): 2.33 (3H, s), 2.64 (4H, brm), 3.24 (4H, brm), 7.15 (1H, m), 7.38 (3H, m), 8.18 (2H, m), 8.47 (1H, s). m/z 396.4 (MH⁺).

Example 46

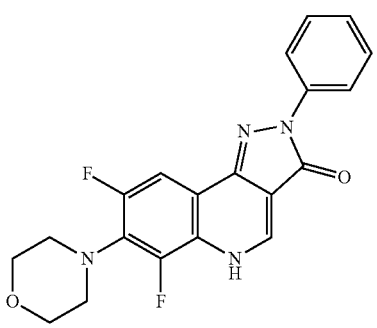

44c 6,8-Difluoro-7-(morpholin-4-yl)-2-phenyl-2,5-dihydro-pyrazolo[4,3-c]quinolin-3-one (44c): The title compound was obtained following procedure described in the synthesis of 19b using 43a and morpholine. ¹H-NMR (DMSO-d6) δ (ppm): 3.17 (4H, brm), 3.78 (4H, brm), 7.15 (1H, m), 7.42 (3H, m), 8.17 (2H, m), 8.49 (1H, s). m/z 383.4 (MH⁺).

Example 47

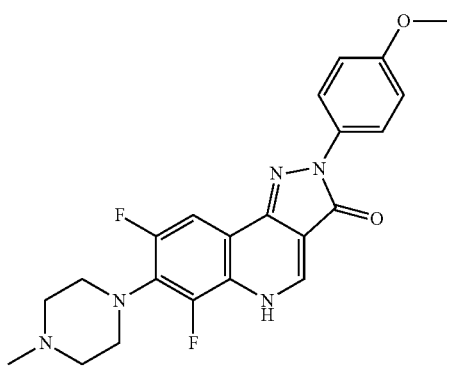

44d 6,8-Difluoro-2-(4-methoxyphenyl)-7-(4-methylpiperazin-1-yl)-2,5-dihydro-pyrazolo[4,3-c]quinolin-3-one (44d): The title compound was obtained following procedure described in the synthesis of 19b using 43b and 1-methylpiperazine. ¹H-NMR (DMSO-d6) δ (ppm): 2.28 (3H, s) 2.75 (2H, brm), 2.82 (2H, brm), 3.09 (4H, brm), 3.75 (3H, s), 6.99 (2H, d, J=9.0 Hz), 7.45 (1H, m), 8.06 (2H, d, J=9.0 Hz), 8.33 (1H, s). m/z 426.2 (MH⁺).

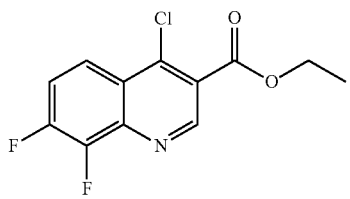

46

Ethyl 4-chloro-7,8-difluoro-quinoline-3-carboxylate (46): The title compound was prepared following the procedure described in Step 2 using Ethyl-7,8-difluoro-4-hydroxy-quinoline-3-carboxylate instead of 3. ¹H-NMR (CDCl₃) δ (ppm): 1.46 (3H, t, J=7.14 Hz), 4.52 (2H, q, J=7.14 Hz), 7.60 (1H, m), 8.24 (1H, m), 9.25 (1H, s). m/z 272.7 (MH⁺).

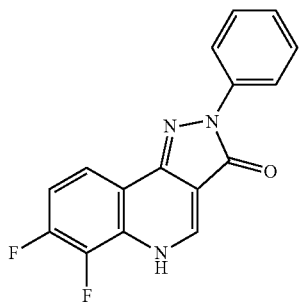

47a 6,7-Difluoro-2-phenyl-2,5-dihydro-pyrazolo-[4,3-c]quinolin-3-one (47a): The title compound was prepared following the procedure described for 4a using 46. ¹H-NMR (DMSO-d6) δ (ppm): 7.17 (1H, m), 7.44 (2H, m), 8.04 (1H, ddd, J=9.07, 5.22, 2.20 Hz), 8.17, 2H, m), 8.56 (1H, s). m/z 298.3 (MH⁺).

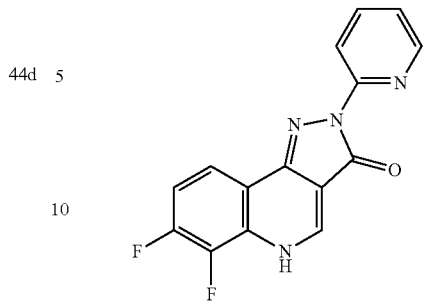

47b 6,7-Difluoro-2-(2-pyridyl)-2,5-dihydro-pyrazolo-[4,3-c]quinolin-3-one (47b): The title compound was prepared following the procedure described for 4a using 46 and pyridyl-2-hydrazine. ¹H-NMR (DMSO-d6) δ (ppm): 7.24 (1H, ddd, J=7.42, 4.94, 1.10 Hz), 7.60 (1H, m), 7.90 (1H, m), 8.02 (1H, m), 8.18 (1H, d, J=8.24 Hz), 8.49 (1H, ddd, J=4.95, 1.92, 0.83 Hz), 8.57 (1H, s). m/z 299.3 (MH⁺).

Example 48

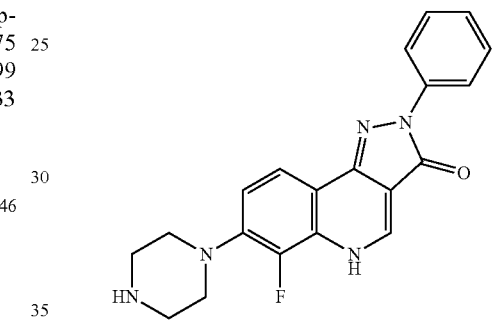

48a

6-Fluoro-2-phenyl-7-piperazin-1-yl-2,5-dihydro-pyrazolo[4,3-c]quinolin-3-one (48a): The title compound was obtained following procedure described in the synthesis of 19b using 47a and piperazine. ¹H-NMR (DMSO-d6) δ (ppm): 3.03 (4H, brm), 3.14 (4H, brm), 7.08 (1H, m), 7.17 (1H, t, J=8.52 Hz), 7.36 (2H, m), 7.87 (1H, dd, J=8.79, 1.37 Hz), 8.23 (2H, ddd, J=7.42, 1.65, 1.37 Hz), 8.41 (1H, s). m/z 364.3 (MH⁺).

Example 49

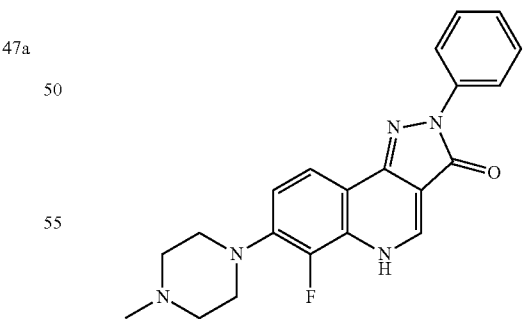

48b

6-Fluoro-7-(4-methyl-piperazin-1-yl)-2-phenyl-2,5-dihydro-pyrazolo [4,3-c]quinolin-3-one (48b): The title compound was obtained following procedure described in the synthesis of 19b using 47a and 1-methylpiperazine. ¹H-NMR (DMSO-d6) δ (ppm): 2.24 (3H, s), 2.53 (4H, brm), 3.18 (4H, brm), 7.13 (1H, m), 7.26 (1H, t, J=8.79 Hz), 7.42 (2H, m), 7.90 (1H, dd, J=8.79, 1.37 Hz), 8.23 (2H, ddd, J=7.42, 1.65, 1.37 Hz), 8.41 (1H, s). m/z 378.4 (MH⁺).

Example 50

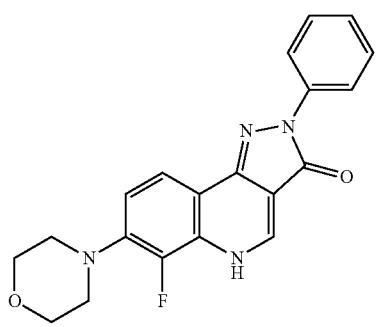

48c

6-Fluoro-7-(morpholin-4-yl)-2-phenyl-2,5-dihydro-pyrazolo[4,3-c]quinolin-3-one (48c): The title compound was obtained following procedure described in the synthesis of 19b using 47a and morpholine. $^1$H-NMR (DMSO-d6) δ (ppm): 3.16 (4H, brm), 3.76 (4H, brm), 7.11 (1H, m), 7.26 (1H, t, J=8.79 Hz), 7.41 (2H, m), 7.93 (1H, dd, J=8.79, 1.33 Hz), 8.17 (2H, m), 8.42 (1H, s). m/z 365.3 (MH$^+$).

Example 51

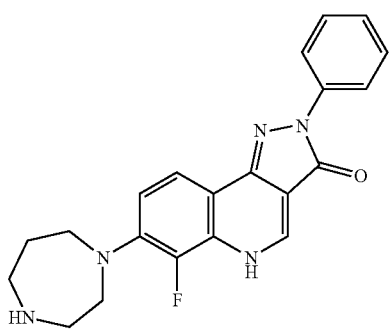

48d

6-Fluoro-7-(perhydro[1,4]-diazepine-1-yl)-2-phenyl-2,5-dihydro-pyrazolo[4,3-c]quinolin-3-one (48d): The title compound was obtained following procedure described in the synthesis of 19b using 47a and perhydro[1,4]-diazepine. $^1$H-NMR (DMSO-d6) δ (ppm): 1.96 (2H, brm), 2.98 (2H, brm), 3.10 (2H, brm), 3.53 (4H, brm), 7.10 (2H, m), 7.39 (2H, m), 7.78 (1H, d, J=8.79 Hz), 8.23 (2H, m), 8.36 (1H, s). m/z 378.3 (MH$^+$).

Example 52

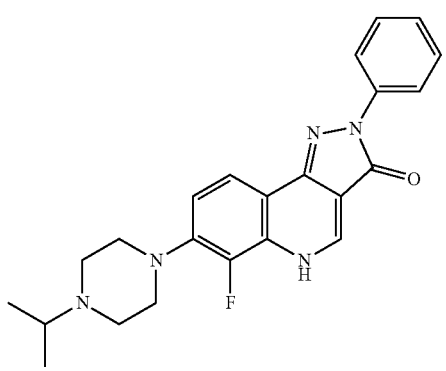

48e

6-Fluoro-7-(4-iso-propylpiperazin-1-yl)-2-phenyl-2,5-dihydro-pyrazolo [4,3-c]quinolin-3-one (48e): The title compound was obtained following procedure described in the synthesis of 19b using 47a and 1-iso-propylpiperazine. $^1$H-NMR (DMSO-d6) δ (ppm): 1.02 (6H, d, J=6.59 Hz), 2.75 (4H, brm), 2.82 (1H, m), 3.24 (4H, brm), 7.12 (1H, m), 7.41 (3H, m), 8.08 (1H, m), 8.18 (2H, m), 8.42 (1H, s). m/z 406.3 (MH$^+$).

Example 53

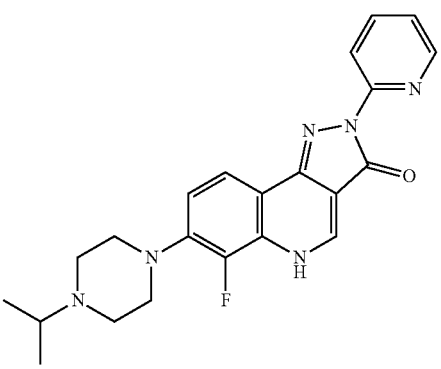

48f

6-Fluoro-7-(4-iso-propylpiperazin-1-yl)-2-(2'-pyridyl)-2,5-dihydro-pyrazolo[4,3-c]quinolin-3-one (48f): The title compound was obtained following procedure described in the synthesis of 19b using 47b and morpholine. $^1$H-NMR (DMSO-d6) δ (ppm): 3.18 (4H, brm), 3.80 (4H, brm), 7.19 (1H, dd, J=7.2, 4.9 Hz), 7.25 (1H, t, J=8.5 Hz), 7.84 (1H, dd, J=8.5, 2.0 Hz), 7.88 (1H, dd, J=8.6, 2.07 Hz), 8.18 (1H, d, J=8.4 Hz), 8.43 (1H, s), 8.47 (1H, m). m/z 365.3 (MH$^+$).

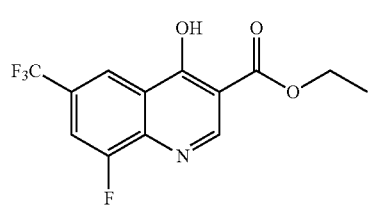

49

Ethyl 8-fluoro-4-hydroxy-6-trifluoromethyl-quinoline-3-carboxylate (49): The title compound was prepared following the procedure described in Step 1 using 2-fluoro-4-trifluoromethyl-aniline instead of 4-nitroaniline. $^1$H-NMR (DMSO-d6) δ (ppm): 1.25 (3H, t, J=7.14 Hz), 4.11 (2H, q, J=7.14 Hz), 8.00 (2H, m), 8.70 (1H, s). m/z 304.2 (MH$^+$).

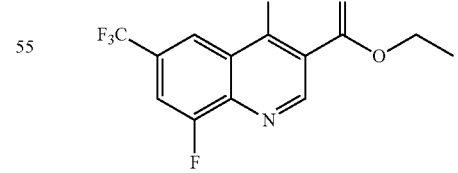

50

Ethyl 4-chloro-8-fluoro-6-trifluoromethyl-quinoline-3-carboxylate (50): The title compound was prepared following the procedure described in Step 2 using 49 instead of 3. $^1$H-NMR (CDCl$_3$) δ (ppm): 1.47 (3H, t, J=7.14 Hz), 4.56 (2H, q, J=7.14 Hz), 8.16 (1H, d, J=10.89 Hz), 8.48 (1H, d, J=6.59 Hz), 9.24 (1H, s). m/z 322.7 (MH$^+$).

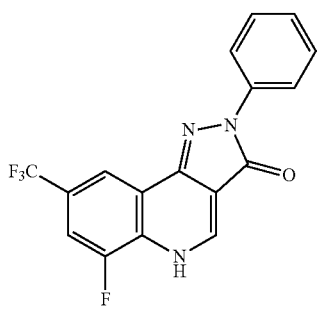

51

6-Fluoro-2-phenyl-8-trifluoromethyl-2,5-dihydro-pyrazolo-[4,3-c]quinolin-3-one (51): The title compound was prepared following the procedure described for 4a using 50. $^1$H-NMR (DMSO-d6) δ (ppm): 7.18 (1H, m), 7.21 (2H, m), 8.17 (4H, m), 8.88 (1H, s). m/z 348.3 (MH$^+$).

Example 54

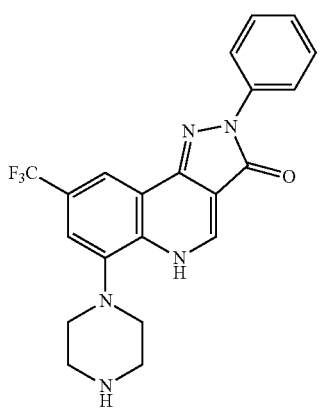

52a

2-Phenyl-6-piperazin-1-yl-8-trifluoromethyl-2,5-dihydro-pyrazolo[4,3-c]quinolin-3-one (52a): The title compound was obtained following procedure described in the synthesis of 19b using 51 and piperazine. $^1$H-NMR (DMSO-d6) δ (ppm): 3.04 (4H, brm), 3.31 (4H, brm), 7.07 (1H, m), 7.40 (2H, m), 7.93 (1H, s), 8.09 (1H, s), 8.28 (2H, m), 8.61 (1H, s). m/z 414.3 (MH$^+$).

Example 55

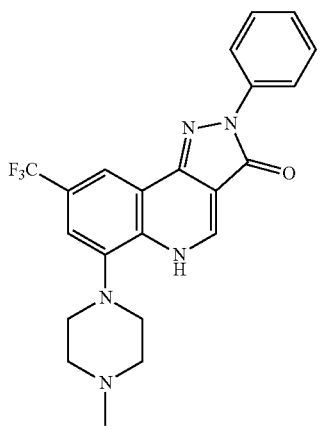

52b

2-Phenyl-6-(4-methylpiperazin-1-yl)-8-trifluoromethyl-2,5-dihydro-pyrazolo[4,3-c]quinolin-3-one (52b): The title compound was obtained following procedure described in the synthesis of 19b using 51 and 4-methylpiperazine. $^1$H-NMR (DMSO-d6) δ (ppm): 2.25 (3H, s), 2.55 (4H, brm), 3.01 (4H, brm), 7.16 (1H, m), 7.45 (2H, t, J=7.96 Hz), 8.01 (1H, s), 8.19 (1H, s), 8.22 (2H, m), 8.80 (1H, s). m/z 428.3 (MH$^+$).

Example 56

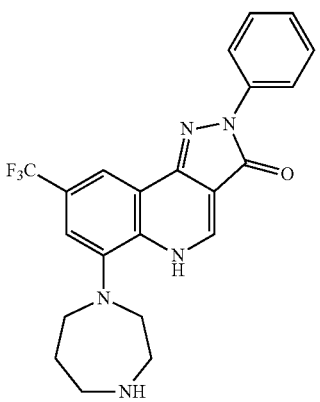

52c

2-Phenyl-6-(perhydro[1,4]-diazepine-1-yl)-8-trifluoromethyl-2,5-dihydro-pyrazolo[4,3-c]quinolin-3-one (52c): The title compound was obtained following procedure described in the synthesis of 19b using 51 and perhydro[1,4]-diazepine. $^1$H-NMR (DMSO-d6) δ (ppm): 1.94 (2H, brm), 2.20 (2H, brm), 3.17 (4H, brm), 3.38 (2H, brm), 7.17 (1H, m), 7.43 (2H, t, J=7.96 Hz), 8.04 (1H, s), 8.20 (1H, m), 8.26 (2H, s), 8.80 (1H, s). m/z 428.3 (MH$^+$).

Example 57

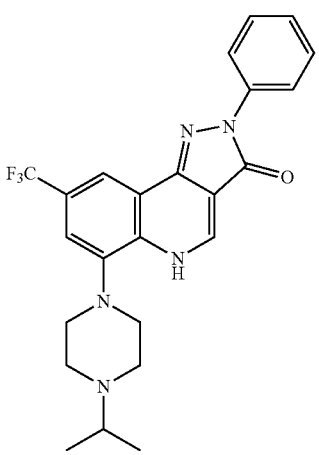

52d

2-Phenyl-6-(4-iso-propylpiperazin-1-yl)-8-trifluoromethyl-2,5-dihydro-pyrazolo[4,3-c]quinolin-3-one (52d): The title compound was obtained following procedure described in the synthesis of 19b using 51 and 1-iso-propylpiperazine. $^1$H-NMR (CD$_3$OD) δ (ppm): 2.05 (4H, brm), 2.50 (6H, brd), 2.94 (4H, brm), 3.24 (1H, m), 7.30 (1H, m), 7.48 (2H, m), 7.95 (2H, m), 8.04 (1H, s), 8.36 (1H, s), 8.75 (1H, s). m/z 456.3 (MH$^+$).

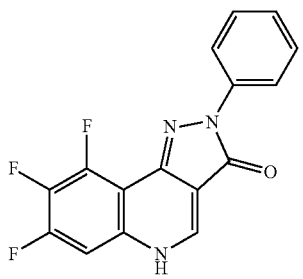

54

7,8,9-Trifluoro-2-phenyl-2,5-dihydro-pyrazolo-[4,3-c]quinolin-3-one (54): The title compound was prepared following the procedure described for 4a in four steps starting from 3,4,5-trifluoroaniline. $^1$H-NMR (DMSO-d6) δ (ppm): 7.15 (1H, t, J=7.82 Hz), 7.42 (2H, m), 7.51 (1H, m), 8.15 (2H, m), 8.77 (1H, s). m/z 316.3 (MH$^+$).

Example 58

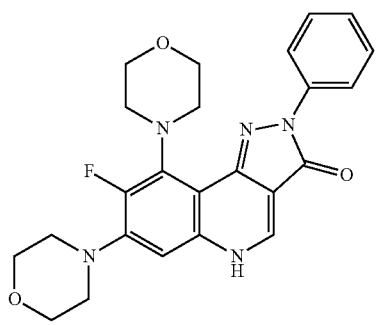

55

7,9-Bis(morpholin-4-yl)-8-fluoro-2-phenyl-2,5-dihydro-pyrazolo[4,3-c]quinolin-3-one (55): The title compound was obtained following procedure described in the synthesis of 19b using 53 and morpholine. $^1$H-NMR (DMSO) δ (ppm): 3.06 (4H, brm), 3.22 (4H, brm), 3.76 (4H, brm), 3.86 (4H, brm), 6.81 (1H, d, J=6.7 Hz), 7.15 (1H, m), 7.46 (2H, m), 8.18 (2H, m), 8.57 (1H, s). m/z 450.3 (MH$^+$).

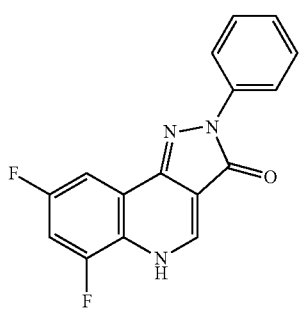

57

6,8-Difluoro-2-phenyl-2,5-dihydro-pyrazolo-[4,3-c]quinolin-3-one (57): The title compound was prepared following the procedure described for 4a in four steps starting from 2,4-difluoroaniline. $^1$H-NMR (DMSO-d6) δ (ppm): 7.17 (1H, dt, J=0.8, 7.7 Hz), 7.42 (2H, t, J=7.7 Hz), 7.74 (2H, m), 8.18 (2H, dd, J=7.8, 0.7 Hz), 8.52 (1H, s). m/z 298.2 (MH$^+$).

Example 59

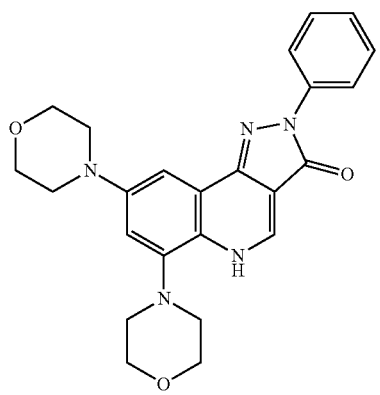

58a 6,8-Bis(morpholin-4-yl)-2-phenyl-2,5-dihydro-pyrazolo[4,3-c]quinolin-3-one (58a): The title compound was obtained following procedure described in the synthesis of 19b using 53 and morpholine. $^1$H-NMR (DMSO-d6) δ (ppm): 2.83 (4H, brm), 3.22 (4H, brm), 3.56 (4H, brm), 3.77 (4H, brm), 7.11 (1H, m), 7.26 (2H, dd, J=6.2, 1.9 Hz), 7.41 (2H, dd, J=7.8, 7.6 Hz), 8.20 (2H, d, J=8.6 Hz), 8.26 (1H, s). m/z 432.4 (MH$^+$).

Example 60

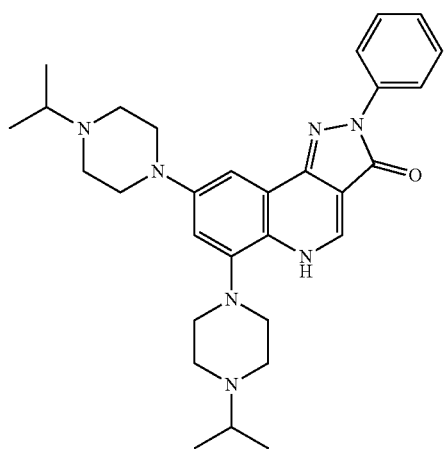

58b 6,8-Bis(4-iso-propylpiperazin-1-yl)-2-phenyl-2,5-dihydro-pyrazolo[4,3-c]quinolin-3-one (58b): The title compound was obtained following procedure described in the synthesis of 19b using 53 and 1-iso-propylpiperazine. $^1$H-NMR (DMSO-d6) δ (ppm): 0.99 (6H, d, J=6.8 Hz), 1.01 (6H, d, J=7.4 Hz), 2.72 (4H, brm), 2.83 (6H, br, m), 2.92 (4H, brm), 3.22 (4H, brm), 7.19 (3H, m), 7.41 (2H, m), 8.24 (3H, m). m/z 514.4 (MH$^+$).

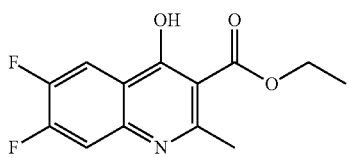

60

Ethyl 6,7-difluoro-4-hydroxy-2-methyl-quinoline-3-carboxylate (60): A solution of difluoro-isatoic anhydride in N,N-dimethylacetamide was added to a solution of sodium hydride (1.1 equiv.) and ethyl acetoacetate (1.1 equiv.) in N,N-dimethylacetamide with stiffing at room temperature. The mixture was heated at 120° C. for 10 minutes. The solvent was removed in vacuo and 6,7-4-hydroxy-2-methyl-quinoline-3-carboxylic acid ethyl ester (2g) was precipitated with water followed by filtration. $^1$H NMR (DMSO-d6) δ (ppm): 1.21 (3H, t, J=7.14 hz), 2.30 (3H, s), 4.10 (2H, q, J=7.14 Hz), 7.43 (1H, dd, J=10.71, 7.69 Hz), 7.82 (1H, dd, J=10.69, 8.24 Hz. m/z 268.7 (MH$^+$).

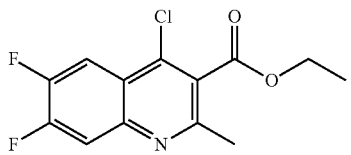

61

Ethyl 4-chloro-6,7-difluoro-2-methyl-quinoline-3-carboxylate (61): A suspension of 4-hydroxy quinoline 60 was refluxed with phosphorus oxychloride for 30 minutes. To the cooled reaction mixture was added aqueous ammonia and the product was obtained by extracting with methylene chloride, dried over sodium sulfate and concentrated in vacuo. $^1$H NMR (CDCl$_3$) δ (ppm): 1.44 (3H, t, J=7.14 Hz), 2.70 (3H, s), 4.50 (2H, q, J=7.14 Hz), 7.62 (1H, t, J=7.69 Hz), 7.78 (1H, dd, J=10.71, 7.69 Hz), 7.95 (2H, d, J=10.72, 8.24 Hz). m/z 286.7 (MH$^+$).

62

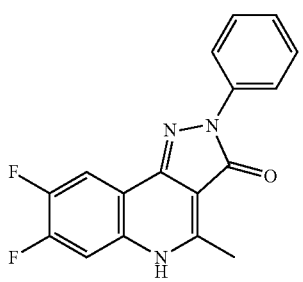

7,8-Difluoro-4-methyl-2-phenyl-2,5-dihydro-pyrazolo[4,3-c]quinolin-3-one (62): The title compound was synthesized following the procedure described in synthesis of 4a using 61 and phenyl hydrazine. $^1$H NMR (DMSO-d6) δ (ppm): 2.80 (3H, s), 6.87 (1H, m), 7.19 (1H, m), 7.34 (1H, m), 7.42 (1H, m), 7.61 (1H, m), 8.17 (1H, m). m/z 312.2 (MH$^+$).

Example 61

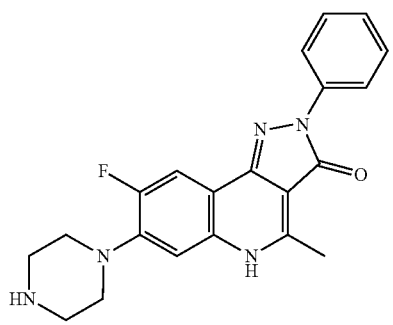

63a

8-Fluoro-4-methyl-2-phenyl-7-piperazin-1-yl-2,5-dihydro-pyrazolo[4,3-c]quinolin-3-one (63a): The title compound was obtained following procedure described in the synthesis of 19b using 62 and piperazine. $^1$H-NMR (DMSO-d6) δ (ppm): 2.76 (3H, s), 2.87 (4H, brm), 3.01 (4H, brm), 7.10 (2H, m), 7.40 (2H, dd, J=8.24, 7.69 Hz), 7.72 (1H, d, J=13.19 Hz), 8.19 (2H, dd, J=8.79, 1.10 Hz), m/z 378.4 (MH$^+$).

Example 62

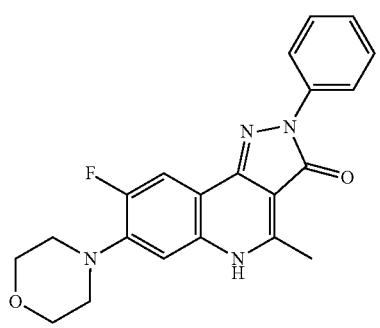

63b

8-Fluoro-4-methyl-7-morpholin-4-yl-2-phenyl-2,5-dihydro-pyrazolo [4,3-c]quinolin-3-one (63b): The title compound was obtained following procedure described in the synthesis of 19b using 62 and morpholine. $^1$H-NMR (DMSO-d6) δ (ppm): 2.74 (3H, s), 3.11 (4H, brm), 3.77 (4H, brm), 7.15 (2H, m), 7.41 (2H, dd, m), 7.76 (1H, d, J=12.91 Hz), 8.18 (2H, d, J=8.51 Hz), m/z 379.4 (MH$^+$).

BIOLOGICAL EXAMPLES

The ability of a compound disclosed herein to act as ligand to the benzodiazepine site of GABA$_A$ can be determined using pharmacological models which are well known in the art using the following assay. The IC$_{50}$ values for the exemplified compounds range from sub nM to 10 μM in a 3-concentration dose response curve.

Benzodiazepine Binding Assay

Whole brain (except cerebellum) of male Wistar derived rats weighing 175±25 g were used to prepare GABA$_A$ central benzodiazepine receptor in Na—K phosphate buffer pH 7.4. A 5 mg aliquot was incubated with 1 nM (3H)-flunitrazepam for 60 minutes at 25° C. Experiments were performed in the presence or absence of 30 μM of GABA. Non-specific binding was estimated in the presence of 10 μM of diazepam. Membranes were filtered and washed, the filters were then counted to determine ($^3$H)-flunitrazepam specifically bound. Test compounds were tested in duplicate according to the required concentrations (Damm, H. W., et al. (1978) *Res. Comm. Chem. Pathol. Pharmacol.* 22: 597-560 incorporated herein in its entirety; Speth, R. C., et al. (1979) *Life Sci.* 24: 351-357 incorporated herein in its entirety).

Examples of Activity:
wherein:
A indicates an $IC_{50}$ of >1 µM
B indicates an $IC_{50}$ of <1 µM
C indicates an $IC_{50}$ of <1 nM All compounds disclosed in Table 1 are assumed to be drawn as neutral. If not indicated, a hydrogen atom is assumed to be present on nitrogen atoms to provide a neutral compound. The compounds of Table 1 can exist in additional isomeric forms, for example, the compounds can exist as tautomers of the drawn structures. The compounds disclosed in Table 1 encompass all possible tautomers of the drawn structures. One of skill in the art will understand that a compound can exist in different tautomeric forms or mixtures there of depending on the environment encompassing the compound, that is an equilibrium can exist between the different tautomerics forms of the compounds and the equilibrium between said forms can be influenced by outside factors. Note that salts, including acid addition salts are also contemplated.

TABLE 1

| No. | Structure | BZ binding assay ($IC_{50}$) | EP Result |
|---|---|---|---|
| 7a | 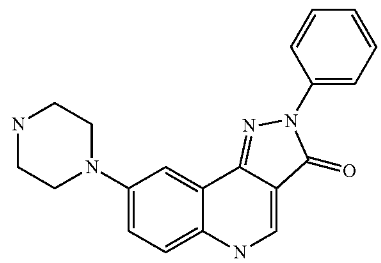 | B | Pos |
| 7b | 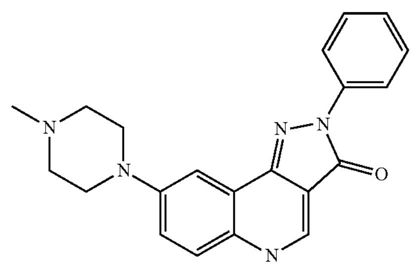 [SMILES: CN1CCN(c2ccc3[nH]cc4c(=O)n(-c5ccccc5)nc-4c3c2)CC1] | B | Pos |
| 7c | 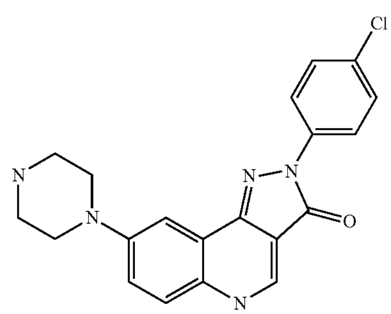 [SMILES: O=c1c2c[nH]c3ccc(N4CCNCC4)cc3c-2nn1-c1ccc(Cl)cc1] | B | Pos |
| 7d | 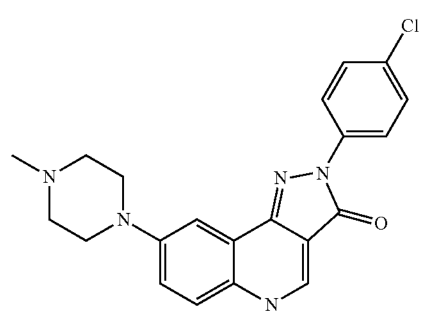 [SMILES: CN1CCN(c2ccc3[nH]cc4c(=O)n(-c5ccc(Cl)cc5)nc-4c3c2)CC1] | B | Pos |

TABLE 1-continued
| No. | Structure | BZ binding assay (IC$_{50}$) | EP Result |
|---|---|---|---|
| 7e | 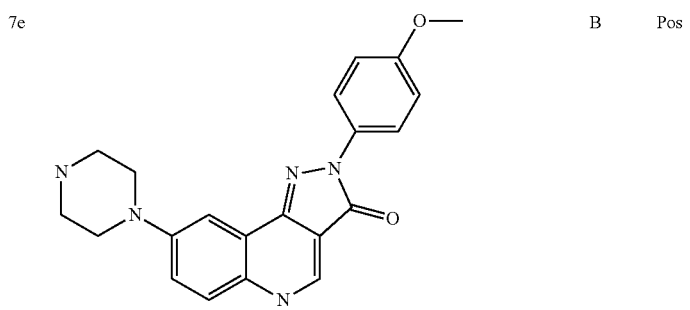 | B | Pos |
| 7f | 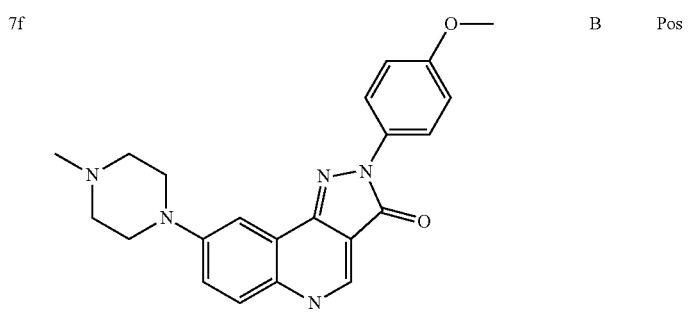 | B | Pos |
| 14a | 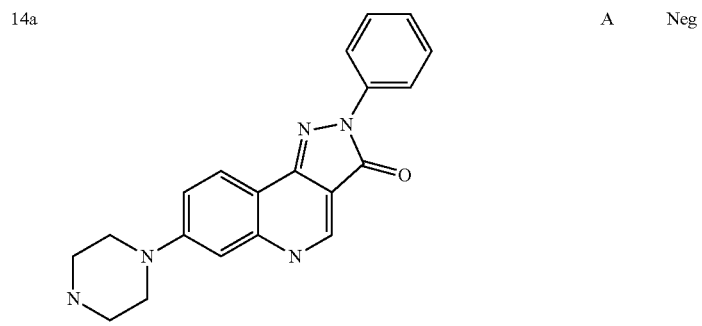 | A | Neg |
| 14b | 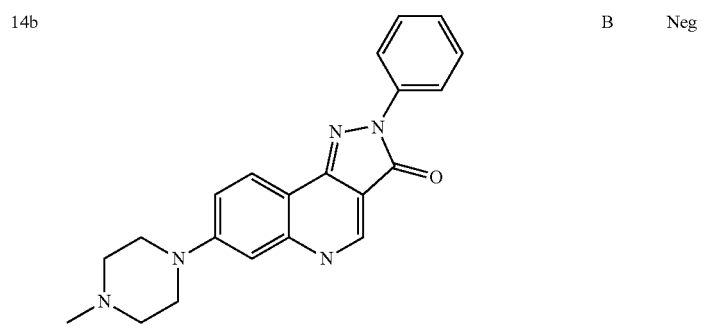 | B | Neg |

TABLE 1-continued

| No. | Structure | BZ binding assay (IC$_{50}$) | EP Result |
|---|---|---|---|
| 14c | 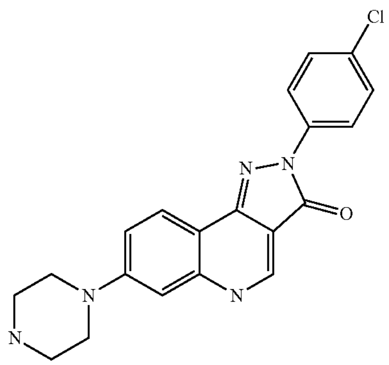 [SMILES: O=c1c2c[nH]c3cc(N4CCNCC4)ccc3c-2nn1-c1ccc(Cl)cc1] | B | Neg |
| 14d | 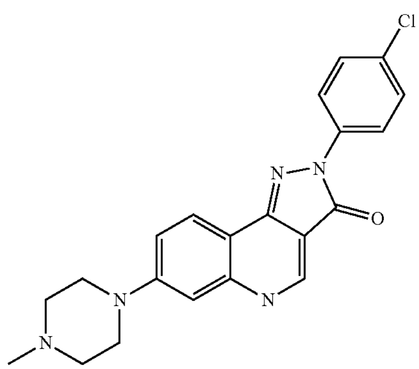 [SMILES: CN1CCN(c2ccc3c4nn(-c5ccc(Cl)cc5)c(=O)c-4c[nH]c3c2)CC1] | B | Neg |
| 14e | 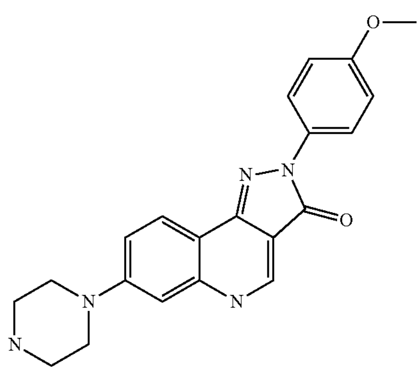 [SMILES: COc1ccc(-n2nc3c4ccc(N5CCNCC5)cc4[nH]cc-3c2=O)cc1] | B | Neg |
| 14f | 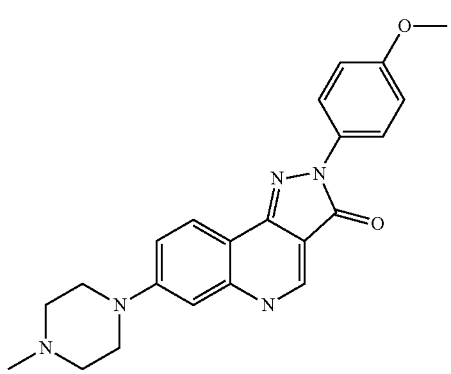 | A | Neg |

TABLE 1-continued

| No. | Structure | BZ binding assay (IC$_{50}$) | EP Result |
|---|---|---|---|
| 19a | 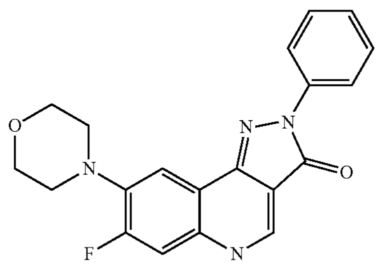 [SMILES: O=c1c2c[nH]c3cc(F)c(N4CCOCC4)cc3c-2nn1-c1ccccc1] | C | Pos |
| 19b | 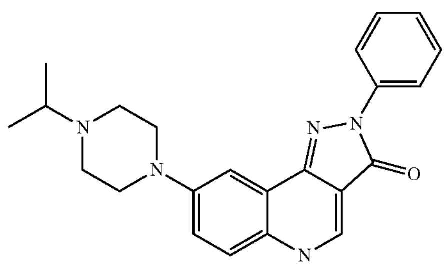 [SMILES: CC(C)N1CCN(c2ccc3[nH]cc4c(=O)n(-c5ccccc5)nc-4c3c2)CC1] | B | Pos |
| 19c | 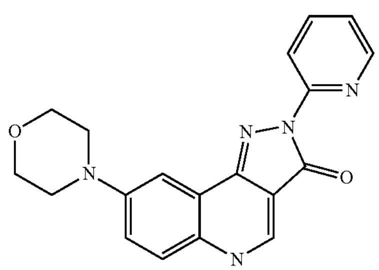 [SMILES: O=c1c2c[nH]c3ccc(N4CCOCC4)cc3c-2nn1-c1ccccn1] | B | Neg |
| 19d | 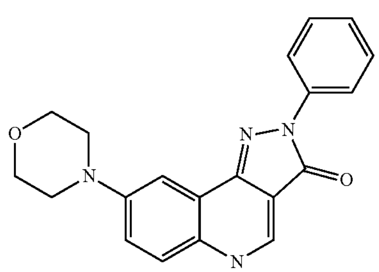 [SMILES: O=c1c2c[nH]c3ccc(N4CCOCC4)cc3c-2nn1-c1ccccc1] | B | Neg |
| 19e | 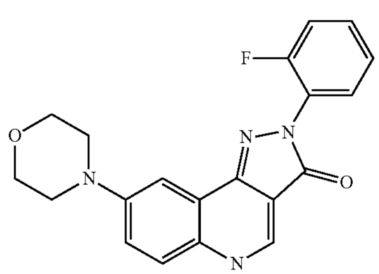 [SMILES: O=c1c2c[nH]c3ccc(N4CCOCC4)cc3c-2nn1-c1ccccc1F] | B | Neg |

TABLE 1-continued

| No. | Structure | BZ binding assay (IC$_{50}$) | EP Result |
|---|---|---|---|
| 19f | 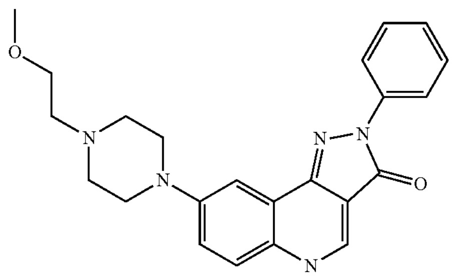 [SMILES: COCCN1CCN(c2ccc3[nH]cc4c(=O)n(-c5ccccc5)nc-4c3c2)CC1] | B | Pos |
| 19g | 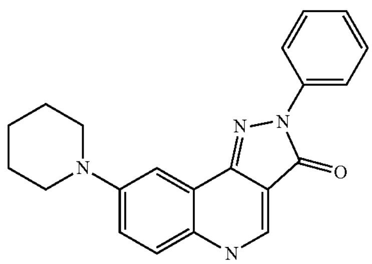 [SMILES: O=c1c2c[nH]c3ccc(N4CCCCC4)cc3c-2nn1-c1ccccc1] | B | Pos |
| 19h | 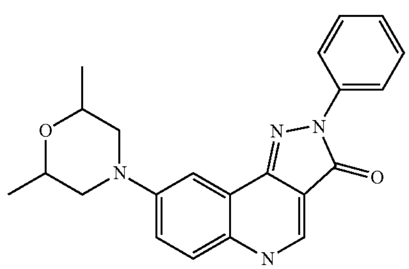 [SMILES: CC1CN(c2ccc3[nH]cc4c(=O)n(-c5ccccc5)nc-4c3c2)CC(C)O1] | B | |
| 19i | 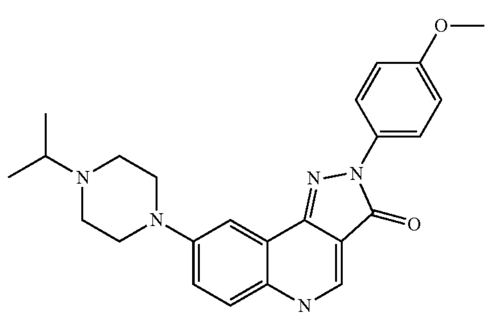 [SMILES: COc1ccc(-n2nc3c4cc(N5CCN(C(C)C)CC5)ccc4[nH]cc-3c2=O)cc1] | B | Pos |
| 19j | 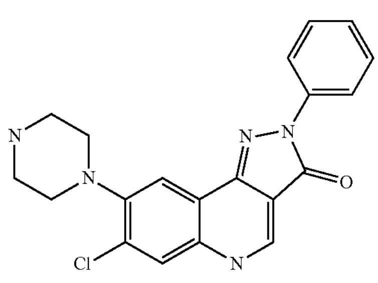 [SMILES: O=c1c2c[nH]c3cc(Cl)c(N4CCNCC4)cc3c-2nn1-c1ccccc1] | B | Neg |

TABLE 1-continued

| No. | Structure | BZ binding assay (IC$_{50}$) | EP Result |
|---|---|---|---|
| 19k | 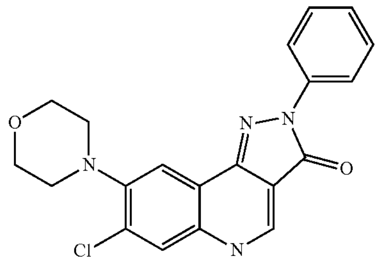 | B | Pos |
| 28a | 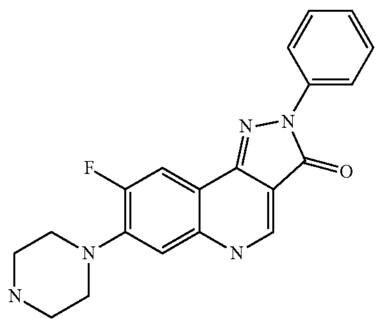 [SMILES: O=c1c2c[nH]c3cc(N4CCOCC4)c(F)cc3c-2nn1-c1ccccc1] | B | |
| 28b | 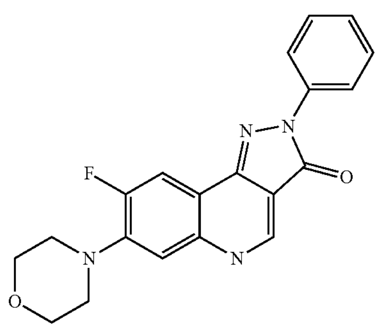 | B | Pos |
| 28c | 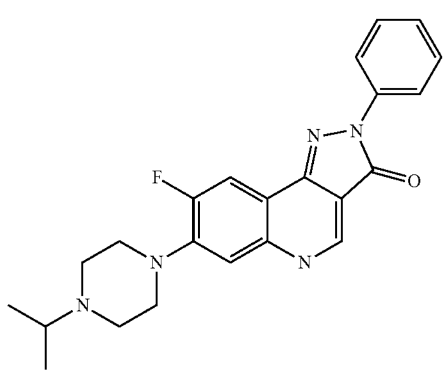 | B | Pos |

TABLE 1-continued

| No. | Structure | BZ binding assay (IC$_{50}$) | EP Result |
|---|---|---|---|
| 28d | 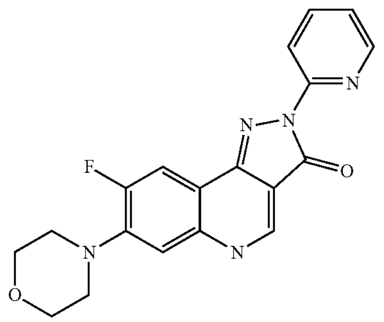 [SMILES: O=c1c2c[nH]c3cc(N4CCOCC4)c(F)cc3c-2nn1-c1ccccn1] | B | Neg |
| 28e | 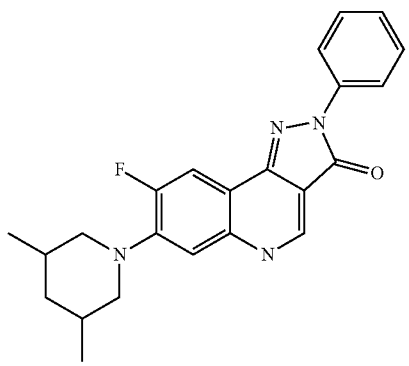 | B | Pos |
| 28f | 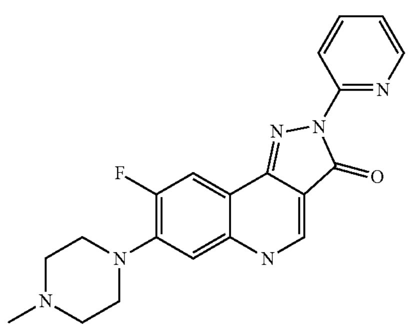 [SMILES: CN1CCN(c2cc3[nH]cc4c(=O)n(-c5ccccn5)nc-4c3cc2F)CC1] | B | Pos |
| 28g | 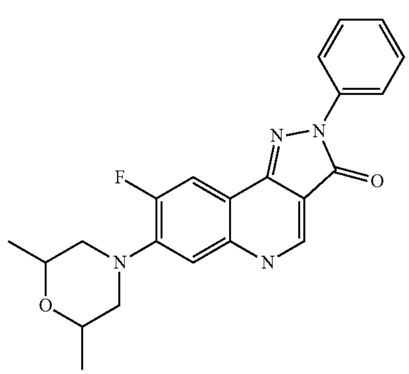 [SMILES: CC1CN(c2cc3[nH]cc4c(=O)n(-c5ccccc5)nc-4c3cc2F)CC(C)O1] | B | Pos |

TABLE 1-continued

| No. | Structure | BZ binding assay (IC$_{50}$) | EP Result |
|---|---|---|---|
| 28h | 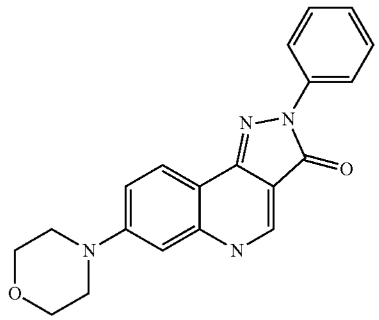 [SMILES: O=c1c2c[nH]c3cc(N4CCOCC4)ccc3c-2nn1-c1ccccc1] | B | Pos |
| 28i | 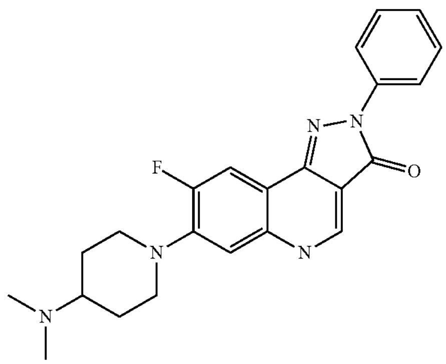 [SMILES: CN(C)C1CCN(c2cc3[nH]cc4c(=O)n(-c5ccccc5)nc-4c3cc2F)CC1] | B | |
| 28j | 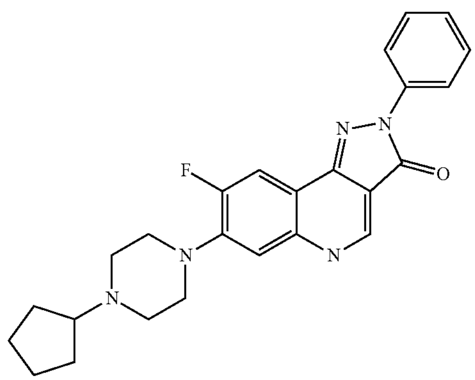 [SMILES: O=c1c2c[nH]c3cc(N4CCN(C5CCCC5)CC4)c(F)cc3c-2nn1-c1ccccc1] | B | |
| 28k | 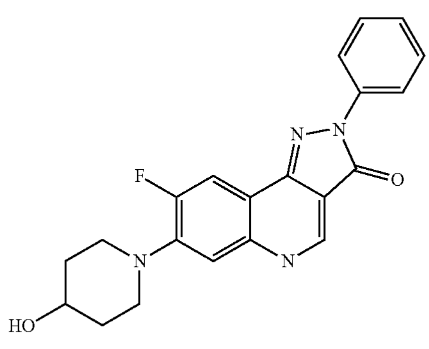 [SMILES: O=c1c2c[nH]c3cc(N4CCC(O)CC4)c(F)cc3c-2nn1-c1ccccc1] | B | |

TABLE 1-continued

| No. | Structure | BZ binding assay (IC$_{50}$) | EP Result |
|---|---|---|---|
| 28l | 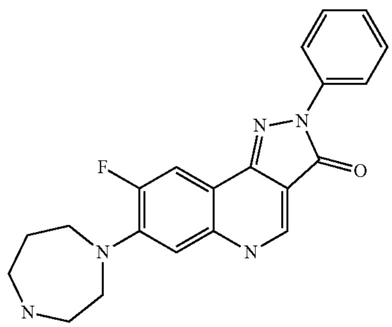 [SMILES: O=c1c2c[nH]c3cc(N4CCCNCC4)c(F)cc3c-2nn1-c1ccccc1] | | B |
| 28m | 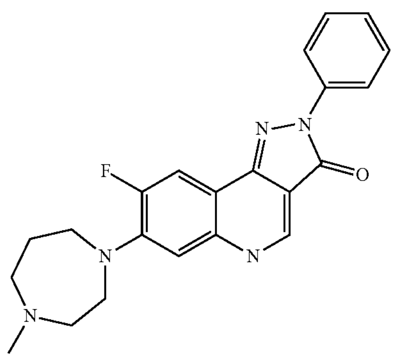 [SMILES: CN1CCCN(c2cc3[nH]cc4c(=O)n(-c5ccccc5)nc-4c3cc2F)CC1] | | B |
| 28n | 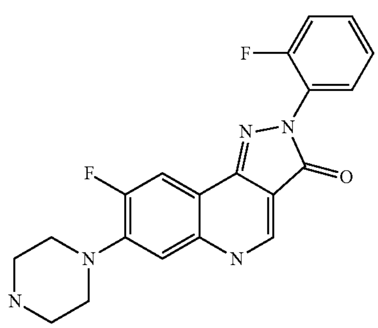 [SMILES: O=c1c2c[nH]c3cc(N4CCNCC4)c(F)cc3c-2nn1-c1ccccc1F] | | A |
| 28o | 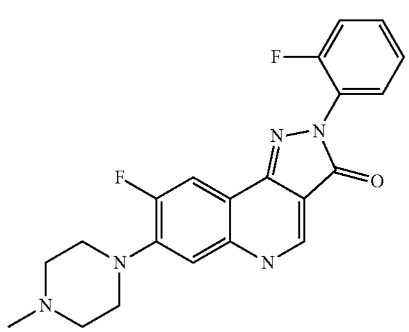 [SMILES: CN1CCN(c2cc3[nH]cc4c(=O)n(-c5ccccc5F)nc-4c3cc2F)CC1] | | B |

TABLE 1-continued

| No. | Structure | BZ binding assay (IC$_{50}$) | EP Result |
|---|---|---|---|
| 28p | 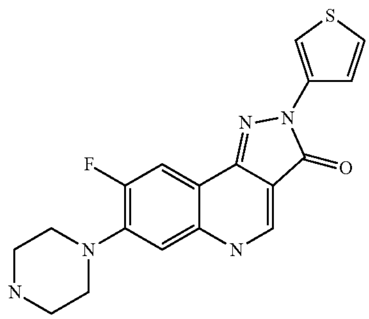 | B | Neg |
| 28q | 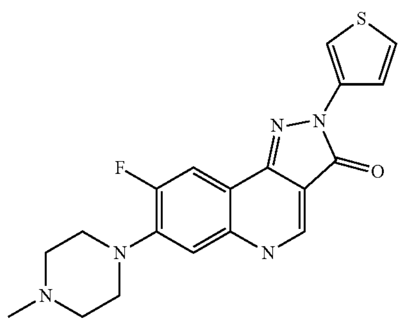 [SMILES: CN1CCN(c2cc3[nH]cc4c(=O)n(-c5ccsc5)nc-4c3cc2F)CC1] | A | |
| 28r | 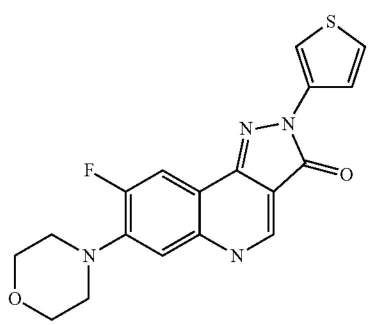 [SMILES: O=c1c2c[nH]c3cc(N4CCOCC4)c(F)cc3c-2nn1-c1ccsc1] | B | |
| 39 | 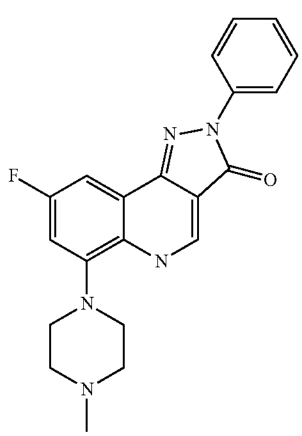 [SMILES: CN1CCN(c2cc(F)cc3c4nn(-c5ccccc5)c(=O)c-4c[nH]c23)CC1] | | |

TABLE 1-continued

| No. | Structure | BZ binding assay (IC$_{50}$) | EP Result |
|---|---|---|---|
| 44a | 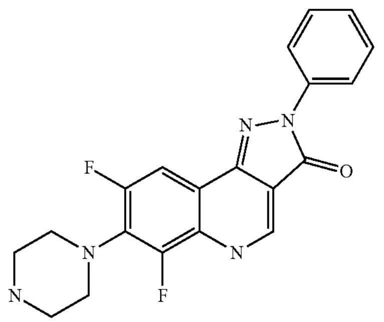 | B | Neg |
| 44b | 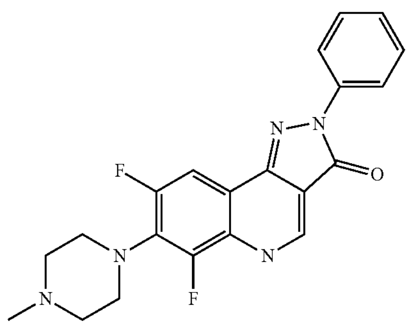 [SMILES: CN1CCN(c2c(F)cc3c4nn(-c5ccccc5)c(=O)c-4c[nH]c3c2F)CC1] | B | Pos |
| 44c | 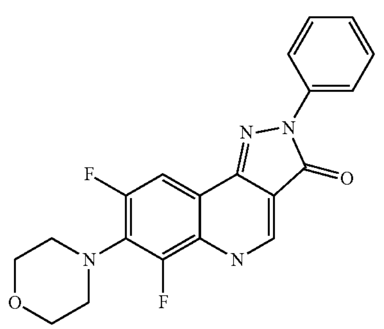 [SMILES: O=c1c2c[nH]c3c(F)c(N4CCOCC4)c(F)cc3c-2nn1-c1ccccc1] | B | Pos |
| 44d | 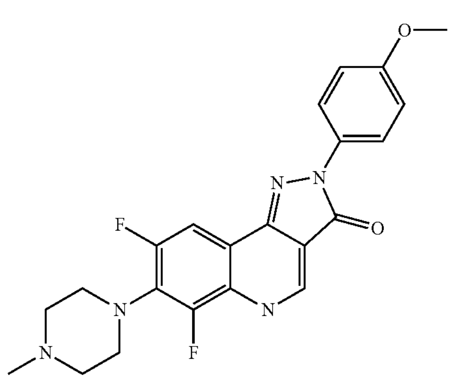 | B | Pos |

TABLE 1-continued

| No. | Structure | BZ binding assay (IC$_{50}$) | EP Result |
|---|---|---|---|
| 48a | 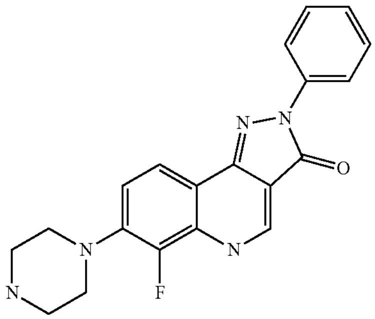 | | A |
| 48b | 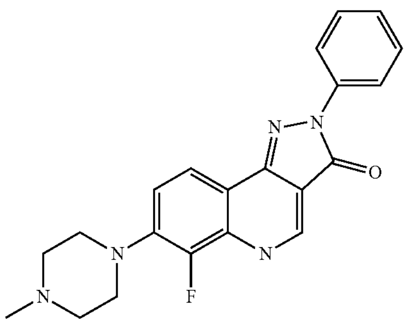 [SMILES: CN1CCN(c2ccc3c4nn(-c5ccccc5)c(=O)c-4c[nH]c3c2F)CC1] | | A |
| 48c | 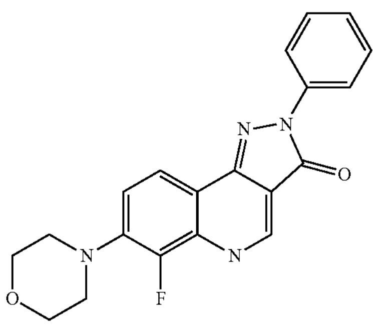 [SMILES: O=c1c2c[nH]c3c(F)c(N4CCOCC4)ccc3c-2nn1-c1ccccc1] | | B |
| 48d | 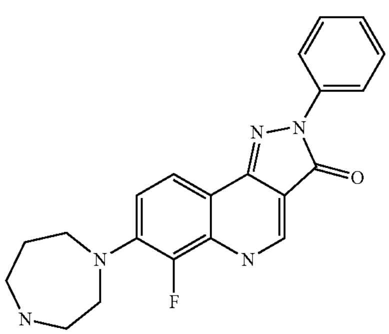 [SMILES: O=c1c2c[nH]c3c(F)c(N4CCCNCC4)ccc3c-2nn1-c1ccccc1] | | B |

TABLE 1-continued

| No. | Structure | BZ binding assay (IC$_{50}$) | EP Result |
|---|---|---|---|
| 48e | 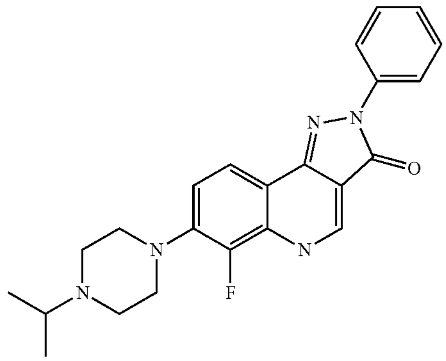 [SMILES: CC(C)N1CCN(c2ccc3c4nn(-c5ccccc5)c(=O)c-4c[nH]c3c2F)CC1] | | B |
| 48f | 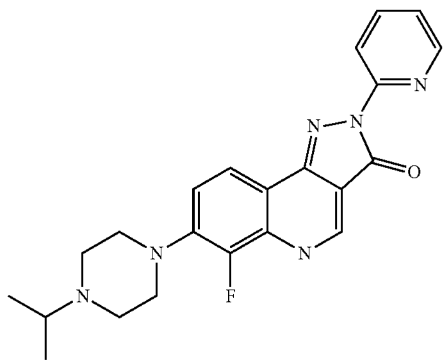 [SMILES: CC(C)N1CCN(c2ccc3c4nn(-c5ccccn5)c(=O)c-4c[nH]c3c2F)CC1] | | B |
| 52a | 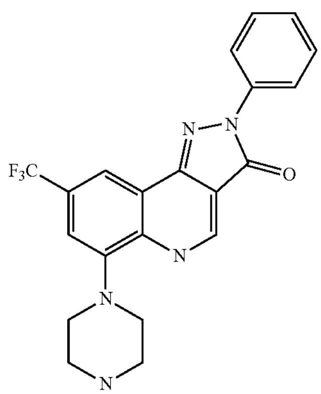 [SMILES: O=c1c2c[nH]c3c(N4CCNCC4)cc(C(F)(F)F)cc3c-2nn1-c1ccccc1] | | B |
| 52b | 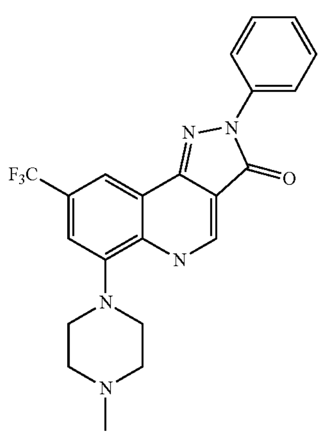 [SMILES: CN1CCN(c2cc(C(F)(F)F)cc3c4nn(-c5ccccc5)c(=O)c-4c[nH]c23)CC1] | | B |

TABLE 1-continued
| No. | Structure | BZ binding assay (IC$_{50}$) | EP Result |
|---|---|---|---|
| 52c | 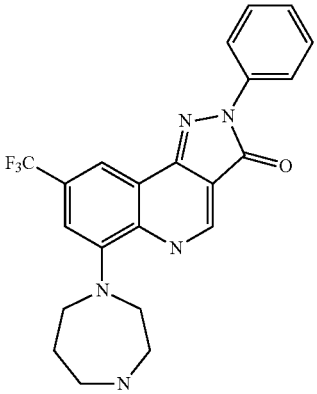 [SMILES: O=c1c2c[nH]c3c(N4CCCNCC4)cc(C(F)(F)F)cc3c-2nn1-c1ccccc1] | | B |
| 52d | 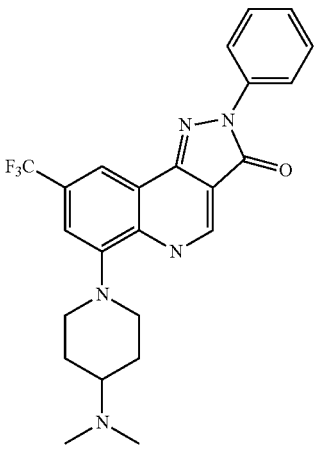 [SMILES: CN(C)C1CCN(c2cc(C(F)(F)F)cc3c4nn(-c5ccccc5)c(=O)c-4c[nH]c23)CC1] | | B |
| 55 | 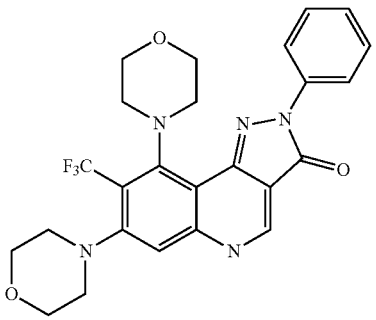 [SMILES: O=c1c2c[nH]c3cc(N4CCOCC4)c(C(F)(F)F)c(N4CCOCC4)c3c-2nn1-c1ccccc1] | | B |
| 58a | 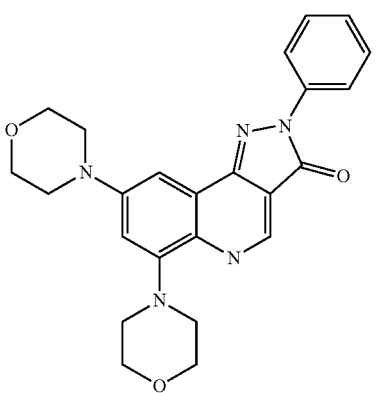 [SMILES: O=c1c2c[nH]c3c(N4CCOCC4)cc(N4CCOCC4)cc3c-2nn1-c1ccccc1] | | Neg |

TABLE 1-continued

| No. | Structure | BZ binding assay (IC$_{50}$) | EP Result |
|---|---|---|---|
| 58b | 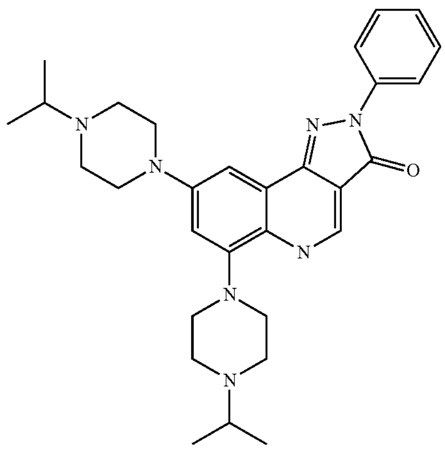 [SMILES: CC(C)N1CCN(c2cc(N3CCN(C(C)C)CC3)c3[nH]cc4c(=O)n(-c5ccccc5)nc-4c3c2)CC1] | | Neg |
| 63a | 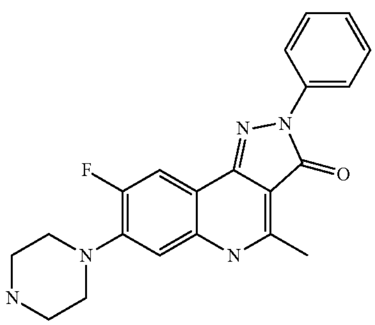 | | A |
| 63b | 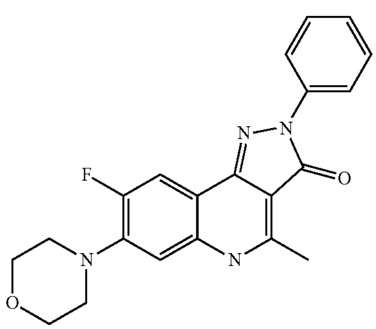 [SMILES: Cc1[nH]c2cc(N3CCOCC3)c(F)cc2c2nn(-c3ccccc3)c(=O)c1-2] | | A |

The modulation of GABA$_A$ function is determined by changes in current as determined in an electrophysiology assay, as is detailed below.

Electrophysiology Assay

Preparation of RNA mRNA was prepared from lyophilized plasmid pellets containing cDNA inserts encoding the specific GABA$_A$ receptor subunit. cDNAs encoding the α2, α3, and γ3 subunits were subcloned into pBluescript, SK−. cDNAs encoding the a 1 and a 5 subunits were subcloned into prC while cDNA encoding the β2 subunit was subcloned into pcDNA1. The cDNA construct encoding the g 2s subunit is in the pGH19 expression construct. Overnight cultures of transformed DH5a bacterial cells were performed to grow sufficient quantities for maxiprep isolation of the plasmid cDNA. The resulting plasmid cDNA was linearized by digestion with an appropriate restriction enzyme that cleaves distal to the cDNA insert [XbaI (α1, β2), NotI (α3, γ2 s), SacII (α2), or ApaI (α5)]. Following digestion, plasmid cDNA was treated with proteinase K and extracted with phenol/chloroform/isoamyl alcohol, followed by ethanol precipitation. cDNA quality was assessed by agarose-gel electrophoresis (1.5% agarose gel). Samples were stored at −20° C. until use. In vitro transcription was performed with T7 RNA polymerase. mRNA was then stored at −80° C. until use. Plasmids were linearized with appropriate restriction enzymes before in vitro transcription using the Message Machine kit (Ambion, Austin, Tex.).

GABA$_A$ Receptor Expression in Xenopus Oocytes

GABA$_A$ receptor expression in Xenopus oocytes: Following 45 min of 0.15% Tricaine anesthesia, an ovarian section containing the follicular oocytes was removed from the frog through a lateral abdominal incision. Oocytes were immediately placed in a calcium-free solution (NaCl 96 mM, MgCl$_2$ 1 mM, KCl 2 mM, Hepes 50 mM, pyruvate 2.5 mM, gentamycin 100 μg/mL, penicillin-streptomycin 50 U/mL, pH 7.4). Following 1.5-2 hour incubation in 0.2% collagenase (type II, Sigma Chemical Co., St. Louis, Mo.) at room temperature, individual Dumont stage V and VI oocytes were transferred to an incubator and maintained overnight in Barth's solution (NaCl 84 mM, NaHCO$_3$ 2.4 mM, MgSO$_4$ 0.82 mM, KCl 1 mM, Ca(NO$_3$)$_2$ 0.33 mM, CaCl$_2$ 0.41 mM, Tris/HCl 7.5 mM, pyruvate 2.5 mM, gentamycin 50 μg/mL, penicillin-streptomycin, 100 units/mL, pH 7.4) at 18-20° C. and used for experiments 1-5 days post-injection. Oocytes were injected solution using an electronic microinjector (Drummond, Broomall, Pa.) with 50 nL of RNA containing 0.3-0.5 ng of each subunit RNA in a 1:1:2 ratio. The injected oocytes were used for experiments after 1-5 days of incubation in Barth's solution at 18-20° C.

Electrophysiology

Measurements of ion currents from oocytes expressing GABA$_A$ receptors were performed using a Warner two-electrode voltage-clamp amplifier (Warner Instruments, Inc., Foster City, Calif.) (Park-Chung, M. A., et al. (1999) *Brain Res.* 830: 72-87 incorporated herein in its entirety). Microelectrodes were fabricated from borosilicate glass capillaries with a programmed pipette puller (Sutter Instrument Co., CA). Microelectrode resistance was 1-3 MΩ when filled with 3 M KCl. The oocyte recording chamber was continuously perfused with ND-96 solution. Oocytes were clamped at a holding potential of −70 mV during data acquisition. The membrane current was filtered at 10 Hz and sampled at 100 Hz. Compounds were applied by a gravity-driven external perfusion system. The working volume of the recording chamber was 30 mL and the rate of the perfusion was approximately 50 mL/sec. Compound application was 20-25 sec followed by a minimum of 150 sec wash. Data acquisition and external perfusion was computer controlled by custom-developed software. All experiments were performed at room temperature (22-24° C.). Dose-response data from each oocyte were fitted to the Hill equation by non-linear regression using the equation:

$$I_{GABA} = E_{max}/(1+(EC_{50}/c)nH)$$

Emax is the maximum response, EC$_{50}$ is the concentration producing 50% of the maximal response, n$_H$ is the Hill coefficient and c is the concentration of agonist. Based on the GABA concentration-response curve fit, an EC$_{20}$ for GABA was determined for each subunit combination, and this concentration was used for subsequent modulator concentration-response studies. Peak current measurements were normalized and expressed as a fraction of the peak control current measurements. Control current responses to an EC$_{20}$ concentration of GABA were re-determined after every 2-4 modulator applications. Percent modulation was determined by the equation:

$$\% \text{ change} = (I'/I-1) \times 100$$

where I is the control response at the GABA EC$_{20}$ and I' the response in the presence of modulator (Lippa A, et al. (2005) *Proc. Natl. Acad. Sci. USA* 102(20): 7380-7385 incorporated herein in its entirety).

Some compounds showed positive modulation and some showed negative modulation at a screening concentration of 10 μM.

Object Recognition Assay

Effect on animal behavior, specifically improvement of cognitive function (including but not limited to both short-term/working memory and long-term memory), can be determined using a number of established protocols. One method, novel object recognition, is described below.

Object Recognition Assay

Object recognition is an ethologically relevant task for rodents, which does not result from negative reinforcement (foot shock). This task relies on the natural curiosity of rodents to explore novel objects in their environments more than familiar ones. Obviously, for an object to be "familiar," the animal must have attended to it before and remembered that experience. Hence, animals with better memory will attend and explore a new object more than an object familiar to them. During testing, the animal is presented with the training object and a second, novel one. Memory of the training object renders it familiar to the animal, and it then spends more time exploring the new novel object rather than the familiar one (Bourtchouladze, R., et al. (2003) *Proc. Natl. Acad. Sci. USA* 100: 10518-10522 incorporated herein in its entirety). Recent neuroimaging studies in humans demonstrated that memory in object recognition depends on prefrontal cortex (PFC) (Deibert, E., et al. (1999) *Neurology* 52: 1413-1417 incorporated herein in its entirety). Consistent with these findings, rats with the PFC lesions show poor working memory when they are required to discriminate between familiar and novel objects (Mitchell, J. B. and Laiacona, J. (1998) *Behav. Brain Res.* 97: 107-113 incorporated herein in its entirety). Other studies on monkeys and rodents suggest that the hippocampus is important for novel object recognition (Teng, E. et al. (2000) *J. Neuroscience* 20: 3853-3863 incorporated herein in its entirety; Mumby, D. G. (2001) *Behavioural Brain Research* 127: 159-181 incorporated herein in its entirety). Hence, object recognition provides an excellent behavioral model to evaluate drug-compound effects on cognitive task associated with function of hippocampus and cortex.

The strength of memory retention in most cases is dependent on the amount of training (repetition of explicit or implicit trials). This "memory acquisition curve" can be influenced by many experimental and physical variables, which include, but are not limited to, temperature, humidity, ambient noise, lighting levels, the size of the training arena, the size and dimensions of the objects, the physical textures and colors of the training arena and the animal's stress levels, motivational states or experiences prior to training. To evaluate memory enhancing compounds for NOR, the experimenter must parameterize training duration to define (i) the duration (amount of training) required to reach an asymptotic (high) level of memory retention and (ii) a lesser duration at which memory retention is sub-maximal. Memory enhancing compounds will produce higher memory retention with sub-maximal training (but may have no measurable effect with asymptotic ("maximal") training). Typically, the difference between sub-maximal and asymptotic memory must be sufficiently larger to yield appropriate statistical power. An example which follows:

Prior to initiation of training, animals were handled and habituated to the training arena. Appropriately sized arenas were used for different species (e.g. for mice: a Plexiglas box of L=48 cm; W=38 cm and H=20 cm; for rats: a Plexiglas box of L=70 cm; W=60 cm and H=35 cm). The day before training, an individual animal was placed into a training apparatus located in a dimly lit room and allowed to habituate to the environment for 15 minutes (also see (Pittenger, C., et al. (2002) *Neuron* 34: 447-462 incorporated herein in its entirety; Bourtchouladze, R., et al. (2003) *Proc. Natl. Acad. Sci. USA* 100: 10518-10522 incorporated herein in its entirety). Training was initiated 24 h hours after habituation. An animal was placed back into the training box, which contained two identical objects (e.g. a small conus-shape object), and was allowed to explore these objects. The objects were placed into the central area of the box and the spatial position of objects (left-right sides) was counterbalanced between subjects. Animals were trained for 15 minutes. To test for memory retention, animals were observed for 10 minutes 24 hours after training. A rodent was presented with two objects, one of which was used during training, and thus was 'familiar' and the other of which was novel (e.g. a small pyramid-shape object). To ensure that the discrimination targets do not differ in smell, after each experimental subject, the apparatus and the objects were thoroughly cleaned with 90% ethanol, dried and ventilated for a few minutes.

The experiments were videotaped via an overhead video camera system. Types were then reviewed by a blinded observer and the following behavioral parameters were determined: time of exploration of an each object; the total time of exploration of the objects; number of approaches to the objects; and time (latency) to first approach to an object. The discrimination index—memory score—was determined as described previously (Ennaceur, A. and Aggleton, J. P. (1997) *Behav. Brain Res.* 88: 181-193 incorporated herein in its entirety; Bourtchouladze, R., et. al. (2003) *Proc. Natl. Acad. Sci. USA* 100: 10518-10522 incorporated herein in its entirety). This Data was analyzed by Student's unpaired t test using a software package (Statview 5.0.1; SAS Institute, Inc). All values in the text and figures are expressed as mean±SEM.

For NOR, 1-hr memory retention represents a measure of decremental, short-term memory (usually transcription independent), which contributes to cognitive functions, such as working memory (radial arm maze, delayed match to sample, etc), executive function (task-switching, etc.) and attentional processes (priming, etc). Twenty-four hour memory retention represents a measure of long-term memory, to which STM is converted through the molecular and cellular processes of memory consolidation. LTM contributes to lasting cognitive functions such as reference memory.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. A method of treating an animal in need of enhancement of memory or cognition comprising administering to the animal an effective amount of a compound of formula (I):

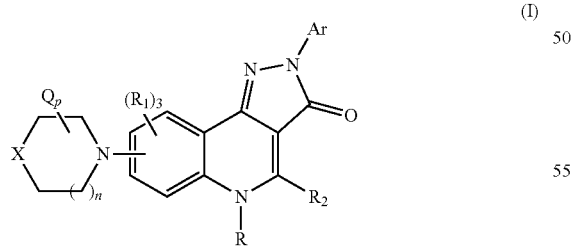

(I)

or a tautomer thereof, or their pharmaceutically acceptable salts,
wherein
R is hydrogen, or oxide;
each $R_1$ is selected from the group consisting of hydrogen, hydroxy, halo, cyano, —$CONR_aR_b$, —$NR_aR_b$, hydroxy($C_1$-$C_6$)alkyl, aryl, heteroaryl, heterocycle, amino($C_1$-$C_6$)alkyl, ($C_1$-$C_6$)alkyl optionally substituted with up to 5 fluoro, and ($C_1$-$C_6$)alkoxy optionally substituted with up to 5 fluoro;
$R_2$ is selected from the group consisting of hydrogen, hydroxy, halo, hydroxy($C_1$-$C_6$)alkyl, ($C_1$-$C_6$)alkyl optionally substituted with up to 5 fluoro, and ($C_1$-$C_6$) alkoxy optionally substituted with up to 5 fluoro;
each $R_a$ and $R_b$ is independently hydrogen, ($C_1$-$C_6$) alkyl, aryl, heteroaryl, heterocycle, ($C_1$-$C_6$)alkylaryl, —$S(O)_z(C_1$-$C_6)$alkyl, —$S(O)_z$aryl, —$C(O)(C_1$-$C_6)$alkyl, —$C(O)NR_g(C_1$-$C_6)$alkyl, —$C(O)NR_g$aryl, —$C(O)O(C_1$-$C_6)$alkyl, arylOC(O)— or arylC(O)—, or $R_a$ together with $R_b$ form a heterocycle group optionally substituted with one or more $R_d$; wherein the heterocycle group optionally include one or more groups selected from O (oxygen), S (sulfur), and $NR_c$;
each $R_c$ is independently hydrogen, ($C_2$-$C_6$)alkenyl, ($C_2$-$C_6$)alkynyl, —$C(O)O(C_1$-$C_6)$alkyl, —$C(O)$Oaryl, ($C_1$-$C_6$)alkoxy($C_1$-$C_6$)alkyl, hydroxy($C_1$-$C_6$) alkyl, aryl, heteroaryl, heterocycle, arylO($C_1$-$C_6$) alkyl, —$C(O)NR_g(C_1$-$C_6)$alkyl, —$C(O)NR_g$aryl, —$S(O)_z(C_1$-$C_6)$alkyl, —$S(O)_z$aryl, —$C(O)(C_1$-$C_6)$ alkyl, arylC(O)—, ($C_1$-$C_6$)alkyl optionally substituted with up to 5 fluoro, or ($C_1$-$C_6$)alkoxy optionally substituted with up to 5 fluoro;
each $R_d$ is independently selected from the group consisting of hydrogen, halo, oxo, hydroxy, —C(O) $NR_eR_f$, —$NR_eR_f$, hydroxy($C_1$-$C_6$)alkyl, aryl, aryl ($C_1$-$C_6$)alkyl, ($C_1$-$C_6$)alkyl optionally substituted with up to 5 fluoro, and ($C_1$-$C_6$)alkoxy optionally substituted with up to 5 fluoro;
each $R_e$ and $R_f$ is independently selected from hydrogen, ($C_1$-$C_6$)alkyl, aryl, heteroaryl, heterocycle, ($C_1$-$C_6$) alkylaryl, aryl($C_1$-$C_6$)alkyl, —$C(O)(C_1$-$C_6)$alkyl, —$S(O)_z(C_1$-$C_6)$alkyl, —$S(O)_zNR_g(C_1$-$C_6)$alkyl, —$S(O)_z$aryl, —$C(O)NR_g(C_1$-$C_6)$alkyl, —$C(O)(C_1$-$C_6)$alkyl, arylC(O)—, arylOC(O)—, or —$C(O)O(C_1$-$C_6)$alkyl;
$R_g$ is hydrogen, aryl, heteroaryl, heterocycle or ($C_1$-$C_6$) alkyl optionally substituted with up to 5 fluoro;
Ar is aryl optionally substituted with one or more M or heteroaryl optionally substituted with one or more M;
each Q is independently hydrogen, halo, oxo, hydroxy, —$C(O)NR_aR_b$, —$NR_aR_b$, ($C_1$-$C_6$)alkyl optionally substituted with up to 5 fluoro, ($C_1$-$C_6$)alkoxy optionally substituted with up to 5 fluoro, ($C_1$-$C_6$)alkyl optionally substituted with one or more $R_d$, hydroxy ($C_1$-$C_6$)alkyl optionally substituted with one or more $R_d$, aryl optionally substituted with one or more $R_d$, or aryl($C_1$-$C_6$)alkyl optionally substituted with one or more $R_d$;
each M is independently hydrogen, halo, $CF_3$, $CF_2H$, hydroxy, cyano, nitro, ($C_1$-$C_6$)alkyl, hydroxy($C_1$-$C_6$) alkyl, ($C_1$-$C_6$)alkoxy, —$NR_aR_b$, aryl, heteroaryl or heterocycle;
each X is independently NL, oxygen, $C(Q)_2$, or $S(O)_z$;
each L is independently hydrogen, ($C_2$-$C_6$)alkenyl, ($C_2$-$C_6$)alkynyl, —$C(O)O(C_1$-$C_6)$alkyl, —$C(O)$Oaryl, ($C_1$-$C_6$)alkoxy($C_1$-$C_6$)alkyl, hydroxy($C_1$-$C_6$)alkyl, aryl, heteroaryl, heterocycle, arylO($C_1$-$C_6$)alkyl, —$CONR_eR_f$, —$S(O)_z(C_1$-$C_6)$alkyl, —$S(O)_z$aryl, —$C(O)(C_1$-$C_6)$alkyl, arylC(O)—, —$C(O)NR_g(C_1$-$C_6)$alkyl, ($C_1$-$C_6$)alkyl optionally substituted with up to 5 fluoro, or($C_1$-$C_6$)alkoxy optionally substituted with up to 5 fluoro;
p is an integer selected from 0, 1, 2 and 3,
z is an integer selected from 0, 1, and 2; and
n is an integer selected from 0, 1, and 2.

2. The method of claim 1, wherein:

each $R_1$ is selected from the group consisting of hydrogen, hydroxy, halo, cyano, —$CONR_aR_b$, —$NR_aR_b$, hydroxy($C_1$-$C_6$)alkyl, amino($C_1$-$C_6$)alkyl, ($C_1$-$C_6$)alkyl optionally substituted with up to 5 fluoro, and ($C_1$-$C_6$)alkoxy optionally substituted with up to 5 fluoro;

each $R_a$ and $R_b$ is independently hydrogen, ($C_1$-$C_6$)alkyl, —$S(O)_z(C_1$-$C_6)$alkyl, —$C(O)(C_1$-$C_6)$alkyl, —$C(O)NR_g(C_1$-$C_6)$alkyl, or —$C(O)O(C_1$-$C_6)$alkyl, or $R_a$ together with $R_b$ form a heterocycle group optionally substituted with one or more $R_d$; wherein the heterocycle group optionally comprise one or more groups selected from the group consistion of O (oxygen), S (sulfur), and $NR_c$;

each $R_c$ is independently hydrogen, ($C_2$-$C_6$)alkenyl, ($C_2$-$C_6$)alkynyl, —$C(O)O(C_1$-$C_6)$alkyl, ($C_1$-$C_6$)alkoxy($C_1$-$C_6$)alkyl, hydroxy($C_1$-$C_6$)alkyl, —$C(O)NR_g(C_1$-$C_6)$alkyl, —$S(O)_z(C_1$-$C_6)$alkyl, —$C(O)(C_1$-$C_6)$alkyl, ($C_1$-$C_6$)alkyl optionally substituted with up to 5 fluoro, or ($C_1$-$C_6$)alkoxy optionally substituted with up to 5 fluoro;

each $R_d$ is independently selected from the group consisting of hydrogen, halo, oxo, hydroxy, —$C(O)NR_eR_f$, —$NR_eR_f$, hydroxy($C_1$-$C_6$)alkyl, ($C_1$-$C_6$)alkyl optionally substituted with up to 5 fluoro, and ($C_1$-$C_6$)alkoxy optionally substituted with up to 5 fluoro;

each $R_e$ and $R_f$ is independently selected from hydrogen, ($C_1$-$C_6$)alkyl, aryl, —$C(O)(C_1$-$C_6)$alkyl, —$S(O)_z(C_1$-$C_6)$alkyl, —$S(O)_zNR_g(C_1$-$C_6)$alkyl, —$C(O)NR_g(C_1$-$C_6)$alkyl, —$C(O)(C_1$-$C_6)$alkyl, or —$C(O)O(C_1$-$C_6)$alkyl;

$R_g$ is hydrogen, or ($C_1$-$C_6$)alkyl optionally substituted with up to 5 fluoro; and each L is independently hydrogen, ($C_2$-$C_6$)alkenyl, ($C_2$-$C_6$)alkynyl, —$C(O)O(C_1$-$C_6)$alkyl, ($C_1$-$C_6$)alkoxy($C_1$-$C_6$)alkyl, hydroxy($C_1$-$C_6$)alkyl, aryl, heteroaryl, heterocycle, —$CONR_eR_f$, —$S(O)_z(C_1$-$C_6)$alkyl, —$C(O)(C_1$-$C_6)$alkyl, —$C(O)NR_g(C_1$-$C_6)$alkyl, ($C_1$-$C_6$)alkyl optionally substituted with up to 5 fluoro, or ($C_1$-$C_6$)alkoxy optionally substituted with up to 5 fluoro.

3. The method of claim 1 wherein wherein said animal has an anxiety disorder, sleep disorder, depression, or schizophrenia.

4. The method of claim 3 wherein said animal has Parkinson's disease, or Huntington's disease.

5. The method of claim 1, wherein said animal has head trauma.

6. The method of claim 1 wherein the animal is an aged animal.

7. The method of claim 1 wherein said animal has Alzheimer's disease.

* * * * *

UNITED STATES PATENT AND TRADEMARK OFFICE
CERTIFICATE OF CORRECTION

PATENT NO. : 8,598,159 B2  
APPLICATION NO. : 12/949655  
DATED : December 3, 2013  
INVENTOR(S) : Kaplan et al.

It is certified that error appears in the above-identified patent and that said Letters Patent is hereby corrected as shown below:

In the Specification

In column 10 at lines 39-50,

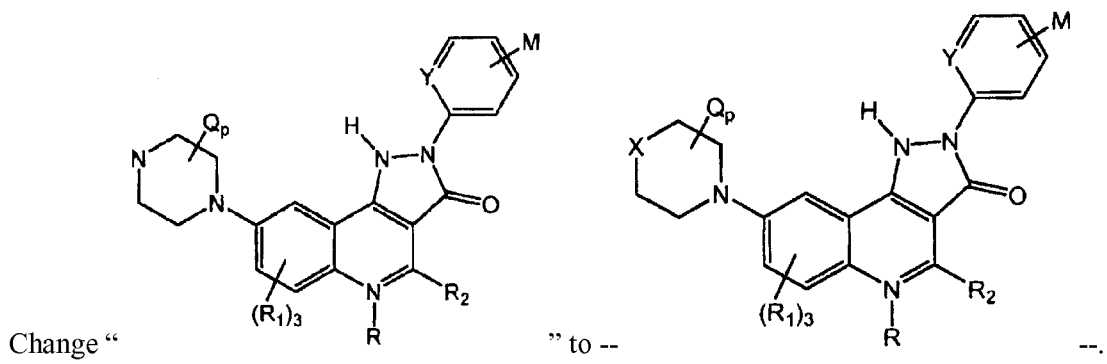

Change " " to -- --.

In column 40 at line 58, Change "Creutzfeld" to --Creutzfeldt--.
In column 41 at line 16, Change "use" to --used--.
In column 41 at line 56, Change "isopropy" to --isopropyl--.
In column 59 at line 40 (approx.), Change "piperizine" to --piperazine--.
In column 60 at line 65 (approx.), Change "piperizine" to --piperazine--.
In column 64 at line 43, Change "piperizine" to --piperazine--.
In column 65 at line 12, Change "tartarate" to --tartrate--.
In column 65 at line 13, Change "cc ketoglutarate," to --α-ketoglutarate,--.
In column 67 at line 42 (approx.), Change "Creutzfeld" to --Creutzfeldt--.
In column 135 at line 59, Change "a 1" to --α1--.
In column 135 at line 60, Change "a 5" to --α5--.

Signed and Sealed this  
Twenty-first Day of October, 2014

Michelle K. Lee  
*Deputy Director of the United States Patent and Trademark Office*

In the Claims

In column 141 at line 14, In Claim 2, Change "consistion" to --consisting--.

In column 142 at line 15 (approx.), In Claim 3, Change "wherein wherein" to --wherein--.